US012378526B2

(12) United States Patent
Jang et al.

(10) Patent No.: US 12,378,526 B2
(45) **Date of Patent: *Aug. 5, 2025**

(54) COMPOSITION FOR CULTURING NATURAL KILLER CELLS AND METHOD FOR PREPARING NATURAL KILLER CELLS BY USING SAME

(71) Applicant: GI CELL, INC., Gyeonggi-do (KR)

(72) Inventors: Myoung Ho Jang, Seoul (KR); Chun-Pyo Hong, Gyeonggi-do (KR); Dong Woo Ko, Seoul (KR); June Sub Lee, Gyeonggi-do (KR)

(73) Assignee: GI CELL, INC., Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/746,835

(22) Filed: May 17, 2022

(65) Prior Publication Data

US 2022/0372442 A1 Nov. 24, 2022

Related U.S. Application Data

(63) Continuation of application No. PCT/KR2020/016376, filed on Nov. 19, 2020.

(30) Foreign Application Priority Data

Nov. 20, 2019 (KR) ........................ 10-2019-0149779
Feb. 10, 2020 (KR) ........................ 10-2020-0015802

(51) Int. Cl.
*C12N 5/0783* (2010.01)
*A61K 35/17* (2015.01)
*C07K 14/55* (2006.01)
*C07K 14/705* (2006.01)

(52) U.S. Cl.
CPC ............ *C12N 5/0646* (2013.01); *A61K 35/17* (2013.01); *C12N 5/0636* (2013.01); *C12N 2501/2302* (2013.01); *C12N 2501/51* (2013.01)

(58) Field of Classification Search
None
See application file for complete search history.

(56) References Cited

U.S. PATENT DOCUMENTS 5,229,109 A 7/1993 Grimm et al.
11,492,384 B2 * 11/2022 Jang ................. C07K 14/70532
11,639,383 B2 * 5/2023 Jang ................. C07K 14/70532 424/85.2
11,702,633 B2 * 7/2023 Jang ..................... C12N 5/0636 424/85.2
11,857,601 B2 * 1/2024 Jang ..................... A61K 31/352
2003/0068306 A1 4/2003 Dilber
2011/0002956 A1 1/2011 Weiner et al.
2013/0149305 A1 6/2013 Ostrand-Rosenberg
2016/0045548 A1 2/2016 Lee
2023/0014358 A1 * 1/2023 Jang ................... A61K 38/1774
2023/0015408 A1 * 1/2023 Jang ................. C07K 14/70532
2024/0058420 A1 * 2/2024 Jang .................. A61K 39/3955

FOREIGN PATENT DOCUMENTS

CA 3157592 A * 5/2021
CN 109503715 A 3/2019
KR 101667096 B1 10/2016
KR 1020180069903 A 6/2018
KR 1020190060093 A 6/2018
KR 1020180100110 A 9/2018
KR 1020189100110 A 9/2018
KR 10220186 B1 1/2021
KR 102201086 B1 1/2021
RU 2312677 C2 12/2007
RU 2536242 C2 12/2014
WO 2017220989 A1 12/2017
WO 2018184964 A1 10/2018
WO 2019152663 A1 8/2019

OTHER PUBLICATIONS

Emboss Needle alignment of SEQ ID No. 6 versus 10, 2 pages, 2023 (Year: 2023).*
Emboss Needle alignment of SEQ ID No. 2 versus 11 (Year: 2023).*
Berg et al (Cytotherapy, 2009, 11(3): 341-355) (Year: 2009).*
GI Innovation (2023, pp. 1-7, gi-innovation.com/en/sub/skil/gi101.asp) (Year: 2023).*
Walzer et al (PNAS, 2007, 104(9): 3384-3389) (Year: 2007).*
Biossel, L., et al., "Umbilical Cord Mesenchymal Stem Cells Increase Expansion of Cord Blood Natural Killer Cells", Biology of Blood and Marrow Transplantation, 2008, pp. 1031-1038, vol. 14, Publisher: ASBMT.
Chan, L., et al., "IL2/B7.1 (CD80) Fusagene Transduction of AML Blasts by a Self-Inactivating Lentiviral Vector Stimulates T Cell Responses a Strategy to Generate Whole Cell Vaccines for AML", Molecular Therapy, 2005, Page(s) DOI: 10.1016/j.ymthe.2004.09.006, vol. 11, No. 1, Publisher: The American Society of Gene Therapy.

(Continued)

*Primary Examiner* — Misook Yu
*Assistant Examiner* — Marianne Dibrino
(74) *Attorney, Agent, or Firm* — HULTQUIST, PLLC; Steven J. Hultquist

(57) ABSTRACT

The invention relates to: a composition for culturing natural killer cells, comprising, as an active ingredient, a fusion protein comprising an IL-2 protein and a CD80 protein; and a method for preparing natural killer cells by using same. Particularly, a composition for culturing natural killer cells, comprising, as an active ingredient, a fusion protein comprising IL-2 or a variant thereof and CD80 or a fragment thereof, of the present invention; promotes the proliferation of natural killer cells, induces the expression of CD16 and NKp46, and increases the expression and secretion of granzyme B and perforin, thereby being effectively usable in the preparation of natural killer cells having an excellent anticancer immune function.

10 Claims, 44 Drawing Sheets

Specification includes a Sequence Listing.

(56) References Cited

OTHER PUBLICATIONS

Davis, Z.B., et al., "Natural Killer Cell AdoptiveTransfer Therapy—Exploiting the First Line of Defense Against Cancer", Cancer J., 2015, pp. 486-491, vol. 21, No. 6, Publisher: HHS Public Access.
Di Santo, J.P., "Natural Killer Cell Developmental Pathways: A Question of Balance", Annu Rev. Immunol., , pp. 257-286, vol. 24.
Ingram, W., et al., "Human CD80/IL2 lentivirus-transduced acute myeloid leukaemia (AML) cells promote natural killer (NK) cell activation and cytolytic activity: implications for a phase I clinical study", British Journal of Haematology, 2009, pp. 749-760, vol. 145, Publisher: Blackwell Publishing Ltd.
Ingram, W., et al., "Human DC80/IL2 lentivirus transduced acute myeloid leukaemia cells enhance cytolytic activity in vitro in spite of an increase in regulatory CD4+ T cells in a subset of cultures", Cancer Immunol. Immunotther, 2009, pp. 1579-1690, vol. 58.
Lifshitz, G.V., et al., "Ex vivo expanded regulatory T cells CD4+ CD25+FoxP3+CD127LOW develope strong immunosuppressive activity in patients with remitting-relapsing multiple sclerosis", Autoimmunity, 2016, pp. 388-396, vol. 49, No. 6, Publisher: Taylor & Francis.
Park, C.P., "3190-GI101, a novel triple-targeting bispecific DC80-IgG4-IL2variant fusion protein, elicits synergistic anti-tumor effects in preclinical models", ESMO 2019 Congress, Sep. 30, 2019, vol. Abst 3190.
Tang, A., et al., "The challenges and molecular approaches surrounding interleukin-2-based therapeutics in cancer", Cytokine X, 2019, pp. 100001; http://doi.org.10.1016/j.cytox.2018.100001, vol. 1, No. 1, Publisher: Elsevier.
Badri, H., et al., "Optimization of radiation dosing schedules for proneural glioblastoma", J. Math. Biol., 2015, DOI 10.1007/s00285-015-0908-x, Publisher: Springer-Verlag Berlin Heidelberg 2015, 36 pages.
Baylot, V, et al., "TCTP Has a Crucial Role in the Different Stages of Prostate Cancer Malignant Progression", Remodeling Signaling from Stem Cell to Disease, Results and Problems in Cell Differentiation 64, 2017, pp. 255-261; doi 10.1007/978-3-319-6759-6_13, vol. CH 13, Publisher: Springer International Publishing AG.
Chen, X., et al., "Fusion protein linkers: Property, design and functionality", Advanced Drug Delivery Reviews, 2012, //dx.doi.org/10.1016/j.addr.2012.09.039, Publisher: Elsevier.
Frankel, A.E., et al., "Characterization of diptheria fusion proteins targeted to the human interleukin-3 receptor", Protein Engineering, 2000, pp. 575-581, vol. 13, No. 8, Publisher: Oxford University Press.
Glaesner, W., et al., "Engineering and characterization of the long-acting glucagon-like peptide-1 analogue LY2189265, an Fc fusion protein", Diabetes/Metabolism Research and Reviews, 2010, pp. 287-296; DOI: 10.1002/dmrr.1080, vol. 26, Publisher: John Wiley & Sons, Ltd.
Maeda, Y., et al., "Engineering of Functional Chimeric Protein G-Vargula Luciferase", Analytical Biochemistry, 1997, pp. 147-152, vol. 249, No. AB972181, Publisher: Academic Press.
Pakula, A., et al., "Genetic Analysis of Protein Stability and Function", Annu. Rev. Genet., 1898, pp. 289-310, vol. 23.
Park, JC, "Abstract: GI101, a novel triple-targeting bispecific CD80-IgG4-IL2variant fusion protein, elicits synergistic", Annals of Oncology, 2019, pp. 1223P, vol. 30, No. 5.
Park, J.C., "GI101, a novel triple-targeting bispecific CD80-IgG4-IL2variant fusion protein, elicits synergistic anti-tumour effects in preclinical models", Anals of Oncology, 2019, pp. v475-v532; 10.1993/annonc/mdz253, vol. 30, No. 5, Publisher: OncologyPro.
English Translation of Office Action Issued in Russian Patent Application No. 2022113340 on Jul. 20, 2023, pp. 1-12.
Office Action Issued in Russian Patent Application No. 2022113340 on Jul. 20, 2023, pp. 1-12.
Search Report Issued in Russian Patent Application No. 2022113340 on Jul. 20, 2023, 2 pages.
Tokuriki, N., et al., "Stability effects of mutations and protein evolvability", Structural Biology, 2009, pp. 596-604, vol. 19, Publisher: Elsevier.
English translation of Office Action Issued in counterpart Chinese Patent Application No. 202080087831.0 on Jan. 19, 2023, 3 pages.
Office Action Issued in counterpart Chinese Patent Application No. 202080087831.0 on Jan. 19, 2023, 9 pages.
Search Report Issued in counterpart Chinese Patent Application No. 202080087831.0 on Jan. 16, 2023, 3 pages.
Huang, Z., et al., "Study on efficient expansion of human cytotoxic DC3-CD56+NK cells from peripheral blood", China Academic Journal, 2004, http://www.cnki.net, Publisher: Electronic Publishing House, 3 pages.
Carmenate, T., et al., "Human IL-2 Mutein with Higher Antitumor Efficacy Than Wild Type IL-2", Journal of Immunology, 2013, doi/10.4049/jimmunol.1201395, Publisher: jimmunol.org, 9 pages.
Extended European Search Report Issued on Jan. 5, 2023 in counterpart European Patent Application No. 208909697, 13 pages.
Office Action Issued on Nov. 7, 2022 in counterpart Japanese Patent Application No. 2022529598, 1 page.
English Translation of Office Action Issued on Nov. 7, 2022 in counterpart Japanese Patent Application No. 2022529598, 6 pages.
Kong, L., et al., "Expression of fusiion IL2-B7.1 (IgV+C) and effects on T lymphocytes", Biochem Cell Biol, 2007, pp. 685-695, vol. 85.
Park, D., et al., "Role of Akt in Dendritic Cell (DC) Survival and Application of an Akt "Life Switch" in DC-Based Tumor Vaccines", Molecular Therapy, 2005, pp. S436-S437, vol. 111, Publisher: The American Society of Gene Therapy.
Sauve, K., et al., "Localization in human interleukin 2 of the binding site to the chain (p55) of the interleukin 2 receptor", Proc. Natl. Acad. Sci USA, 1991, pp. 4636-4640, vol. 88.
Park, J.C., et al., "GI-101, a novel bispecific CD80-IgG4-IL2 variant fusion protein, elicits robust anti-tumor effects in preclinical models", ESMO Congress 2019, Barcelona, Spain, Sep. 27, 2019 (full-length poster, p. 1, and enlargements of sections of poster, pp. 2-11).
Haile, S.T., et al., "Soluble CD80 Restores T Cell Activation and Overcomes Tumor Cell Programmed Death Ligand 1-Mediated Immune Suppression", J Immunol, 2013, pp. 2829-2836, vol. 191, No. 5, Publisher: American Association of Immunologists, Inc.
Office Action issued on Mar. 6, 2025 for Korean Patent Application 10-2020-0155823, 8 pages.
English Translation of Office Action issued on Mar. 6, 2025 for Korean Patent Application 10-2020-0155823, 9 pages.

* cited by examiner

Anlytical size exclusion chromatography (SEC)

| | RT | Area | % Area | Height |
|---|---|---|---|---|
| 1 | 6.492 | 143663 | 1.66 | 5185 |
| 2 | 7.528 | 8497629 | 98.06 | 250509 |
| 3 | 12.546 | 24077 | 0.28 | 2005 |

| | Peak Name | RT | Area | % Area | Height |
|---|---|---|---|---|---|
| 1 | HMW1 | 15.506 | 28137 | 0.52 | 426 |
| 2 | Monomer | 18.158 | 5363386 | 99.48 | 148945 |

| | RT | Area | % Area | Height |
|---|---|---|---|---|
| 1 | 9.652 | 2996084 | 98.41 | 26478 |
| 2 | 12.535 | 48430 | 1.59 | 2882 |

| | Peak Name | RT | Area | % Area | Height |
|---|---|---|---|---|---|
| 1 | HMW | 13.321 | 33675 | 1.13 | 625 |
| 2 | monomer | 14.775 | 2952831 | 98.87 | 43291 |

SEQUENCE LISTING

```
<160> NUMBER OF SEQ ID NOS: 46

<210> SEQ ID NO 1
<211> LENGTH: 25
<212> TYPE: PRT
<213> ORGANISM: Artificial Sequence
<220> FEATURE:
```

<223> OTHER INFORMATION: signal peptide (TPA)

<400> SEQUENCE: 1

```
Met Asp Ala Met Leu Arg Gly Leu Cys Cys Val Leu Leu Leu Cys Gly
1               5                   10                  15

Ala Val Phe Val Ser Pro Ser His Ala
            20                  25
```

<210> SEQ ID NO 2
<211> LENGTH: 208
<212> TYPE: PRT
<213> ORGANISM: Artificial Sequence
<220> FEATURE:
<223> OTHER INFORMATION: hB7-1:35-242

<400> SEQUENCE: 2

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 3
<211> LENGTH: 30
<212> TYPE: PRT
<213> ORGANISM: Artificial Sequence
<220> FEATURE:
<223> OTHER INFORMATION: hinge with linker

<400> SEQUENCE: 3

```
Gly Ser Gly Gly Gly Gly Ser Gly Gly Gly Gly Ser Gly Gly Gly Gly
1               5                   10                  15

Ser Ala Glu Ser Lys Tyr Gly Pro Pro Cys Pro Pro Cys Pro
            20                  25                  30
```

<210> SEQ ID NO 4
<211> LENGTH: 216
<212> TYPE: PRT

```
<213> ORGANISM: Artificial Sequence
<220> FEATURE:
<223> OTHER INFORMATION: immunoglobulin fc

<400> SEQUENCE: 4

Ala Pro Glu Ala Ala Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly
    210                 215


<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Gly Gly Gly Ser
1               5


<210> SEQ ID NO 6
<211> LENGTH: 133
<212> TYPE: PRT
<213> ORGANISM: Artificial Sequence
<220> FEATURE:
<223> OTHER INFORMATION: hIL-2M

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45
```

```
Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 7
<211> LENGTH: 617
<212> TYPE: PRT
<213> ORGANISM: Artificial Sequence
<220> FEATURE:
<223> OTHER INFORMATION: fusion protein comprising variants of IL-2 and
      fragments of CD80

<400> SEQUENCE: 7

Met Asp Ala Met Leu Arg Gly Leu Cys Cys Val Leu Leu Leu Cys Gly
1               5                   10                  15

Ala Val Phe Val Ser Pro Ser His Ala Val Ile His Val Thr Lys Glu
            20                  25                  30

Val Lys Glu Val Ala Thr Leu Ser Cys Gly His Asn Val Ser Val Glu
        35                  40                  45

Glu Leu Ala Gln Thr Arg Ile Tyr Trp Gln Lys Glu Lys Lys Met Val
    50                  55                  60

Leu Thr Met Met Ser Gly Asp Met Asn Ile Trp Pro Glu Tyr Lys Asn
65                  70                  75                  80

Arg Thr Ile Phe Asp Ile Thr Asn Asn Leu Ser Ile Val Ile Leu Ala
                85                  90                  95

Leu Arg Pro Ser Asp Glu Gly Thr Tyr Glu Cys Val Val Leu Lys Tyr
            100                 105                 110

Glu Lys Asp Ala Phe Lys Arg Glu His Leu Ala Glu Val Thr Leu Ser
        115                 120                 125

Val Lys Ala Asp Phe Pro Thr Pro Ser Ile Ser Asp Phe Glu Ile Pro
    130                 135                 140

Thr Ser Asn Ile Arg Arg Ile Ile Cys Ser Thr Ser Gly Gly Phe Pro
145                 150                 155                 160

Glu Pro His Leu Ser Trp Leu Glu Asn Gly Glu Glu Leu Asn Ala Ile
                165                 170                 175

Asn Thr Thr Val Ser Gln Asp Pro Glu Thr Glu Leu Tyr Ala Val Ser
            180                 185                 190

Ser Lys Leu Asp Phe Asn Met Thr Thr Asn His Ser Phe Met Cys Leu
        195                 200                 205

Ile Lys Tyr Gly His Leu Arg Val Asn Gln Thr Phe Asn Trp Asn Thr
    210                 215                 220

Thr Lys Gln Glu His Phe Pro Asp Asn Gly Ser Gly Gly Gly Gly Ser
225                 230                 235                 240

Gly Gly Gly Gly Ser Gly Gly Gly Gly Ser Ala Glu Ser Lys Tyr Gly
                245                 250                 255

Pro Pro Cys Pro Pro Cys Pro Ala Pro Glu Ala Ala Gly Gly Pro Ser
```

```
            260                 265                 270

Val Phe Leu Phe Pro Pro Lys Pro Lys Asp Gln Leu Met Ile Ser Arg
        275                 280                 285

Thr Pro Glu Val Thr Cys Val Val Val Asp Val Ser Gln Glu Asp Pro
    290                 295                 300

Glu Val Gln Phe Asn Trp Tyr Val Asp Gly Val Glu Val His Asn Ala
305                 310                 315                 320

Lys Thr Lys Pro Arg Glu Glu Gln Phe Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Gly Leu Pro Ser Ser Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Gln Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Arg Leu Thr Val Asp Lys Ser
        435                 440                 445

Arg Trp Gln Glu Gly Asn Val Phe Ser Cys Ser Val Leu His Glu Ala
    450                 455                 460

Leu His Asn His Tyr Thr Gln Lys Ser Leu Ser Leu Ser Leu Gly Gly
465                 470                 475                 480

Gly Gly Gly Ser Ala Pro Thr Ser Ser Ser Thr Lys Lys Thr Gln Leu
                485                 490                 495

Gln Leu Glu His Leu Leu Leu Asp Leu Gln Met Ile Leu Asn Gly Ile
            500                 505                 510

Asn Asn Tyr Lys Asn Pro Lys Leu Thr Ala Met Leu Thr Ala Lys Phe
        515                 520                 525

Tyr Met Pro Lys Lys Ala Thr Glu Leu Lys His Leu Gln Cys Leu Glu
    530                 535                 540

Glu Glu Leu Lys Pro Leu Glu Glu Val Leu Asn Leu Ala Gln Ser Lys
545                 550                 555                 560

Asn Phe His Leu Arg Pro Arg Asp Leu Ile Ser Asn Ile Asn Val Ile
                565                 570                 575

Val Leu Glu Leu Lys Gly Ser Glu Thr Thr Phe Met Cys Glu Tyr Ala
            580                 585                 590

Asp Glu Thr Ala Thr Ile Val Glu Phe Leu Asn Arg Trp Ile Thr Phe
        595                 600                 605

Cys Gln Ser Ile Ile Ser Thr Leu Thr
    610                 615
```

<210> SEQ ID NO 8
<211> LENGTH: 1857
<212> TYPE: DNA
<213> ORGANISM: Artificial Sequence
<220> FEATURE:
<223> OTHER INFORMATION: nucleotides coding fusion protein (GI101)

<400> SEQUENCE: 8

```
atggatgcta tgctgagagg cctgtgttgc gtgctgctgc tgtgtggcgc tgtgttcgtg      60
```

```
tctccttctc acgctgtgat ccacgtgacc aaagaagtga aagaggtcgc cacactgtcc    120

tgcggccaca acgtttcagt ggaagaactg gcccagacca ggatctactg gcagaaagaa    180

aagaaaatgg tgctgaccat gatgtccggc gacatgaaca tctggcctga gtacaagaac    240

cggaccatct tcgacatcac caacaacctg tccatcgtga ttctggccct gaggccttct    300

gatgagggca cctatgagtg cgtggtgctg aagtacgaga aggacgcctt caagcgcgag    360

cacctggctg aagtgacact gtccgtgaag gccgactttc ccacaccttc catctccgac    420

ttcgagatcc ctacctccaa catccggcgg atcatctgtt ctacctctgg cggctttcct    480

gagcctcacc tgtcttggct ggaaaacggc gaggaactga acgccatcaa caccaccgtg    540

tctcaggacc ccgaaaccga gctgtacgct gtgtcctcca agctggactt caacatgacc    600

accaaccaca gcttcatgtg cctgattaag tacggccacc tgagagtgaa ccagaccttc    660

aactggaaca ccaccaagca agagcacttc cctgacaatg gatctggcgg cggaggttct    720

ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840

aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctagatgg caagagggca acgtgttctc ctgctctgtg   1380

ctgcacgagg ccctgcacaa tcactacacc cagaagtccc tgtctctgtc tcttggaggt   1440

ggtggcggtt ctgcccctac cagctcctct accaagaaaa cccagctcca gttggagcat   1500

ctgctgctgg acctccagat gattctgaac gggatcaaca actataagaa ccccaagctg   1560

accgccatgc tgaccgctaa gttctacatg cccaagaagg ccaccgagct gaagcacctc   1620

cagtgcctgg aagaagaact gaagcccctg gaagaggtgc tgaatctggc ccagtccaag   1680

aacttccacc tgaggccacg ggacctgatc agcaacatca acgtgatcgt gctggaactg   1740

aagggctccg agacaacctt tatgtgcgag tacgccgacg agacagccac catcgtggaa   1800

tttctgaacc ggtggatcac cttctgccag agcatcatct ccacactgac ctgatga      1857
```

```
<210> SEQ ID NO 9
<211> LENGTH: 592
<212> TYPE: PRT
<213> ORGANISM: Artificial Sequence
<220> FEATURE:
<223> OTHER INFORMATION: fusion protein (GI101)

<400> SEQUENCE: 9

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45
```

```
Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460
```

```
Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590


<210> SEQ ID NO 10
<211> LENGTH: 133
<212> TYPE: PRT
<213> ORGANISM: Artificial Sequence
<220> FEATURE:
<223> OTHER INFORMATION: hIL-2

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 11
<211> LENGTH: 288
<212> TYPE: PRT
<213> ORGANISM: Artificial Sequence
<220> FEATURE:
<223> OTHER INFORMATION: CD80

<400> SEQUENCE: 11

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45
```

```
Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285


<210> SEQ ID NO 12
<211> LENGTH: 215
<212> TYPE: PRT
<213> ORGANISM: Artificial Sequence
<220> FEATURE:
<223> OTHER INFORMATION: modified Fc

<400> SEQUENCE: 12

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125
```

```
Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
        195                 200                 205

Leu Ser Leu Ser Leu Gly Lys
    210                 215


<210> SEQ ID NO 13
<211> LENGTH: 306
<212> TYPE: PRT
<213> ORGANISM: Artificial Sequence
<220> FEATURE:
<223> OTHER INFORMATION: mCD80

<400> SEQUENCE: 13

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270
```

```
Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305


<210> SEQ ID NO 14
<211> LENGTH: 1848
<212> TYPE: DNA
<213> ORGANISM: Artificial Sequence
<220> FEATURE:
<223> OTHER INFORMATION: nucleotides coding fusion protein (mGI101)

<400> SEQUENCE: 14

atggatgcta tgctgagagg cctgtgttgc gtgctgctgc tgtgtggcgc tgtgttcgtg      60

tctccttctc acgctgtgga cgagcagctc tccaagtccg tgaaggataa ggtcctgctg     120

ccttgccggt acaactctcc tcacgaggac gagtctgagg accggatcta ctggcagaaa     180

cacgacaagg tggtgctgtc cgtgatcgcc ggaaagctga aagtgtggcc tgagtacaag     240

aacaggaccc tgtacgacaa caccacctac agcctgatca tcctgggcct cgtgctgagc     300

gatagaggca cctattcttg cgtggtgcag aagaaagagc ggggcaccta cgaagtgaag     360

cacctggctc tggtcaagct gtccatcaag gccgacttca gcacccctaa catcaccgag     420

tctggcaacc cttccgccga caccaagaga atcacctgtt tcgcctctgg cggcttccct     480

aagcctcggt tctcttggct ggaaaacggc agagagctgc ccggcatcaa taccaccatt     540

tctcaggacc cagagtccga gctgtacacc atctccagcc agctcgactt taacaccacc     600

agaaaccaca ccatcaagtg cctgattaag tacggcgacg cccacgtgtc cgaggacttt     660

acttgggaga aacctcctga ggaccctcct gactctggat ctggcggcgg aggttctggc     720

ggaggtggaa gcggaggcgg aggatctgct gagtctaagt atggccctcc ttgtcctcca     780

tgtcctgctc cagaagctgc tggcggaccc tctgtgttcc tgtttcctcc aaagcctaag     840

gaccagctca tgatctctcg gacccctgaa gtgacctgcg tggtggtgga tgtgtctcaa     900

gaggaccctg aggtgcagtt caattggtac gtggacggcg tggaagtgca caacgccaag     960

accaagccta gagaggaaca gttcaactcc acctatagag tggtgtccgt gctgaccgtg    1020

ctgcaccagg attggctgaa cggcaaagag tacaagtgca aggtgtccaa caagggcctg    1080

ccttccagca tcgaaaagac catcagcaag gctaagggcc agcctaggga accccaggtt    1140

tacaccctgc ctccaagcca agaggaaatg accaagaacc aggtgtccct gacctgcctg    1200

gtcaagggct tctacccttc cgacattgcc gtggaatggg agtccaatgg ccagcctgag    1260

aacaactaca agaccacacc tcctgtgctg gactccgacg gctccttctt tctgtactct    1320

cgcctgaccg tggacaagtc taggtggcaa gagggcaacg tgttctcctg ctctgtgctg    1380

cacgaggctc tgcacaacca ctacacccag aagtccctgt ctctgtctct tggaggtggt    1440

ggcggttctg cccctacctc cagctctacc aagaaaaccc agctccagtt ggagcatctg    1500

ctgctggacc tccagatgat cctgaatggc atcaacaatt acaagaaccc caagctgacc    1560

gccatgctga ccgctaagtt ctacatgccc aagaaggcca ccgagctgaa gcacttgcag    1620

tgcctggaag aggaactgaa gcccctggaa gaagtgctga atctggccca gtccaagaac    1680

ttccacctga ggcctaggga cctgatctcc aacatcaacg tgatcgtgct ggaactgaaa    1740

ggctccgaga caaccttcat gtgcgagtac gccgacgaga cagccaccat cgtggaattt    1800
```

ctgaaccggt ggatcacctt ctgccagagc atcatctcca cactgacc 1848

<210> SEQ ID NO 15
<211> LENGTH: 616
<212> TYPE: PRT
<213> ORGANISM: Artificial Sequence
<220> FEATURE:
<223> OTHER INFORMATION: fusion protein (mGI101)

<400> SEQUENCE: 15

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Gly Ser Gly
225                 230                 235                 240

Gly Gly Gly Ser Gly Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350
```

```
Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
            500                 505                 510

Asn Tyr Lys Asn Pro Lys Leu Thr Ala Met Leu Thr Ala Lys Phe Tyr
        515                 520                 525

Met Pro Lys Lys Ala Thr Glu Leu Lys His Leu Gln Cys Leu Glu Glu
    530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
        595                 600                 605

Gln Ser Ile Ile Ser Thr Leu Thr
    610                 615


<210> SEQ ID NO 16
<211> LENGTH: 1437
<212> TYPE: DNA
<213> ORGANISM: Artificial Sequence
<220> FEATURE:
<223> OTHER INFORMATION: nucleotides coding fusion protein (GI101C1)

<400> SEQUENCE: 16

atggatgcta tgctgagagg cctgtgttgc gtgctgctgc tgtgtggcgc tgtgttcgtg      60

tctccttctc acgctgtgat ccacgtgacc aaagaagtga aagaggtcgc cacactgtcc     120

tgcggccaca acgtttcagt ggaagaactg gcccagacca ggatctactg gcagaaagaa     180

aagaaaatgg tgctgaccat gatgtccggc gacatgaaca tctggcctga gtacaagaac     240

cggaccatct tcgacatcac caacaacctg tccatcgtga ttctggccct gaggccttct     300

gatgagggca cctatgagtg cgtggtgctg aagtacgaga aggacgcctt caagcgcgag     360

cacctggctg aagtgacact gtccgtgaag gccgactttc ccacaccttc catctccgac     420

ttcgagatcc ctacctccaa catccggcgg atcatctgtt ctacctctgg cggctttcct     480

gagcctcacc tgtcttggct ggaaaacggc gaggaactga acgccatcaa caccaccgtg     540
```

```
tctcaggacc ccgaaaccga gctgtacgct gtgtcctcca agctggactt caacatgacc    600

accaaccaca gcttcatgtg cctgattaag tacggccacc tgagagtgaa ccagaccttc    660

aactggaaca ccaccaagca agagcacttc cctgacaatg gatctggcgg cggaggttct    720

ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840

aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctaggtgg caagagggca acgtgttctc ctgctctgtg   1380

ctgcacgagg ccctgcacaa tcactacacc cagaagtccc tgtctctgtc cctgggc      1437
```

```
<210> SEQ ID NO 17
<211> LENGTH: 454
<212> TYPE: PRT
<213> ORGANISM: Artificial Sequence
<220> FEATURE:
<223> OTHER INFORMATION: fusion protein (GI101C1)

<400> SEQUENCE: 17

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

```
Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly
    450
```

<210> SEQ ID NO 18
<211> LENGTH: 1176
<212> TYPE: DNA
<213> ORGANISM: Artificial Sequence
<220> FEATURE:
<223> OTHER INFORMATION: nucleotides coding fusion protein (GI101C2)

<400> SEQUENCE: 18

```
atggatgcta tgctgagagg cctgtgttgc gtgctgctgc tgtgtggcgc tgtgttcgtg      60

tctccatctc acgccgctga gtctaagtac ggccctcctt gtcctccatg tcctgctcca     120

gaagctgctg gcggaccctc tgtgttcctg tttcctccaa agcctaagga ccagctcatg     180

atctctcgga cccctgaagt gacctgcgtg gtggtggatg tgtctcaaga ggaccctgag     240

gtgcagttca attggtacgt ggacggcgtg gaagtgcaca acgccaagac caagcctaga     300

gaggaacagt tcaactccac ctacagagtg gtgtccgtgc tgaccgtgct gcaccaggat     360

tggctgaacg gcaaagagta caagtgcaag gtgtccaaca agggcctgcc ttccagcatc     420

gaaaagacca tctccaaggc taagggccag cctagggaac cccaggttta caccctgcct     480

ccaagccaag aggaaatgac caagaaccag gtgtccctga cctgcctggt caagggcttc     540

tacccttccg acattgccgt ggaatgggag tccaatggcc agcctgagaa caactacaag     600

accacacctc ctgtgctgga ctccgacggc tccttctttc tgtactctcg cctgaccgtg     660
```

```
gacaagtcta ggtggcaaga gggcaacgtg ttctcctgct ctgtgctgca cgaggccctg    720

cacaatcact acacccagaa gtccctgtct ctgtctcttg gcggaggcgg aggatctgct    780

cctacctcca gctccaccaa gaaaacccag ctccagttgg agcatctgct gctggacctc    840

cagatgatcc tgaatggcat caacaattac aagaacccca agctgaccgc catgctgacc    900

gctaagttct acatgcccaa gaaggccacc gagctgaagc acctccagtg cctggaagag    960

gaactgaagc ccctggaaga agtgctgaat ctggcccagt ccaagaactt ccacctgagg   1020

cctagggacc tgatctccaa catcaacgtg atcgtgctgg aactgaaagg ctccgagaca   1080

accttcatgt gcgagtacgc cgacgagaca gccaccatcg tggaatttct gaaccggtgg   1140

atcaccttct gccagtccat catctccaca ctgacc                             1176


<210> SEQ ID NO 19
<211> LENGTH: 367
<212> TYPE: PRT
<213> ORGANISM: Artificial Sequence
<220> FEATURE:
<223> OTHER INFORMATION: fusion protein (GI101C2)

<400> SEQUENCE: 19

Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Leu His Glu Ala Leu His Asn His Tyr Thr Gln Lys Ser Leu
    210                 215                 220

Ser Leu Ser Leu Gly Gly Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Ala
            260                 265                 270
```

```
Met Leu Thr Ala Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Cys Gln Ser Ile Ile Ser Thr Leu Thr
        355                 360                 365


<210> SEQ ID NO 20
<211> LENGTH: 1434
<212> TYPE: DNA
<213> ORGANISM: Artificial Sequence
<220> FEATURE:
<223> OTHER INFORMATION: nucleotides coding fusion protein (mGI101C1)

<400> SEQUENCE: 20

atggatgcta tgctgagagg cctgtgttgc gtgctgctgc tgtgtggcgc tgtgttcgtg      60

tctccttctc acgctgtgga cgagcagctc tccaagtccg tgaaggataa ggtcctgctg     120

ccttgccggt acaactctcc tcacgaggac gagtctgagg accggatcta ctggcagaaa     180

cacgacaagg tggtgctgtc cgtgatcgcc ggaaagctga aagtgtggcc tgagtacaag     240

aacaggaccc tgtacgacaa caccacctac agcctgatca tcctgggcct cgtgctgagc     300

gatagaggca cctattcttg cgtggtgcag aagaaagagc ggggcaccta cgaagtgaag     360

cacctggctc tggtcaagct gtccatcaag gccgacttca gcacccctaa catcaccgag     420

tctggcaacc cttccgccga caccaagaga atcacctgtt tcgcctctgg cggcttccct     480

aagcctcggt tctcttggct ggaaaacggc agagagctgc ccggcatcaa taccaccatt     540

tctcaggacc cagagtccga gctgtacacc atctccagcc agctcgactt taacaccacc     600

agaaaccaca ccatcaagtg cctgattaag tacggcgacg cccacgtgtc cgaggacttt     660

acttgggaga aacctcctga ggaccctcct gactctggat ctggcggcgg aggttctggc     720

ggaggtggaa gcggaggcgg aggatctgct gagtctaagt atggccctcc ttgtcctcca     780

tgtcctgctc cagaagctgc tggcggaccc tctgtgttcc tgtttcctcc aaagcctaag     840

gaccagctca tgatctctcg gacccctgaa gtgacctgcg tggtggtgga tgtgtctcaa     900

gaggaccctg aggtgcagtt caattggtac gtggacggcg tggaagtgca caacgccaag     960

accaagccta gagaggaaca gttcaactcc acctatagag tggtgtccgt gctgaccgtg    1020

ctgcaccagg attggctgaa cggcaaagag tacaagtgca aggtgtccaa caagggcctg    1080

ccttccagca tcgaaaagac catcagcaag gctaagggcc agcctaggga accccaggtt    1140

tacaccctgc ctccaagcca agaggaaatg accaagaacc aggtgtccct gacctgcctg    1200

gtcaagggct tctacccttc cgacattgcc gtggaatggg agtccaatgg ccagcctgag    1260

aacaactaca agaccacacc tcctgtgctg gactccgacg gctccttctt tctgtactct    1320

cgcctgaccg tggacaagtc taggtggcaa gagggcaacg tgttctcctg ctctgtgctg    1380

cacgaggctc tgcacaacca ctacacccag aagtccctgt ctctgtccct gggc          1434


<210> SEQ ID NO 21
```

```
<211> LENGTH: 478
<212> TYPE: PRT
<213> ORGANISM: Artificial Sequence
<220> FEATURE:
<223> OTHER INFORMATION: fusion protein (mGI101C1)

<400> SEQUENCE: 21

Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Gly Ser Gly
225                 230                 235                 240

Gly Gly Gly Ser Gly Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380
```

```
Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly
465                 470                 475


<210> SEQ ID NO 22
<211> LENGTH: 133
<212> TYPE: PRT
<213> ORGANISM: Artificial Sequence
<220> FEATURE:
<223> OTHER INFORMATION: variants of IL-2 (3M, M45)

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 23
<211> LENGTH: 133
<212> TYPE: PRT
<213> ORGANISM: Artificial Sequence
<220> FEATURE:
<223> OTHER INFORMATION: variants of IL-2 (3M, M61)

<400> SEQUENCE: 23

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Arg Glu Leu Lys
    50                  55                  60

Pro Leu Glu Glu Val Leu Asn Leu Ala Gln Ser Lys Asn Phe His Leu
```

```
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 24
<211> LENGTH: 133
<212> TYPE: PRT
<213> ORGANISM: Artificial Sequence
<220> FEATURE:
<223> OTHER INFORMATION: variants of IL-2 (3M, M72)

<400> SEQUENCE: 24

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 25
<211> LENGTH: 1851
<212> TYPE: DNA
<213> ORGANISM: Artificial Sequence
<220> FEATURE:
<223> OTHER INFORMATION: nucleotides coding fusion protein (GI102-M45)

<400> SEQUENCE: 25

atggatgcta tgctgagagg cctgtgttgc gtgctgctgc tgtgtggcgc tgtgttcgtg      60

tctccttctc acgctgtgat ccacgtgacc aaagaagtga aagaggtcgc cacactgtcc     120

tgcggccaca acgtttcagt ggaagaactg gcccagacca ggatctactg gcagaaagaa     180

aagaaaatgg tgctgaccat gatgtccggc gacatgaaca tctggcctga gtacaagaac     240

cggaccatct tcgacatcac caacaacctg tccatcgtga ttctggccct gaggccttct     300

gatgagggca cctatgagtg cgtggtgctg aagtacgaga aggacgcctt caagcgcgag     360

cacctggctg aagtgacact gtccgtgaag gccgactttc ccacaccttc catctccgac     420

ttcgagatcc ctacctccaa catccggcgg atcatctgtt ctacctctgg cggctttcct     480

gagcctcacc tgtcttggct ggaaaacggc gaggaactga acgccatcaa caccaccgtg     540
```

```
tctcaggacc ccgaaaccga gctgtacgct gtgtcctcca agctggactt caacatgacc    600

accaaccaca gcttcatgtg cctgattaag tacggccacc tgagagtgaa ccagaccttc    660

aactggaaca ccaccaagca agagcacttc cctgacaatg gatctggcgg cggaggttct    720

ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840

aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctagatgg caagagggca acgtgttctc ctgctctgtg   1380

ctgcacgagg ccctgcacaa tcactacacc cagaagtccc tgtctctgtc tcttggaggt   1440

ggtggcggtt ctgcccctac cagctcctct accaagaaaa cccagctcca gttggagcat   1500

ctgctgctgg acctccagat gattctgaac gggatcaaca actataagaa ccccaagctg   1560

accgccatgc tgaccgctaa gttcgccatg cccaagaagg ccaccgagct gaagcacctc   1620

cagtgcctgg aagaagaact gaagcccctg gaagaggtgc tgaatctggc ccagtccaag   1680

aacttccacc tgaggccacg ggacctgatc agcaacatca acgtgatcgt gctggaactg   1740

aagggctccg agacaacctt tatgtgcgag tacgccgacg agacagccac catcgtggaa   1800

tttctgaacc ggtggatcac cttctgccag agcatcatct ccacactgac c            1851
```

```
<210> SEQ ID NO 26
<211> LENGTH: 592
<212> TYPE: PRT
<213> ORGANISM: Artificial Sequence
<220> FEATURE:
<223> OTHER INFORMATION: fusion protein (GI102-M45)

<400> SEQUENCE: 26

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
```

```
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Ala Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560
```

```
Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590


<210> SEQ ID NO 27
<211> LENGTH: 1851
<212> TYPE: DNA
<213> ORGANISM: Artificial Sequence
<220> FEATURE:
<223> OTHER INFORMATION: nucleotides coding fusion protein (GI102-M61)

<400> SEQUENCE: 27

atggatgcta tgctgagagg cctgtgttgc gtgctgctgc tgtgtggcgc tgtgttcgtg      60

tctccttctc acgctgtgat ccacgtgacc aaagaagtga aagaggtcgc cacactgtcc     120

tgcggccaca acgtttcagt ggaagaactg gcccagacca ggatctactg gcagaaagaa     180

aagaaaatgg tgctgaccat gatgtccggc gacatgaaca tctggcctga gtacaagaac     240

cggaccatct tcgacatcac caacaacctg tccatcgtga ttctggccct gaggccttct     300

gatgagggca cctatgagtg cgtggtgctg aagtacgaga aggacgcctt caagcgcgag     360

cacctggctg aagtgacact gtccgtgaag gccgactttc ccacaccttc catctccgac     420

ttcgagatcc ctacctccaa catccggcgg atcatctgtt ctacctctgg cggctttcct     480

gagcctcacc tgtcttggct ggaaaacggc gaggaactga acgccatcaa caccaccgtg     540

tctcaggacc ccgaaaccga gctgtacgct gtgtcctcca agctggactt caacatgacc     600

accaaccaca gcttcatgtg cctgattaag tacggccacc tgagagtgaa ccagaccttc     660

aactggaaca ccaccaagca agagcacttc cctgacaatg gatctggcgg cggaggttct     720

ggcggaggtg gaagcggagg cggaggatct gctgagtcta agtatggccc tccttgtcct     780

ccatgtcctg ctccagaagc tgctggcgga ccctctgtgt tcctgtttcc tccaaagcct     840

aaggaccagc tcatgatctc tcggacaccc gaagtgacct gcgtggtggt ggatgtgtct     900

caagaggacc ctgaggtgca gttcaattgg tacgtggacg gcgtggaagt gcacaacgcc     960

aagaccaagc ctagagagga acagttcaac tccacctaca gagtggtgtc cgtgctgacc    1020

gtgctgcacc aggattggct gaacggcaaa gagtacaagt gcaaggtgtc caacaagggc    1080

ctgccttcca gcatcgaaaa gaccatctcc aaggctaagg gccagcctag ggaaccccag    1140

gtttacaccc tgcctccaag ccaagaggaa atgaccaaga accaggtgtc cctgacctgc    1200

ctggtcaagg gcttctaccc ttccgacatt gccgtggaat gggagtccaa tggccagcct    1260

gagaacaact acaagaccac acctcctgtg ctggactccg acggctcctt ctttctgtac    1320

tctcgcctga ccgtggacaa gtctagatgg caagagggca acgtgttctc ctgctctgtg    1380

ctgcacgagg ccctgcacaa tcactacacc cagaagtccc tgtctctgtc tcttggaggt    1440

ggtggcggtt ctgcccctac cagctcctct accaagaaaa cccagctcca gttggagcat    1500

ctgctgctgg acctccagat gattctgaac gggatcaaca actataagaa ccccaagctg    1560

accgccatgc tgaccgctaa gttctacatg cccaagaagg ccaccgagct gaagcacctc    1620

cagtgcctgg aaagggaact gaagcccctg gaagaggtgc tgaatctggc ccagtccaag    1680

aacttccacc tgaggccacg ggacctgatc agcaacatca acgtgatcgt gctggaactg    1740

aagggctccg agacaacctt tatgtgcgag tacgccgacg agacagccac catcgtggaa    1800

tttctgaacc ggtggatcac cttctgccag agcatcatct ccacactgac c             1851
```

<210> SEQ ID NO 28
<211> LENGTH: 592
<212> TYPE: PRT
<213> ORGANISM: Artificial Sequence
<220> FEATURE:
<223> OTHER INFORMATION: fusion protein (GI102-M61)

<400> SEQUENCE: 28

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365
```

```
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Arg Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

```
<210> SEQ ID NO 29
<211> LENGTH: 1857
<212> TYPE: DNA
<213> ORGANISM: Artificial Sequence
<220> FEATURE:
<223> OTHER INFORMATION: nucleotides coding fusion protein (GI102-M72)

<400> SEQUENCE: 29

atggatgcta tgctgagagg cctgtgttgc gtgctgctgc tgtgtggcgc tgtgttcgtg      60

tctccttctc acgctgtgat ccacgtgacc aaagaagtga aagaggtcgc cacactgtcc     120

tgcggccaca acgtttcagt ggaagaactg gcccagacca ggatctactg gcagaaagaa     180

aagaaaatgg tgctgaccat gatgtccggc gacatgaaca tctggcctga gtacaagaac     240

cggaccatct tcgacatcac caacaacctg tccatcgtga ttctggccct gaggccttct     300

gatgagggca cctatgagtg cgtggtgctg aagtacgaga aggacgcctt caagcgcgag     360

cacctggctg aagtgacact gtccgtgaag gccgactttc ccacaccttc catctccgac     420

ttcgagatcc ctacctccaa catccggcgg atcatctgtt ctacctctgg cggctttcct     480

gagcctcacc tgtcttggct ggaaaacggc gaggaactga acgccatcaa caccaccgtg     540

tctcaggacc ccgaaaccga gctgtacgct gtgtcctcca agctggactt caacatgacc     600

accaaccaca gcttcatgtg cctgattaag tacggccacc tgagagtgaa ccagaccttc     660

aactggaaca ccaccaagca agagcacttc cctgacaatg gatctggcgg cggaggttct     720

ggcggaggtg gaagcggagg cggaggatct gctgagtcta agtatggccc tccttgtcct     780

ccatgtcctg ctccagaagc tgctggcgga ccctctgtgt tcctgtttcc tccaaagcct     840
```

```
aaggaccagc tcatgatctc tcggacaccc gaagtgacct gcgtggtggt ggatgtgtct    900

caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctagatgg caagagggca acgtgttctc ctgctctgtg   1380

ctgcacgagg ccctgcacaa tcactacacc cagaagtccc tgtctctgtc tcttggaggt   1440

ggtggcggtt ctgcccctac cagctcctct accaagaaaa cccagctcca gttggagcat   1500

ctgctgctgg acctccagat gattctgaac gggatcaaca actataagaa ccccaagctg   1560

accgccatgc tgaccgctaa gttctacatg cccaagaagg ccaccgagct gaagcacctc   1620

cagtgcctgg aagaagaact gaagcccctg gaagaggtgc tgaatggggc ccagtccaag   1680

aacttccacc tgaggccacg ggacctgatc agcaacatca acgtgatcgt gctggaactg   1740

aagggctccg agacaacctt tatgtgcgag tacgccgacg agacagccac catcgtggaa   1800

tttctgaacc ggtggatcac cttctgccag agcatcatct ccacactgac ctgatga      1857
```

<210> SEQ ID NO 30
<211> LENGTH: 592
<212> TYPE: PRT
<213> ORGANISM: Artificial Sequence
<220> FEATURE:
<223> OTHER INFORMATION: fusion protein (GI102-M72)

<400> SEQUENCE: 30

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
```

```
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Ala Met Leu Thr Ala Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Gly Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

<210> SEQ ID NO 31

<211> LENGTH: 1851
<212> TYPE: DNA
<213> ORGANISM: Artificial Sequence
<220> FEATURE:
<223> OTHER INFORMATION: nucleotides coding fusion protein (GI101w)

<400> SEQUENCE: 31

```
atggatgcta tgctgagagg cctgtgttgc gtgctgctgc tgtgtggcgc tgtgttcgtg     60
tctccttctc acgctgtgat ccacgtgacc aaagaagtga aagaggtcgc cacactgtcc    120
tgcggccaca acgtttcagt ggaagaactg gcccagacca ggatctactg gcagaaagaa    180
aagaaaatgg tgctgaccat gatgtccggc gacatgaaca tctggcctga gtacaagaac    240
cggaccatct tcgacatcac caacaacctg tccatcgtga ttctggccct gaggccttct    300
gatgagggca cctatgagtg cgtggtgctg aagtacgaga aggacgcctt caagcgcgag    360
cacctggctg aagtgacact gtccgtgaag gccgactttc ccacaccttc catctccgac    420
ttcgagatcc ctacctccaa catccggcgg atcatctgtt ctacctctgg cggctttcct    480
gagcctcacc tgtcttggct ggaaaacggc gaggaactga acgccatcaa caccaccgtg    540
tctcaggacc ccgaaaccga gctgtacgct gtgtcctcca agctggactt caacatgacc    600
accaaccaca gcttcatgtg cctgattaag tacggccacc tgagagtgaa ccagaccttc    660
aactggaaca ccaccaagca agagcacttc cctgacaatg gatctggcgg cggaggttct    720
ggcggaggtg gaagcggagg cggaggatct gctgagtcta agtatggccc tccttgtcct    780
ccatgtcctg ctccagaagc tgctggcgga ccctctgtgt tcctgtttcc tccaaagcct    840
aaggaccagc tcatgatctc tcggacaccc gaagtgacct gcgtggtggt ggatgtgtct    900
caagaggacc ctgaggtgca gttcaattgg tacgtggacg gcgtggaagt gcacaacgcc    960
aagaccaagc ctagagagga acagttcaac tccacctaca gagtggtgtc cgtgctgacc   1020
gtgctgcacc aggattggct gaacggcaaa gagtacaagt gcaaggtgtc caacaagggc   1080
ctgccttcca gcatcgaaaa gaccatctcc aaggctaagg gccagcctag ggaaccccag   1140
gtttacaccc tgcctccaag ccaagaggaa atgaccaaga accaggtgtc cctgacctgc   1200
ctggtcaagg gcttctaccc ttccgacatt gccgtggaat gggagtccaa tggccagcct   1260
gagaacaact acaagaccac acctcctgtg ctggactccg acggctcctt ctttctgtac   1320
tctcgcctga ccgtggacaa gtctagatgg caagagggca acgtgttctc ctgctctgtg   1380
ctgcacgagg ccctgcacaa tcactacacc cagaagtccc tgtctctgtc tcttggaggt   1440
ggtggcggtt ctgcccctac cagctcctct accaagaaaa cccagctcca gttggagcat   1500
ctgctgctgg acctccagat gattctgaac gggatcaaca actataagaa ccccaagctg   1560
acccgcatgc tgacctttaa gttctacatg cccaagaagg ccaccgagct gaagcacctc   1620
cagtgcctgg aagaagaact gaagcccctg gaagaggtgc tgaatctggc ccagtccaag   1680
aacttccacc tgaggccacg ggacctgatc agcaacatca acgtgatcgt gctggaactg   1740
aagggctccg agacaacctt tatgtgcgag tacgccgacg agacagccac catcgtggaa   1800
tttctgaacc ggtggatcac cttctgccag agcatcatct ccacactgac c            1851
```

<210> SEQ ID NO 32
<211> LENGTH: 592
<212> TYPE: PRT
<213> ORGANISM: Artificial Sequence
<220> FEATURE:
<223> OTHER INFORMATION: fusion protein (GI101w)

<400> SEQUENCE: 32

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

```
Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

<210> SEQ ID NO 33
<211> LENGTH: 1848
<212> TYPE: DNA
<213> ORGANISM: Artificial Sequence
<220> FEATURE:
<223> OTHER INFORMATION: nucleotides coding fusion protein (mGI102-M61)

<400> SEQUENCE: 33

```
atggatgcta tgctgagagg cctgtgttgc gtgctgctgc tgtgtggcgc tgtgttcgtg     60

tctccttctc acgctgtgga cgagcagctc tccaagtccg tgaaggataa ggtcctgctg    120

ccttgccggt acaactctcc tcacgaggac gagtctgagg accggatcta ctggcagaaa    180

cacgacaagg tggtgctgtc cgtgatcgcc ggaaagctga aagtgtggcc tgagtacaag    240

aacaggaccc tgtacgacaa caccacctac agcctgatca tcctgggcct cgtgctgagc    300

gatagaggca cctattcttg cgtggtgcag aagaaagagc ggggcaccta cgaagtgaag    360

cacctggctc tggtcaagct gtccatcaag gccgacttca gcacccctaa catcaccgag    420

tctggcaacc cttccgccga caccaagaga atcacctgtt tcgcctctgg cggcttccct    480

aagcctcggt tctcttggct ggaaaacggc agagagctgc ccggcatcaa taccaccatt    540

tctcaggacc cagagtccga gctgtacacc atctccagcc agctcgactt taacaccacc    600

agaaaccaca ccatcaagtg cctgattaag tacggcgacg cccacgtgtc cgaggacttt    660

acttgggaga aacctcctga ggaccctcct gactctggat ctggcggcgg aggttctggc    720

ggaggtggaa gcggaggcgg aggatctgct gagtctaagt atggccctcc ttgtcctcca    780

tgtcctgctc cagaagctgc tggcggaccc tctgtgttcc tgtttcctcc aaagcctaag    840

gaccagctca tgatctctcg gacccctgaa gtgacctgcg tggtggtgga tgtgtctcaa    900

gaggaccctg aggtgcagtt caattggtac gtggacggcg tggaagtgca caacgccaag    960

accaagccta gagaggaaca gttcaactcc acctatagag tggtgtccgt gctgaccgtg   1020

ctgcaccagg attggctgaa cggcaaagag tacaagtgca aggtgtccaa caagggcctg   1080
```

-continued

```
ccttccagca tcgaaaagac catcagcaag gctaagggcc agcctaggga accccaggtt   1140

tacaccctgc ctccaagcca agaggaaatg accaagaacc aggtgtccct gacctgcctg   1200

gtcaagggct tctacccttc cgacattgcc gtggaatggg agtccaatgg ccagcctgag   1260

aacaactaca agaccacacc tcctgtgctg gactccgacg gctccttctt tctgtactct   1320

cgcctgaccg tggacaagtc taggtggcaa gagggcaacg tgttctcctg ctctgtgctg   1380

cacgaggctc tgcacaacca ctacacccag aagtccctgt ctctgtctct tggaggtggt   1440

ggcggttctg cccctacctc cagctctacc aagaaaaccc agctccagtt ggagcatctg   1500

ctgctggacc tccagatgat cctgaatggc atcaacaatt acaagaaccc caagctgacc   1560

gccatgctga ccgctaagtt ctacatgccc aagaaggcca ccgagctgaa gcacttgcag   1620

tgcctggaaa gggaactgaa gcccctggaa gaagtgctga atctggccca gtccaagaac   1680

ttccacctga ggcctaggga cctgatctcc aacatcaacg tgatcgtgct ggaactgaaa   1740

ggctccgaga caaccttcat gtgcgagtac gccgacgaga cagccaccat cgtggaattt   1800

ctgaaccggt ggatcacctt ctgccagagc atcatctcca cactgacc               1848
```

<210> SEQ ID NO 34
<211> LENGTH: 616
<212> TYPE: PRT
<213> ORGANISM: Artificial Sequence
<220> FEATURE:
<223> OTHER INFORMATION: fusion protein (mGI102-M61)

<400> SEQUENCE: 34

```
Met Asp Ala Met Leu Arg Gly Leu Cys Cys Val Leu Leu Leu Cys Gly
1               5                   10                  15

Ala Val Phe Val Ser Pro Ser His Ala Val Asp Glu Gln Leu Ser Lys
            20                  25                  30

Ser Val Lys Asp Lys Val Leu Leu Pro Cys Arg Tyr Asn Ser Pro His
        35                  40                  45

Glu Asp Glu Ser Glu Asp Arg Ile Tyr Trp Gln Lys His Asp Lys Val
    50                  55                  60

Val Leu Ser Val Ile Ala Gly Lys Leu Lys Val Trp Pro Glu Tyr Lys
65                  70                  75                  80

Asn Arg Thr Leu Tyr Asp Asn Thr Thr Tyr Ser Leu Ile Ile Leu Gly
                85                  90                  95

Leu Val Leu Ser Asp Arg Gly Thr Tyr Ser Cys Val Val Gln Lys Lys
            100                 105                 110

Glu Arg Gly Thr Tyr Glu Val Lys His Leu Ala Leu Val Lys Leu Ser
        115                 120                 125

Ile Lys Ala Asp Phe Ser Thr Pro Asn Ile Thr Glu Ser Gly Asn Pro
    130                 135                 140

Ser Ala Asp Thr Lys Arg Ile Thr Cys Phe Ala Ser Gly Gly Phe Pro
145                 150                 155                 160

Lys Pro Arg Phe Ser Trp Leu Glu Asn Gly Arg Glu Leu Pro Gly Ile
                165                 170                 175

Asn Thr Thr Ile Ser Gln Asp Pro Glu Ser Glu Leu Tyr Thr Ile Ser
            180                 185                 190

Ser Gln Leu Asp Phe Asn Thr Thr Arg Asn His Thr Ile Lys Cys Leu
        195                 200                 205

Ile Lys Tyr Gly Asp Ala His Val Ser Glu Asp Phe Thr Trp Glu Lys
    210                 215                 220

Pro Pro Glu Asp Pro Pro Asp Ser Gly Ser Gly Gly Gly Gly Ser Gly
```

```
225                 230                 235                 240

Gly Gly Gly Ser Gly Gly Gly Gly Ser Ala Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Gly Gly
465                 470                 475                 480

Gly Gly Ser Ala Pro Thr Ser Ser Ser Thr Lys Lys Thr Gln Leu Gln
                485                 490                 495

Leu Glu His Leu Leu Leu Asp Leu Gln Met Ile Leu Asn Gly Ile Asn
            500                 505                 510

Asn Tyr Lys Asn Pro Lys Leu Thr Ala Met Leu Thr Ala Lys Phe Tyr
        515                 520                 525

Met Pro Lys Lys Ala Thr Glu Leu Lys His Leu Gln Cys Leu Glu Arg
    530                 535                 540

Glu Leu Lys Pro Leu Glu Glu Val Leu Asn Leu Ala Gln Ser Lys Asn
545                 550                 555                 560

Phe His Leu Arg Pro Arg Asp Leu Ile Ser Asn Ile Asn Val Ile Val
                565                 570                 575

Leu Glu Leu Lys Gly Ser Glu Thr Thr Phe Met Cys Glu Tyr Ala Asp
            580                 585                 590

Glu Thr Ala Thr Ile Val Glu Phe Leu Asn Arg Trp Ile Thr Phe Cys
        595                 600                 605

Gln Ser Ile Ile Ser Thr Leu Thr
    610                 615

<210> SEQ ID NO 35
<211> LENGTH: 153
<212> TYPE: PRT
<213> ORGANISM: Artificial Sequence
```

<220> FEATURE:
<223> OTHER INFORMATION: wild type hIL-2

<400> SEQUENCE: 35

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 36
<211> LENGTH: 158
<212> TYPE: PRT
<213> ORGANISM: Artificial Sequence
<220> FEATURE:
<223> OTHER INFORMATION: IL-2 with signal sequence

<400> SEQUENCE: 36

```
Met Asp Ala Met Leu Arg Gly Leu Cys Cys Val Leu Leu Leu Cys Gly
1               5                   10                  15

Ala Val Phe Val Ser Pro Ser His Ala Ala Pro Thr Ser Ser Ser Thr
            20                  25                  30

Lys Lys Thr Gln Leu Gln Leu Glu His Leu Leu Leu Asp Leu Gln Met
        35                  40                  45

Ile Leu Asn Gly Ile Asn Asn Tyr Lys Asn Pro Lys Leu Thr Arg Met
    50                  55                  60

Leu Thr Phe Lys Phe Tyr Met Pro Lys Lys Ala Thr Glu Leu Lys His
65                  70                  75                  80

Leu Gln Cys Leu Glu Glu Glu Leu Lys Pro Leu Glu Glu Val Leu Asn
                85                  90                  95

Leu Ala Gln Ser Lys Asn Phe His Leu Arg Pro Arg Asp Leu Ile Ser
            100                 105                 110

Asn Ile Asn Val Ile Val Leu Glu Leu Lys Gly Ser Glu Thr Thr Phe
        115                 120                 125

Met Cys Glu Tyr Ala Asp Glu Thr Ala Thr Ile Val Glu Phe Leu Asn
    130                 135                 140

Arg Trp Ile Thr Phe Cys Gln Ser Ile Ile Ser Thr Leu Thr
145                 150                 155
```

<210> SEQ ID NO 37
<211> LENGTH: 474
<212> TYPE: DNA

<213> ORGANISM: Artificial Sequence
<220> FEATURE:
<223> OTHER INFORMATION: nucleotide sequence coding IL-2 with signal sequence

<400> SEQUENCE: 37

```
atggatgcta tgctgagagg cctgtgttgc gtgctgctgc tgtgtggcgc tgtgttcgtg     60

tctccttctc acgctgcccc taccagctcc tctaccaaga aaacccagct ccagttggag    120

catctgctgc tggacctcca gatgattctg aacgggatca acaactataa gaaccccaag    180

ctgacccgca tgctgacctt taagttctac atgcccaaga aggccaccga gctgaagcac    240

ctccagtgcc tggaagaaga actgaagccc ctggaagagg tgctgaatct ggcccagtcc    300

aagaacttcc acctgaggcc acgggacctg atcagcaaca tcaacgtgat cgtgctggaa    360

ctgaagggct ccgagacaac ctttatgtgc gagtacgccg acgagacagc caccatcgtg    420

gaatttctga accggtggat caccttctgc cagagcatca tctccacact gacc          474
```

<210> SEQ ID NO 38
<211> LENGTH: 13
<212> TYPE: PRT
<213> ORGANISM: Artificial Sequence
<220> FEATURE:
<223> OTHER INFORMATION: hinge

<400> SEQUENCE: 38

```
Ala Glu Ser Lys Tyr Gly Pro Pro Cys Pro Pro Cys Pro
1               5                   10
```

<210> SEQ ID NO 39
<211> LENGTH: 1461
<212> TYPE: DNA
<213> ORGANISM: Artificial Sequence
<220> FEATURE:
<223> OTHER INFORMATION: nucleotides coding CD80-Fc protein

<400> SEQUENCE: 39

```
ggatccgcca ccatggatgc tatgctgaga ggcctgtgtt gcgtgctgct gctgtgtggc     60

gctgtgttcg tgtctccttc tcacgctgtg atccacgtga ccaaagaagt gaaagaggtc    120

gccacactgt cctgcggcca caacgtttca gtggaagaac tggcccagac caggatctac    180

tggcagaaag aaaagaaaat ggtgctgacc atgatgtccg gcgacatgaa catctggcct    240

gagtacaaga accggaccat cttcgacatc accaacaacc tgtccatcgt gattctggcc    300

ctgaggcctt ctgatgaggg cacctatgag tgcgtggtgc tgaagtacga gaaggacgcc    360

ttcaagcgcg agcacctggc tgaagtgaca ctgtccgtga aggccgactt tcccacacct    420

tccatctccg acttcgagat ccctacctcc aacatccggc ggatcatctg ttctacctct    480

ggcggctttc ctgagcctca cctgtcttgg ctggaaaacg gcgaggaact gaacgccatc    540

aacaccaccg tgtctcagga ccccgaaacc gagctgtacg ctgtgtcctc caagctggac    600

ttcaacatga ccaccaacca cagcttcatg tgcctgatta agtacggcca cctgagagtg    660

aaccagacct tcaactggaa caccaccaag caagagcact tccctgacaa tggatctggc    720

ggcggaggtt ctggcggagg tggaagcgga ggcggaggat ctgctgagtc taagtatggc    780

cctccttgtc ctccatgtcc tgctccagaa gctgctggcg gaccctctgt gttcctgttt    840

cctccaaagc ctaaggacca gctcatgatc tctcggacac ccgaagtgac ctgcgtggtg    900

gtggatgtgt ctcaagagga ccctgaggtg cagttcaatt ggtacgtgga cggcgtggaa    960

gtgcacaacg ccaagaccaa gcctagagag gaacagttca actccaccta cagagtggtg   1020
```

```
tccgtgctga ccgtgctgca ccaggattgg ctgaacggca aagagtacaa gtgcaaggtg   1080

tccaacaagg gcctgccttc cagcatcgaa aagaccatct ccaaggctaa gggccagcct   1140

agggaacccc aggtttacac cctgcctcca agccaagagg aaatgaccaa gaaccaggtg   1200

tccctgacct gcctggtcaa gggcttctac ccttccgaca ttgccgtgga atgggagtcc   1260

aatggccagc ctgagaacaa ctacaagacc acacctcctg tgctggactc cgacggctcc   1320

ttctttctgt actctcgcct gaccgtggac aagtctaggt ggcaagaggg caacgtgttc   1380

tcctgctctg tgctgcacga ggccctgcac aatcactaca cccagaagtc cctgtctctg   1440

tccctgggct gatgactcga g                                             1461


<210> SEQ ID NO 40
<211> LENGTH: 479
<212> TYPE: PRT
<213> ORGANISM: Artificial Sequence
<220> FEATURE:
<223> OTHER INFORMATION: CD80-Fc protein

<400> SEQUENCE: 40

Met Asp Ala Met Leu Arg Gly Leu Cys Cys Val Leu Leu Leu Cys Gly
1               5                   10                  15

Ala Val Phe Val Ser Pro Ser His Ala Val Ile His Val Thr Lys Glu
            20                  25                  30

Val Lys Glu Val Ala Thr Leu Ser Cys Gly His Asn Val Ser Val Glu
        35                  40                  45

Glu Leu Ala Gln Thr Arg Ile Tyr Trp Gln Lys Glu Lys Lys Met Val
    50                  55                  60

Leu Thr Met Met Ser Gly Asp Met Asn Ile Trp Pro Glu Tyr Lys Asn
65                  70                  75                  80

Arg Thr Ile Phe Asp Ile Thr Asn Asn Leu Ser Ile Val Ile Leu Ala
                85                  90                  95

Leu Arg Pro Ser Asp Glu Gly Thr Tyr Glu Cys Val Val Leu Lys Tyr
            100                 105                 110

Glu Lys Asp Ala Phe Lys Arg Glu His Leu Ala Glu Val Thr Leu Ser
        115                 120                 125

Val Lys Ala Asp Phe Pro Thr Pro Ser Ile Ser Asp Phe Glu Ile Pro
    130                 135                 140

Thr Ser Asn Ile Arg Arg Ile Ile Cys Ser Thr Ser Gly Gly Phe Pro
145                 150                 155                 160

Glu Pro His Leu Ser Trp Leu Glu Asn Gly Glu Glu Leu Asn Ala Ile
                165                 170                 175

Asn Thr Thr Val Ser Gln Asp Pro Glu Thr Glu Leu Tyr Ala Val Ser
            180                 185                 190

Ser Lys Leu Asp Phe Asn Met Thr Thr Asn His Ser Phe Met Cys Leu
        195                 200                 205

Ile Lys Tyr Gly His Leu Arg Val Asn Gln Thr Phe Asn Trp Asn Thr
    210                 215                 220

Thr Lys Gln Glu His Phe Pro Asp Asn Gly Ser Gly Gly Gly Gly Ser
225                 230                 235                 240

Gly Gly Gly Gly Ser Gly Gly Gly Gly Ser Ala Glu Ser Lys Tyr Gly
                245                 250                 255

Pro Pro Cys Pro Pro Cys Pro Ala Pro Glu Ala Ala Gly Gly Pro Ser
            260                 265                 270

Val Phe Leu Phe Pro Pro Lys Pro Lys Asp Gln Leu Met Ile Ser Arg
```

```
        275                 280                 285

Thr Pro Glu Val Thr Cys Val Val Val Asp Val Ser Gln Glu Asp Pro
    290                 295                 300

Glu Val Gln Phe Asn Trp Tyr Val Asp Gly Val Glu Val His Asn Ala
305                 310                 315                 320

Lys Thr Lys Pro Arg Glu Glu Gln Phe Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Gly Leu Pro Ser Ser Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Gln Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Arg Leu Thr Val Asp Lys Ser
        435                 440                 445

Arg Trp Gln Glu Gly Asn Val Phe Ser Cys Ser Val Leu His Glu Ala
    450                 455                 460

Leu His Asn His Tyr Thr Gln Lys Ser Leu Ser Leu Ser Leu Gly
465                 470                 475
```

<210> SEQ ID NO 41
<211> LENGTH: 1851
<212> TYPE: DNA
<213> ORGANISM: Artificial Sequence
<220> FEATURE:
<223> OTHER INFORMATION: nucleotides coding fusion protein (hCD80-Fc-IL2wt)

<400> SEQUENCE: 41

```
atggatgcta tgctgagagg cctgtgttgc gtgctgctgc tgtgtggcgc tgtgttcgtg     60

tctccttctc acgctgtgat ccacgtgacc aaagaagtga aagaggtcgc cacactgtcc    120

tgcggccaca acgtttcagt ggaagaactg gcccagacca ggatctactg gcagaaagaa    180

aagaaaatgg tgctgaccat gatgtccggc gacatgaaca tctggcctga gtacaagaac    240

cggaccatct tcgacatcac caacaacctg tccatcgtga ttctggccct gaggccttct    300

gatgagggca cctatgagtg cgtggtgctg aagtacgaga aggacgcctt caagcgcgag    360

cacctggctg aagtgacact gtccgtgaag gccgactttc ccacaccttc catctccgac    420

ttcgagatcc ctacctccaa catccggcgg atcatctgtt ctacctctgg cggctttcct    480

gagcctcacc tgtcttggct ggaaaacggc gaggaactga acgccatcaa caccaccgtg    540

tctcaggacc ccgaaaccga gctgtacgct gtgtcctcca agctggactt caacatgacc    600

accaaccaca gcttcatgtg cctgattaag tacggccacc tgagagtgaa ccagaccttc    660

aactggaaca ccaccaagca agagcacttc cctgacaatg gatctggcgg cggaggttct    720

ggcggaggtg gaagcggagg cggaggatct gctgagtcta agtatggccc tccttgtcct    780

ccatgtcctg ctccagaagc tgctggcgga ccctctgtgt tcctgtttcc tccaaagcct    840

aaggaccagc tcatgatctc tcggacaccc gaagtgacct gcgtggtggt ggatgtgtct    900
```

```
caagaggacc ctgaggtgca gttcaattgg tacgtggacg gcgtggaagt gcacaacgcc    960

aagaccaagc ctagagagga acagttcaac tccacctaca gagtggtgtc cgtgctgacc   1020

gtgctgcacc aggattggct gaacggcaaa gagtacaagt gcaaggtgtc caacaagggc   1080

ctgccttcca gcatcgaaaa gaccatctcc aaggctaagg gccagcctag ggaaccccag   1140

gtttacaccc tgcctccaag ccaagaggaa atgaccaaga accaggtgtc cctgacctgc   1200

ctggtcaagg gcttctaccc ttccgacatt gccgtggaat gggagtccaa tggccagcct   1260

gagaacaact acaagaccac acctcctgtg ctggactccg acggctcctt ctttctgtac   1320

tctcgcctga ccgtggacaa gtctagatgg caagagggca acgtgttctc ctgctctgtg   1380

ctgcacgagg ccctgcacaa tcactacacc cagaagtccc tgtctctgtc tcttggaggt   1440

ggtggcggtt ctgcccctac cagctcctct accaagaaaa cccagctcca gttggagcat   1500

ctgctgctgg acctccagat gattctgaac gggatcaaca actataagaa ccccaagctg   1560

acccgcatgc tgacctttaa gttctacatg cccaagaagg ccaccgagct gaagcacctc   1620

cagtgcctgg aagaagaact gaagcccctg gaagaggtgc tgaatctggc ccagtccaag   1680

aacttccacc tgaggccacg ggacctgatc agcaacatca acgtgatcgt gctggaactg   1740

aagggctccg agacaacctt tatgtgcgag tacgccgacg agacagccac catcgtggaa   1800

tttctgaacc ggtggatcac cttctgccag agcatcatct ccacactgac c             1851


<210> SEQ ID NO 42
<211> LENGTH: 367
<212> TYPE: PRT
<213> ORGANISM: Artificial Sequence
<220> FEATURE:
<223> OTHER INFORMATION: Fc-IL2wt

<400> SEQUENCE: 42

Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
```

```
        195                 200                 205

Ser Val Leu His Glu Ala Leu His Asn His Tyr Thr Gln Lys Ser Leu
    210                 215                 220

Ser Leu Ser Leu Gly Gly Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Cys Gln Ser Ile Ile Ser Thr Leu Thr
        355                 360                 365
```

<210> SEQ ID NO 43
<211> LENGTH: 1176
<212> TYPE: DNA
<213> ORGANISM: Artificial Sequence
<220> FEATURE:
<223> OTHER INFORMATION: Fc-IL2wt

<400> SEQUENCE: 43

```
atggatgcta tgctgagagg cctgtgttgc gtgctgctgc tgtgtggcgc tgtgttcgtg      60

tctccttctc acgctgctga gtctaagtat ggccctcctt gtcctccatg tcctgctcca     120

gaagctgctg gcggaccctc tgtgttcctg tttcctccaa agcctaagga ccagctcatg     180

atctctcgga cacccgaagt gacctgcgtg gtggtggatg tgtctcaaga ggaccctgag     240

gtgcagttca attggtacgt ggacggcgtg gaagtgcaca acgccaagac caagcctaga     300

gaggaacagt tcaactccac ctacagagtg gtgtccgtgc tgaccgtgct gcaccaggat     360

tggctgaacg gcaaagagta caagtgcaag gtgtccaaca agggcctgcc ttccagcatc     420

gaaaagacca tctccaaggc taagggccag cctagggaac cccaggttta caccctgcct     480

ccaagccaag aggaaatgac caagaaccag gtgtccctga cctgcctggt caagggcttc     540

taccctteccg acattgccgt ggaatgggag tccaatggcc agcctgagaa caactacaag     600

accacacctc ctgtgctgga ctccgacggc tccttctttc tgtactctcg cctgaccgtg     660

gacaagtcta gatggcaaga gggcaacgtg ttctcctgct ctgtgctgca cgaggccctg     720

cacaatcact acacccagaa gtccctgtct ctgtctcttg gaggtggtgg cggttctgcc     780

cctaccagct cctctaccaa gaaaacccag ctccagttgg agcatctgct gctggacctc     840

cagatgattc tgaacgggat caacaactat aagaacccca agctgacccg catgctgacc     900

tttaagttct acatgcccaa gaaggccacc gagctgaagc acctccagtg cctggaagaa     960

gaactgaagc ccctggaaga ggtgctgaat ctggcccagt ccaagaactt ccacctgagg    1020

ccacgggacc tgatcagcaa catcaacgtg atcgtgctgg aactgaaggg ctccgagaca    1080

acctttatgt gcgagtacgc cgacgagaca gccaccatcg tggaatttct gaaccggtgg    1140
```

```
atcaccttct gccagagcat catctccaca ctgacc                           1176


<210> SEQ ID NO 44
<211> LENGTH: 392
<212> TYPE: PRT
<213> ORGANISM: Artificial Sequence
<220> FEATURE:
<223> OTHER INFORMATION: Fc-IL2v2

<400> SEQUENCE: 44

Met Asp Ala Met Leu Arg Gly Leu Cys Cys Val Leu Leu Leu Cys Gly
1               5                   10                  15

Ala Val Phe Val Ser Pro Ser His Ala Ala Glu Ser Lys Tyr Gly Pro
            20                  25                  30

Pro Cys Pro Pro Cys Pro Ala Pro Glu Ala Ala Gly Gly Pro Ser Val
        35                  40                  45

Phe Leu Phe Pro Pro Lys Pro Lys Asp Gln Leu Met Ile Ser Arg Thr
    50                  55                  60

Pro Glu Val Thr Cys Val Val Val Asp Val Ser Gln Glu Asp Pro Glu
65                  70                  75                  80

Val Gln Phe Asn Trp Tyr Val Asp Gly Val Glu Val His Asn Ala Lys
                85                  90                  95

Thr Lys Pro Arg Glu Glu Gln Phe Asn Ser Thr Tyr Arg Val Val Ser
            100                 105                 110

Val Leu Thr Val Leu His Gln Asp Trp Leu Asn Gly Lys Glu Tyr Lys
        115                 120                 125

Cys Lys Val Ser Asn Lys Gly Leu Pro Ser Ser Ile Glu Lys Thr Ile
    130                 135                 140

Ser Lys Ala Lys Gly Gln Pro Arg Glu Pro Gln Val Tyr Thr Leu Pro
145                 150                 155                 160

Pro Ser Gln Glu Glu Met Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Arg Leu Thr Val Asp Lys Ser Arg
    210                 215                 220

Trp Gln Glu Gly Asn Val Phe Ser Cys Ser Val Leu His Glu Ala Leu
225                 230                 235                 240

His Asn His Tyr Thr Gln Lys Ser Leu Ser Leu Ser Leu Gly Gly Gly
                245                 250                 255

Gly Gly Ser Ala Pro Thr Ser Ser Ser Thr Lys Lys Thr Gln Leu Gln
            260                 265                 270

Leu Glu His Leu Leu Leu Asp Leu Gln Met Ile Leu Asn Gly Ile Asn
        275                 280                 285

Asn Tyr Lys Asn Pro Lys Leu Thr Ala Met Leu Thr Ala Lys Phe Tyr
    290                 295                 300

Met Pro Lys Lys Ala Thr Glu Leu Lys His Leu Gln Cys Leu Glu Glu
305                 310                 315                 320

Glu Leu Lys Pro Leu Glu Glu Val Leu Asn Leu Ala Gln Ser Lys Asn
                325                 330                 335

Phe His Leu Arg Pro Arg Asp Leu Ile Ser Asn Ile Asn Val Ile Val
            340                 345                 350
```

```
Leu Glu Leu Lys Gly Ser Glu Thr Thr Phe Met Cys Glu Tyr Ala Asp
        355                 360                 365

Glu Thr Ala Thr Ile Val Glu Phe Leu Asn Arg Trp Ile Thr Phe Cys
    370                 375                 380

Gln Ser Ile Ile Ser Thr Leu Thr
385                 390


<210> SEQ ID NO 45
<211> LENGTH: 1200
<212> TYPE: DNA
<213> ORGANISM: Artificial Sequence
<220> FEATURE:
<223> OTHER INFORMATION: nucleotides coding Fc-IL2v2

<400> SEQUENCE: 45

ggatccgcca ccatggatgc tatgctgaga ggcctgtgtt gcgtgctgct gctgtgtggc      60

gctgtgttcg tgtctccatc tcacgccgct gagtctaagt acggccctcc ttgtcctcca     120

tgtcctgctc cagaagctgc tggcggaccc tctgtgttcc tgtttcctcc aaagcctaag     180

gaccagctca tgatctctcg gacccctgaa gtgacctgcg tggtggtgga tgtgtctcaa     240

gaggaccctg aggtgcagtt caattggtac gtggacggcg tggaagtgca caacgccaag     300

accaagccta gagaggaaca gttcaactcc acctacagag tggtgtccgt gctgaccgtg     360

ctgcaccagg attggctgaa cggcaaagag tacaagtgca aggtgtccaa caagggcctg     420

ccttccagca tcgaaaagac catctccaag gctaagggcc agcctaggga accccaggtt     480

tacaccctgc ctccaagcca agaggaaatg accaagaacc aggtgtccct gacctgcctg     540

gtcaagggct tctacccttc cgacattgcc gtggaatggg agtccaatgg ccagcctgag     600

aacaactaca agaccacacc tcctgtgctg gactccgacg gctccttctt tctgtactct     660

cgcctgaccg tggacaagtc taggtggcaa gagggcaacg tgttctcctg ctctgtgctg     720

cacgaggccc tgcacaatca ctacacccag aagtccctgt ctctgtctct tggcggaggc     780

ggaggatctg ctcctacctc cagctccacc aagaaaaccc agctccagtt ggagcatctg     840

ctgctggacc tccagatgat cctgaatggc atcaacaatt acaagaaccc caagctgacc     900

gccatgctga ccgctaagtt ctacatgccc aagaaggcca ccgagctgaa gcacctccag     960

tgcctggaag aggaactgaa gcccctggaa gaagtgctga atctggccca gtccaagaac    1020

ttccacctga ggcctaggga cctgatctcc aacatcaacg tgatcgtgct ggaactgaaa    1080

ggctccgaga caaccttcat gtgcgagtac gccgacgaga cagccaccat cgtggaattt    1140

ctgaaccggt ggatcacctt ctgccagtcc atcatctcca cactgacctg atgactcgag    1200


<210> SEQ ID NO 46
<211> LENGTH: 592
<212> TYPE: PRT
<213> ORGANISM: Artificial Sequence
<220> FEATURE:
<223> OTHER INFORMATION: CD80-Fc-IL2wt

<400> SEQUENCE: 46

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
```

```
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Gly Ser Gly Gly Gly Gly Ser Gly Gly Gly Gly Ser Gly Gly Gly Gly
    210                 215                 220

Ser Ala Glu Ser Lys Tyr Gly Pro Pro Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Gln Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Leu His Glu Ala Leu His Asn His Tyr Thr Gln Lys Ser
        435                 440                 445

Leu Ser Leu Ser Leu Gly Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480
```

-continued

```
Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Cys Gln Ser Ile Ile Ser Thr Leu Thr
            580                 585                 590
```

COMPOSITION FOR CULTURING NATURAL KILLER CELLS AND METHOD FOR PREPARING NATURAL KILLER CELLS BY USING SAME

CROSS-REFERENCE TO RELATED APPLICATIONS

This is a Continuation under 35 USC § 120 and 35 USC § 365(c) of International Patent Application No. PCT/KR2020/016376 filed Nov. 19, 2020, and claims priority under 35 USC § 119 of Korean Patent Application No. 10-2019-0149779 filed Nov. 20, 2019 and Korean Patent Application No. 10-2020-0015802 filed Feb. 10, 2020. The disclosures of all such applications are hereby incorporated herein by reference in their respective entireties, for all purposes.

JOINT RESEARCH AGREEMENT

The claimed invention hereof was made as a result of activities undertaken within the scope of a joint research agreement between GI CELL, INC. and GI INNOVATION, INC. that was in effect prior to the date the invention was made.

REFERENCE TO SEQUENCE LISTING SUBMITTED VIA EFS

This application includes an electronically submitted sequence listing in .txt format. The .txt file contains a sequence listing entitled "632_SegListing_ST25.txt" created on May 8, 2022 and is 123,294 bytes in size. The sequence listing contained in this .txt file is part of the specification and is hereby incorporated by reference herein in its entirety.

TECHNICAL FIELD

The present invention relates to a composition for culturing natural killer cells and a method for producing natural killer cells using the same.

BACKGROUND ART

Various treatments such as surgical operation, radiation therapy, and chemotherapy have been developed to treat cancer, but as several side effects have been reported, immunotherapy using immune function of a patient has been recently developed. In particular, immunotherapy using natural killer cells which can undergo large-scale production and freezing has been studied.

Specifically, natural killer cells are a type of lymphocyte that are distributed in bone marrow, spleen, peripheral lymph nodes and peripheral blood of the body. They make up about 10% of peripheral blood lymphocytes, and play an important role in innate immune response (Ann Rev Immunol., 24: 257-286, 2006)). In addition, natural killer cells are positive for CD56 and CD16, but negative for CD3. Natural killer cells kill cells by release of cytoplasmic granules containing perforin and granzyme. Natural killer cells secrete various cytokines such as IFN-γ, TNF-α, GM-CSF and IL-10.

In addition, natural killer cells express several receptors on the cell surface, and these receptors are involved in cell adhesion, activation of capacity to kill cells, or inhibition of capacity to kill cells. However, most natural killer cells in the body of a normal subject exist in an inactive state. Therefore, there is a need for activated natural killer cells to eliminate cancer. In addition, for natural killer cells present in the body of a cancer patient, natural killer cells have functional defects due to immune evasion mechanism of cancer cells. Therefore, it is very important to activate natural killer cells to use natural killer cells as a therapeutic agent. Further, it is essential to develop a technique to massively proliferate and freeze natural killer cells in blood from a normal subject or a patient because the number of natural killer cells present in the body is limited.

Meanwhile, IL-2, also called as T-cell growth factor (TCGF), is a globular glycoprotein that plays a central role in production, survival, and homeostasis of lymphocyte. IL-2 has a size of 15.5 kDa to 16 kDa protein and consists of 133 amino acids. IL-2 mediates various immune responses by binding to the IL-2 receptor which has three distinct subunits.

In addition, CD80 is known as B7-1 and one of B7 family members among membrane-bound proteins involved in immune regulation by binding to the ligand and thus transmitting costimulatory responses and coinhibitory responses. CD80 is a transmembrane protein expressed on the surface of T cells, B cells, dendritic cells, and monocytes. CD80 is known to bind to CD28, CTLA4 (CD152), and PD-L1. As such, it is widely known that natural killer cells are important for anti cancer treatment, but specific methods that can amplify natural killer cells to use them effectively are still insufficient.

DETAILED DESCRIPTION OF THE INVENTION

Technical Problem

Accordingly, the present inventors prepared natural killer cells by using a fusion protein dimer comprising IL-2 protein and CD80 protein, as a result of researching to prepare activated natural killer cells in a large amount. In addition, the present inventors have identified that natural killer cells thus prepared has increased activity and exhibits excellent anticancer effects, and thus have completed the present invention.

Solution to Problem

To achieve the above object, in accordance with an exemplary embodiment, provided is a composition for culturing natural killer cells including, as an active ingredient, a fusion protein dimer comprising IL-2 or a variant thereof and CD80 or a fragment thereof.

In accordance with another exemplary embodiment, provided is a method for culturing natural killer cells including: i) isolating cells that do not express CD3 from peripheral blood mononuclear cells (PBMC); ii) isolating cells that express CD56 from the cells that do not express CD3, isolated in the above step; and iii) culturing the isolated cells in the presence of a fusion protein dimer comprising IL-2 or a variant thereof and CD80 or a fragment thereof.

In accordance with yet another exemplary embodiment, provided is natural killer cells prepared by the method for culturing natural killer cells.

In accordance with still another exemplary embodiment, provided is a pharmaceutical composition for preventing or treating cancer including the natural killer cells as an active ingredient.

In accordance with yet still another exemplary embodiment, provided is a method for culturing natural killer cells including: i) isolating cells that do not express CD3 from PBMCs; and ii) culturing the isolated cells in the presence of a fusion protein dimer comprising IL-2 or a variant thereof and CD80 or a fragment thereof.

In accordance with another exemplary embodiment, provided is natural killer cells prepared by the method for culturing natural killer cells.

In accordance with yet another exemplary embodiment, provided is a pharmaceutical composition for preventing or treating cancer including the natural killer cells as an active ingredient.

In accordance with still another exemplary embodiment, provided is a method for culturing natural killer cells including: i) isolating cells that express CD56 from PBMCs; and ii) culturing the isolated cells in the presence of a fusion protein dimer comprising IL-2 or a variant thereof and CD80 or a fragment thereof.

In accordance with yet still another exemplary embodiment, provided is natural killer cells prepared by the method for culturing natural killer cells.

In accordance with another exemplary embodiment, provided is a pharmaceutical composition for preventing or treating cancer including the natural killer cells as an active ingredient.

In accordance with yet another exemplary embodiment, provided is a method for promoting the activity of natural killer cells in PBMCs including culturing PBMCs in the presence of a fusion protein dimer comprising IL-2 or a variant thereof and CD80 or a fragment thereof.

In accordance with still another exemplary embodiment, provided are PBMCs prepared by the method for promoting the activity of natural killer cells in the PBMCs.

In accordance with yet still another exemplary embodiment, provided is a pharmaceutical composition for preventing or treating cancer including the PBMCs as an active ingredient.

Effect of the Invention

The composition of the present invention for culturing natural killer cells including, as an active ingredient, a fusion protein comprising IL-2 or a variant thereof and CD80 or a fragment thereof promotes proliferation of natural killer cells, induces expression of CD16 and NKp46, and increases expression and secretion of granzyme B and perforin, and thus may be usefully used in the production of natural killer cells having excellent anticancer immune function.

BRIEF DESCRIPTION OF DRAWINGS

Exemplary embodiments can be understood in more detail from the following description taken in conjunction with the accompanying drawings, in which.

BEST MODE FOR CARRYING OUT THE INVENTION

Figure 1A:
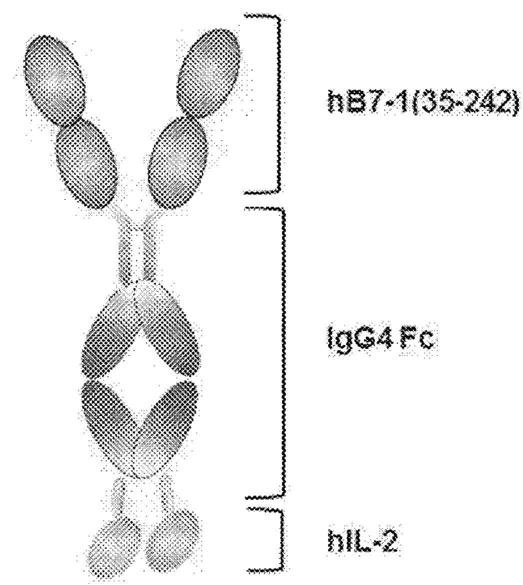
FIG. 1A is a schematic diagram of a fusion protein dimer used in the present invention.

Composition and Medium for NK Cell Proliferation

An aspect of the present invention provides a composition for culturing a natural killer (NK) cell including, as an active ingredient, a fusion protein dimer comprising IL-2 or a variant thereof and CD80 or a fragment thereof. In addition, a natural killer cell culture medium including the fusion protein dimer as an active ingredient is provided.

The composition for culturing the natural killer cell may further include any one selected from the group consisting of a medium, a serum, a supplement, and a combination thereof.

The NK cell culture medium may be a medium in which the fusion protein dimer comprising IL-2 protein and CD80 protein is added to a cell culture medium. In this case, the cell culture medium may include any one selected from the group consisting of amino acids, sugars, inorganic salts, and vitamins. Preferably, the cell culture medium may include all of amino acids, sugars, inorganic salts, and vitamins. As a specific embodiment, the NK cell culture medium may include at least one of components in Table 1 to Table 4 below.

As used herein, the term "cell culture medium" means a medium used for culturing cells, specifically NK cells, and more specifically CD3-CD56+ cells. This includes components required by cells for cell growth and survival in vitro, or includes components that help cell growth and survival. Specifically, the components may be vitamins, essential or non-essential amino acids, and trace elements. The medium may be a medium used for culturing cells, preferably eukaryotic cells, and more preferably NK cells.

The cell culture medium according to the present invention may include an amino acid component, a vitamin component, an inorganic salt component, other component, and purified water, wherein:

a) the amino acid component is at least one amino acid selected from the group consisting of glycine, L-alanine, L-valine, L-leucine, L-isoleucine, L-threonine, L-serine, L-cysteine, L-methionine, L-aspartic acid, L-asparagine, L-glutamic acid, L-glutamine, L-lysine, L-arginine, L-histidine, L-phenylalanine, L-tyrosine, L-tryptophan, L-proline, β-alanine, γ-aminobutyric acid, ornithine, citrulline, homoserine, triiodothyronine, thyroxine and dioxy phenylalanine, or a combination thereof, and preferably at least one amino acid selected from the group consisting of glycine, L-alanine, L-arginine, L-cysteine, L-glutamine, L-histidine, L-lysine, L-methionine, L-proline, L-serine, L-threonine and L-valine, or a combination thereof;

b) the vitamin component is at least one vitamin selected from the group consisting of biotin, calcium D-pantothenate, folic acid, niacinamide, pyridoxine hydrochloride, riboflavin, thiamine hydrochloride, vitamin B12, choline chloride, i-inositol and ascorbic acid, or a combination thereof, and preferably at least one vitamin selected from the group consisting of i-inositol, thiamine hydrochloride, niacinamide and pyridoxine hydrochloride, or a combination thereof;

c) the inorganic salt component is at least one inorganic salt selected from the group consisting of calcium chloride ($CaCl_2$)(anhydrous), copper sulfate pentahydrate ($CuSO_4$-$5H_2O$), iron (III) sulfate heptahydrate ($FeSO_4$-$7H_2O$), magnesium chloride (anhydrous), magnesium sulfate ($MgSO_4$)(anhydrous), potassium chloride (KCl), sodium chloride (NaCl), disodium hydrogen phosphate ($Na_2HPO_4$), sodium dihydrogen phosphate monohydrate ($NaH_2PO_4$—$H_2O$), zinc sulfate heptahydrate ($ZnSO_4$-$7H_2O$), iron (III) nitrate nonahydrate ($Fe(NO_3)_3 \cdot 9H_2O$) and sodium hydrogen carbonate ($NaHCO_3$), or a combination thereof, and preferably at least one inorganic salt selected from the group consisting of sodium chloride (NaCl), sodium hydrogen carbonate ($NaHCO_3$), potassium chloride (KCl), calcium chloride ($CaCl_2$)(anhydrous) and sodium dihydrogen phosphate monohydrate ($NaH_2PO_4$—$H_2O$), or a combination thereof;

d) the other component is at least one other component selected from the group consisting of D-glucose (dextrose), sodium pyruvate, hypoxanthine Na, thymidine, linoleic acid, lipoic acid, adenosine, cytidine, guanosine, uridine, 2'-deoxyadenosine, 2'-deoxycytidine HCl and 2'-deoxyguanosine, or a combination thereof, and it may preferably be sodium pyruvate; and e) the purified water is used to dissolve the amino acid, vitamin, inorganic salt, and other component, and may be obtained by one or more processes of distillation, or purified through a filter.

In addition, the cell culture medium according to the present invention may further include a growth factor or a cytokine. The growth factor may be IGF, bFGF, TGF, HGF, EGF, VEGF, PDGF, or the like alone or at least two thereof, but is not limited thereto. The cytokine may be IL-1, IL-4, IL-6, IFN-γ, IL-10, IL-15, IL-17, IL-21, or the like alone or at least two thereof, but is not limited thereto.

In addition, the cell culture medium according to the present invention may further include an antibody for activating natural killer cells. The antibody for activating natural killer cells may be an anti-CD3 antibody, an anti-CD2 antibody, an anti-CD335 antibody, or the like alone or at least two thereof, but is not limited thereto. In addition, a bead to which the antibody for activating natural killer cells is bound may be included. Also, a fusion protein including two or more types of antibodies or variable region fragments thereof for activating natural killer cells may be used.

In particular, the NK culture medium may further include any one selected from the group consisting of IL-15, IL-21, and a combination thereof.

The IL-15 and IL-21 may be a type of interleukin (IL), and mean proteinaceous bioactive substances produced by immunocompetent cells such as lymphocytes or monocytes and macrophages. The IL-15 and IL-21 may be used when culturing natural killer cells using mononuclear cells as source cells by promoting proliferation of natural killer cells, but there is a problem of low proliferation rate and purity when only these are used alone or in combination (Biossel L. et al., Biology of Blood and Marrow Transplantation, 14, 1031-1038, 2008).

Specifically, the medium may be a conventional medium for culturing animal cells, such as DMEM (Dulbecco's Modified Eagle's Medium), EDM (Endothelial differentiation medium), MEM (Minimal Essential Medium), BME (Basal Medium Eagle), RPMI 1640, F-10, F-12, a-MEM (a-Minimal Essential Medium), G-MEM (Glasgow's Minimal Essential Medium), Iscove's Modified Dulbecco's Medium, AIM-V Medium, X-VIVO™ 15 Medium, NK MACS Medium. In an embodiment of the present invention, AIM-V Medium, X-VIVO™ 15 Medium and NK MACS Medium were used as a medium.

The term "serum" as used in the present invention means clear supernatant separated from blood after the blood has been completely clotted. In addition, it is required to add serum to a synthetic medium for culturing animal cells, and it is common to use bovine, horse, or human serum. For bovine-derived serum, fetal bovine serum (FBS), newborn bovine serum, calf serum, bovine serum, or the like may be used depending on the timing of blood collection. For human-derived serum, human serum from a donor whose blood type is AB is used, and human AB serum which is free of antibodies to A and B blood type antigens so that can minimize immune reactivity may be used. In addition, CTS Immune Cell SR, or the like may be used as an alternative to the "serum." In an embodiment of the present invention, human AB serum or CTS Immune Cell SR was used.

GLUTAMAX (GIBCO®), a L-Glutamine alternative, may be used as the supplement to improve stability and cell activity during cell culture. In addition, the supplement may be NK MACS supplement (Miltenyi Biotec, 130-113-102).

Fusion Protein Dimer Comprising IL-2 Protein and CD80 Protein

As used herein, the term "IL-2" or "interleukin-2", unless otherwise stated, refers to any wild-type IL-2 obtained from any vertebrate source, including mammals, for example, primates (such as humans) and rodents (such as mice and rats). IL-2 may be obtained from animal cells, and also includes one obtained from recombinant cells capable of producing IL-2. In addition, IL-2 may be wild-type IL-2 or a variant thereof.

In the present specification, IL-2 or a variant thereof may be collectively expressed by the term "IL-2 protein" or "IL-2 polypeptide". IL-2, an IL-2 protein, an IL-2 polypeptide, and an IL-2 variant specifically bind to, for example, an IL-2 receptor. This specific binding may be identified by methods known to those skilled in the art.

An embodiment of IL-2 may have the amino acid sequence of SEQ ID NO: 35 or SEQ ID NO: 36. Here, IL-2 may also be in a mature form. Specifically, the mature IL-2 may not comprise a signal sequence, and may have the amino acid sequence of SEQ ID NO: 10. Here, IL-2 may be used under a concept encompassing a fragment of wild-type IL-2 in which a portion of N-terminus or C-terminus of the wild-type IL-2 is truncated.

In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from N-terminus of a protein having the amino acid sequence of SEQ ID NO: 35 or SEQ ID NO: 36. In addition, the fragment of IL-2 may be in a form in which 1, 2, 3, 4, 5, 6, 7, 8, 9, 10, 11, 12, 13, 14, 15, 16, 17, 18, 19, 20, 21, 22, 23, 24, or 25 contiguous amino acids are truncated from C-terminus of a protein having the amino acid sequence of SEQ ID NO: 35 or SEQ ID NO: 36.

As used herein, the term "IL-2 variant" refers to a form in which a portion of amino acids in the full-length IL-2 or the above-described fragment of IL-2 is substituted. That is, an IL-2 variant may have an amino acid sequence different from wild-type IL-2 or a fragment thereof. However, an IL-2 variant may have activity equivalent or similar to the wild-type IL-2. Here, "IL-2 activity" may, for example, refer to specific binding to an IL-2 receptor, which specific binding can be measured by methods known to those skilled in the art.

Specifically, an IL-2 variant may be obtained by substitution of a portion of amino acids in the wild-type IL-2. An embodiment of the IL-2 variant obtained by amino acid substitution may be obtained by substitution of at least one of the 38$^{th}$, 42$^{nd}$, 45$^{th}$, 61$^{st}$, and 72$^{nd}$ amino acids in the amino acid sequence of SEQ ID NO: 10. Specifically, the IL-2 variant may be obtained by substitution of at least one of the 38$^{th}$ 42$^{nd}$, 45$^{th}$, 61$^{st}$, or 72$^{nd}$ amino acid in the amino acid sequence of SEQ ID NO: 10 with another amino acid. In addition, when IL-2 is in a form in which a portion of N-terminus in the amino acid sequence of SEQ ID NO: 35 is truncated, the amino acid at a position complementarily corresponding to that in the amino acid sequence of SEQ ID NO: 10 may be substituted with another amino acid. For example, when IL-2 has the amino acid sequence of SEQ ID NO: 35, its IL-2 variant may be obtained by substitution of at least one of 58$^{th}$, 62$^{nd}$, 65$^{th}$ 81$^{st}$ or 92$^{nd}$ amino acid in the amino acid sequence of SEQ ID NO: 35 with another amino acid. These amino acid residues correspond to the respective 38$^{th}$, 42$^{nd}$, 45$^{th}$ 61$^{st}$ and 72$^{nd}$ amino acid residues in the amino acid sequence of SEQ ID NO: 10. According to an embodiment, one, two, three, four, five, six, seven, eight, nine, or ten amino acids may be substituted as long as such IL-2 variant maintains IL-2 activity. According to another embodiment, one to five amino acids may be substituted.

In an embodiment, an IL-2 variant may be in a form in which two amino acids are substituted. Specifically, the IL-2 variant may be obtained by substitution of the 38$^{th}$ and 42$^{nd}$ amino acids in the amino acid sequence of SEQ ID NO: 10. In addition, in an embodiment, the IL-2 variant may be obtained by substitution of the 38$^{th}$ and 45$^{th}$ amino acids in the amino acid sequence of SEQ ID NO: 10. In addition, in an embodiment, the IL-2 variant may be obtained by substitution of the 38$^{th}$ and 61$^{st}$ amino acids in the amino acid sequence of SEQ ID NO: 10. In addition, in an embodiment, the IL-2 variant may be obtained by substitution of the 38$^{th}$ and 72$^{nd}$ amino acids in the amino acid sequence of SEQ ID NO: 10. In addition, in an embodiment, the IL-2 variant may be obtained by substitution of the 42$^{nd}$ and 45$^{th}$ amino acids in the amino acid sequence of SEQ ID NO: 10. In addition, in an embodiment, the IL-2 variant may be obtained by substitution of the 42$^{nd}$ and 61$^{st}$ amino acids in the amino acid sequence of SEQ ID NO: 10. In addition, in an embodiment, the IL-2 variant may be obtained by substitution of the 42$^{nd}$ and 72$^{nd}$ amino acids in the amino acid sequence of SEQ ID NO: 10. In addition, in an embodiment, the IL-2 variant may be obtained by substitution of the 45$^{th}$ and 61$^{st}$ amino acids in the amino acid sequence of SEQ ID NO: 10. In addition, in an embodiment, the IL-2 variant may be obtained by substitution of the 45$^{th}$ and 72$^{nd}$ amino acids in the amino acid sequence of SEQ ID NO: 10. In addition, in an embodiment, the IL-2 variant may be obtained by substitution of the 61$^{st}$ and 72$^{nd}$ amino acids in the amino acid sequence of SEQ ID NO: 10.

Furthermore, an IL-2 variant may be in a form in which three amino acids are substituted. Specifically, the IL-2 variant may be obtained by substitution of the 38$^{th}$, 42$^{nd}$, and 45$^{th}$ amino acids in the amino acid sequence of SEQ ID NO: 10. In addition, in an embodiment, the IL-2 variant may be obtained by substitution of the 38$^{th}$, 42$^{nd}$, and 61$^{st}$ amino acids in the amino acid sequence of SEQ ID NO: 10. In addition, in an embodiment, the IL-2 variant may be obtained by substitution of the 38$^{th}$, 42$^{nd}$, and 72$^{nd}$ amino acids in the amino acid sequence of SEQ ID NO: 10. In addition, in an embodiment, the IL-2 variant may be obtained by substitution of the 38$^{th}$, 45$^{th}$, and 61$^{st}$ amino acids in the amino acid sequence of SEQ ID NO: 10. In addition, in an embodiment, the IL-2 variant may be obtained by substitution of the 38$^{th}$, 45$^{th}$, and 72$^{nd}$ amino acids in the amino acid sequence of SEQ ID NO: 10. In addition, in an embodiment, the IL-2 variant may be obtained by substitution of the 38$^{th}$, 61$^{st}$, and 72$^{nd}$ amino acids in the amino acid sequence of SEQ ID NO: 10. In addition, in an embodiment, the IL-2 variant may be obtained by substitution of the 42$^{nd}$, 45$^{th}$, and 61$^{st}$ amino acids in the amino acid sequence of SEQ ID NO: 10. In addition, in an embodiment, the IL-2 variant may be obtained by substitution of the 42$^{nd}$, 45$^{th}$, and 72$^{nd}$ amino acids in the amino acid sequence of SEQ ID NO: 10. In addition, in an embodiment, the IL-2 variant may be obtained by substitution of the 45$^{th}$, 61$^{st}$, and 72$^{nd}$ amino acids in the amino acid sequence of SEQ ID NO: 10. In addition, an IL-2 variant may be in a form in which four amino acids are substituted. Specifically, the IL-2 variant may be obtained by substitution of the 38$^{th}$, 42$^{nd}$, 45$^{th}$, and 61$^{st}$ amino acids in the amino acid sequence of SEQ ID NO: 10. In addition, in an embodiment, the IL-2 variant may be obtained by substitution of the 38$^{th}$, 42$^{nd}$, 45$^{th}$, and 72$^{nd}$ amino acids in the amino acid sequence of SEQ ID NO: 10. In addition, in an embodiment, the IL-2 variant may be obtained by substitution of the 38$^{th}$, 45$^{th}$, 61$^{st}$, and 72$^{nd}$ amino acids in the amino acid sequence of SEQ ID NO: 10. In addition, in an embodiment, the IL-2 variant may be obtained by substitution of the 38$^{th}$, 42$^{nd}$, 61$^{st}$, and 72$^{nd}$ amino acids in the amino acid sequence of SEQ ID NO: 10. In addition, in an embodiment, the IL-2 variant may be obtained by substitution of 42$^{nd}$, 45$^{th}$, 61$^{st}$, and 72$^{nd}$ amino acids in the amino acid sequence of SEQ ID NO: 10.

Furthermore, an IL-2 variant may be in a form in which five amino acids are substituted. Specifically, the IL-2 variant may be obtained by substitution of each of the 38$^{th}$, 42$^{nd}$, 45$^{th}$, 61$^{st}$, and 72$^{nd}$ amino acids in the amino acid sequence of SEQ ID NO: 10 with another amino acid.

Here, the "another amino acid" introduced by the substitution may be any one selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. However, regarding amino acid substitution for the IL-2 variant, in the amino acid sequence of SEQ ID NO: 10, the 38$^{th}$ amino acid cannot be substituted with arginine, the 42$^{nd}$ amino acid cannot be substituted with phenylalanine, the 45$^{th}$ amino acid cannot be substituted with tyrosine, the 61$^{st}$ amino acid cannot be substituted with glutamic acid, and the 72$^{nd}$ amino acid cannot be substituted with leucine.

Regarding amino acid substitution for an IL-2 variant, in the amino acid sequence of SEQ ID NO: 10, the 38$^{th}$ amino acid, arginine, may be substituted with an amino acid other than arginine. Preferably, regarding amino acid substitution for an IL-2 variant, in the amino acid sequence of SEQ ID NO: 10, the 38$^{th}$ amino acid, arginine, may be substituted with alanine (R38A).

Regarding amino acid substitution for an IL-2 variant, in the amino acid sequence of SEQ ID NO: 10, the 42$^{nd}$ amino acid, phenylalanine, may be substituted with an amino acid other than phenylalanine. Preferably, regarding amino acid substitution for an IL-2 variant, in the amino acid sequence of SEQ ID NO: 10, the 42$^{nd}$ amino acid, phenylalanine, may be substituted with alanine (F42A).

Regarding amino acid substitution for an IL-2 variant, in the amino acid sequence of SEQ ID NO: 10, the 45$^{th}$ amino acid, tyrosine, may be substituted with an amino acid other than tyrosine. Preferably, regarding amino acid substitution for an IL-2 variant, in the amino acid sequence of SEQ ID NO: 10, the 45$^{th}$ amino acid, tyrosine, may be substituted with alanine (Y45A).

Regarding amino acid substitution for an IL-2 variant, in the amino acid sequence of SEQ ID NO: 10, the 61$^{st}$ amino acid, glutamic acid, may be substituted with an amino acid other than glutamic acid. Preferably, regarding amino acid substitution for an IL-2 variant, in the amino acid sequence of SEQ ID NO: 10, the 61$^{st}$ amino acid, glutamic acid, may be substituted with arginine (E61R).

Regarding amino acid substitution for an IL-2 variant, in the amino acid sequence of SEQ ID NO: 10, the 72$^{nd}$ amino acid, leucine, may be substituted with an amino acid other than leucine. Preferably, regarding amino acid substitution for an IL-2 variant, in the amino acid sequence of SEQ ID NO: 10, the 72$^{nd}$ amino acid, leucine, may be substituted with glycine (L72G).

Specifically, an IL-2 variant may be obtained by at least one substitution selected from the group consisting of R38A, F42A, Y45A, E61R, and L72G, in the amino acid sequence of SEQ ID NO: 10.

Specifically, an IL-2 variant may be obtained by amino acid substitutions at two, three, four, or five positions among the positions selected from the group consisting of R38A, F42A, Y45A, E61R, and L72G.

In addition, an IL-2 variant may be in a form in which two amino acids are substituted. Specifically, an IL-2 variant may be obtained by the substitutions, R38A and F42A. In addition, in an embodiment, an IL-2 variant may be obtained by the substitutions, R38A and Y45A. In addition, in an embodiment, an IL-2 variant may be obtained by the substitutions, R38A and E61R. In addition, in an embodiment, an IL-2 variant may be obtained by the substitutions, R38A and L72G. In addition, in an embodiment, an IL-2 variant may be obtained by the substitutions, F42A and Y45A. In addition, in an embodiment, an IL-2 variant may be obtained by the substitutions, F42A and E61R. In addition, in an embodiment, an IL-2 variant may be obtained by the substitutions, F42A and L72G. In addition, in an embodiment, an IL-2 variant may be obtained by the substitutions, E61R and L72G.

Furthermore, an IL-2 variant may be in a form in which three amino acids are substituted. Specifically, an IL-2 variant may be obtained by the substitutions, R38A, F42A, and Y45A. In addition, in an embodiment, an IL-2 variant may be obtained by the substitutions, R38A, F42A, and E61R. In addition, in an embodiment, an IL-2 variant may be obtained by the substitutions, R38A, F42A, and L72G. In addition, in an embodiment, an IL-2 variant may be obtained by the substitutions, R38A, Y45A, and E61R. In addition, in an embodiment, an IL-2 variant may be obtained by the substitutions, R38A, Y45A, and L72G. In addition, in an embodiment, an IL-2 variant may be obtained by the substitutions, F42A, Y45A, and E61R. In addition, in an embodiment, an IL-2 variant may be obtained by the substitutions, F42A, Y45A, and L72G. In addition, in an embodiment, an IL-2 variant may be obtained by the substitutions, F42A, E61R, and L72G. In addition, in an embodiment, an IL-2 variant may be obtained by the substitutions, Y45A, E61R, and L72G.

In addition, an IL-2 variant may be in a form in which four amino acids are substituted. Specifically, an IL-2 variant may be obtained by the substitutions, R38A, F42A, Y45A, and E61R. In addition, in an embodiment, an IL-2 variant may be obtained by the substitutions, R38A, F42A, Y45A, and L72G. In addition, in an embodiment, an IL-2 variant may be obtained by the substitutions, R38A, F42A, E61R, and L72G. In addition, in an embodiment, an IL-2 variant may be obtained by the substitutions, R38A, Y45A, E61R, and L72G. In addition, in an embodiment, an IL-2 variant may be obtained by the substitutions, F42A, Y45A, E61R, and L72G.

Furthermore, an IL-2 variant may be obtained by the substitutions, R38A, F42A, Y45A, E61R, and L72G.

Preferably, an embodiment of the IL-2 variant may comprise which are any one selected from the following substitution combinations (a) to (d) in the amino acid sequence of SEQ ID NO: 10:

(a) R38A/F42A (b) R38A/F42A/Y45A (c) R38A/F42A/E61R (d) R38A/F42A/L72G

Here, when IL-2 has the amino acid sequence of SEQ ID NO: 35, an amino acid substitution may be present at a position complementarily corresponding to that in the amino acid sequence of SEQ ID NO: 10. In addition, even when IL-2 is a fragment of the amino acid sequence of SEQ ID NO: 35, an amino acid substitution may be present at a position complementarily corresponding to that in the amino acid sequence of SEQ ID NO: 10.

Specifically, an IL-2 variant may have the amino acid sequence of SEQ ID NO: 6, 22, 23, or 24.

In addition, an IL-2 variant may be characterized by having low in vivo toxicity. Here, the low in vivo toxicity may be a side effect caused by binding of IL-2 to the IL-2 receptor alpha chain (IL-2Rα). Various IL-2 variants have been developed to ameliorate the side effect caused by binding of IL-2 to IL-2Rα, and such IL-2 variants may be those disclosed in U.S. Pat. No. 5,229,109 and Korean Patent No. 1667096. In particular, IL-2 variants described in the present application have low binding ability for the IL-2 receptor alpha chain (IL-2Rα) and thus have lower in vivo toxicity than the wild-type IL-2.

As used herein, the term "CD80", also called "B7-1", is a membrane protein present in dendritic cells, activated B cells, and monocytes. CD80 provides co-stimulatory signals essential for activation and survival of T cells. CD80 is known as a ligand for the two different proteins, CD28 and CTLA-4, present on the surface of T cells. CD80 may consist of 288 amino acids, and may specifically have the amino acid sequence of SEQ ID NO: 11. In addition, as used herein, the term "CD80 protein" refers to the full-length CD80 or a CD80 fragment.

As used herein, the term "CD80 fragment" refers to a truncated form of CD80. In addition, the CD80 fragment may be an extracellular domain of CD80. An embodiment of the CD80 fragment may be obtained by elimination of the 1$^{st}$ to 34$^{th}$ amino acids from N-terminus which are a signal sequence of CD80. Specifically, an embodiment of the CD80 fragment may be a protein consisting of the 35$^{th}$ to 288$^{th}$ amino acids in SEQ ID NO: 11. In addition, an embodiment of the CD80 fragment may be a protein consisting of the 35$^{th}$ to 242$^{nd}$ amino acids in SEQ ID NO: 11. In addition, an embodiment of the CD80 fragment may be a protein consisting of the 35$^{th}$ to 232$^{nd}$ amino acids in SEQ ID NO: 11. In addition, an embodiment of the CD80 fragment may be a protein consisting of the 35$^{th}$ to 139$^{th}$ amino acids in SEQ ID NO: 11. In addition, an embodiment of the CD80 fragment may be a protein consisting of the 142$^{nd}$ to 242$^{nd}$ amino acids in SEQ ID NO: 11. In an embodiment, a CD80 fragment may have the amino acid sequence of SEQ ID NO: 2.

In addition, the IL-2 protein and the CD80 protein may be attached to each other via a linker or a carrier. Specifically, the IL-2 or a variant thereof and the CD80 (B7-1) or a fragment thereof may be attached to each other via a linker or a carrier. In the present description, the linker and the carrier may be used interchangeably.

The linker links two proteins. An embodiment of the linker may include 1 to 50 amino acids, albumin or a fragment thereof, an Fc domain of an immunoglobulin, or the like. Here, the Fc domain of immunoglobulin refers to a protein that comprises heavy chain constant region 2 (CH2) and heavy chain constant region 3 (CH3) of an immunoglobulin, and does not comprise heavy and light chain variable regions and light chain constant region 1 (CH1) of an immunoglobulin. The immunoglobulin may be IgG, IgA, IgE, IgD, or IgM, and may preferably be IgG4. Here, Fc domain of wild-type immunoglobulin G4 may have the amino acid sequence of SEQ ID NO: 4.

In addition, the Fc domain of an immunoglobulin may be an Fc domain variant as well as wild-type Fc domain. In addition, as used herein, the term "Fc domain variant" may refer to a form which is different from the wild-type Fc domain in terms of glycosylation pattern, has a high glycosylation as compared with the wild-type Fc domain, or has a low glycosylation as compared with the wild-type Fc domain, or a deglycosylated form. In addition, an aglycosylated Fc domain is included therein. The Fc domain or a variant thereof may be adapted to have an adjusted number of sialic acids, fucosylations, or glycosylations, through culture conditions or genetic manipulation of a host.

In addition, glycosylation of the Fc domain of an immunoglobulin may be modified by conventional methods such as chemical methods, enzymatic methods, and genetic engineering methods using microorganisms. In addition, the Fc domain variant may be in a mixed form of respective Fc regions of immunoglobulins, IgG, IgA, IgE, IgD, and IgM. In addition, the Fc domain variant may be in a form in which some amino acids of the Fc domain are substituted with other amino acids. An embodiment of the Fc domain variant may have the amino acid sequence of SEQ ID NO: 12.

The fusion protein may have a structure in which, using an Fc domain as a linker (or carrier), a CD80 protein and an IL-2 protein, or an IL-2 protein and a CD80 protein are linked to N-terminus and C-terminus of the linker or carrier, respectively (FIG. 1A). Linkage between N-terminus or C-terminus of the Fc domain, and CD80 or IL-2 may optionally be achieved by a linker peptide.

Specifically, a fusion protein may consist of the following structural formula (I) or (II):

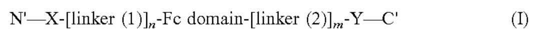

N'—X-[linker (1)]$_n$-Fc domain-[linker (2)]$_m$-Y—C' (I)

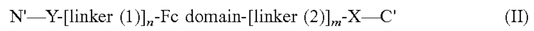

N'—Y-[linker (1)]$_n$-Fc domain-[linker (2)]$_m$-X—C' (II)

Here, in the structural formulas (I) and (II),

N' is the N-terminus of the fusion protein,

C' is the C-terminus of the fusion protein,

X is a CD80 protein,

Y is an IL-2 protein, the linkers (1) and (2) are peptide linkers, and n and m are each independently 0 or 1.

Preferably, the fusion protein may consist of the structural formula (I). The IL-2 protein is as described above. In addition, the CD80 protein is as described above. According to an embodiment, the IL-2 protein may be an IL-2 variant with one to five amino acid substitutions as compared with the wild-type IL-2. The CD80 protein may be a fragment obtained by truncation of up to about 34 contiguous amino acid residues from the N-terminus or C-terminus of the wild-type CD80. Alternatively, the CD80 protein may be an extracellular immunoglobulin-like domain having the activity of binding to the T cell surface receptors CTLA-4 and CD28.

Specifically, the fusion protein may have the amino acid sequence of SEQ ID NO: 9, 26, 28, or 30. According to another embodiment, the fusion protein includes a polypeptide having a sequence identity of 85%, 86%, 87%, 88%, 89%, 90%, 91%, 92%, 93%, 94%, 95%, 96%, 97%, 98%, 99%, or 100% to the amino acid sequence of SEQ ID NO: 9, 26, 28, or 30. Here, the identity is, for example, percent homology, and may be determined through homology comparison software such as BlastN software of the National Center of Biotechnology Information (NCBI).

The peptide linker (1) may be included between the CD80 protein and the Fc domain. The peptide linker (1) may consist of 5 to 80 contiguous amino acids, 20 to 60 contiguous amino acids, 25 to 50 contiguous amino acids, or 30 to 40 contiguous amino acids. In an embodiment, the peptide linker (1) may consist of 30 amino acids. In addition, the peptide linker (1) may comprise at least one cysteine. Specifically, the peptide linker (1) may comprise one, two, or three cysteines. In addition, the peptide linker (1) may be derived from the hinge of an immunoglobulin. In an embodiment, the peptide linker (1) may be a peptide linker consisting of the amino acid sequence of SEQ ID NO: 3.

The peptide linker (2) may consist of 1 to 50 contiguous amino acids, 3 to 30 contiguous amino acids, or 5 to 15 contiguous amino acids. In an embodiment, the peptide linker (2) may be (G4S)$_n$ (where n is an integer of 1 to 10). Here, in (G4S)$_n$, n may be 1, 2, 3, 4, 5, 6, 7, 8, 9, or 10. In an embodiment, the peptide linker (2) may be a peptide linker consisting of the amino acid sequence of SEQ ID NO: 5.

In another aspect of the present invention, provided is a dimer obtained by binding of two fusion proteins, each of which comprises an IL-2 protein and a CD80 protein. The fusion protein comprising IL-2 or a variant thereof and CD80 or a fragment thereof is as described above.

Here, the binding between the fusion proteins constituting the dimer may be achieved by, but is not limited to, a disulfide bond formed by cysteines present in the linker. The fusion proteins constituting the dimer may be the same or different fusion proteins from each other. Preferably, the dimer may be a homodimer. An embodiment of the fusion protein constituting the dimer may be a protein having the amino acid sequence of SEQ ID NO: 9.

NK Cell Culture Method 1

Another aspect of the present invention provides a method for culturing a natural killer cell, including: i) isolating a cell that do not express CD3 from peripheral blood mononuclear cells (PBMC); ii) isolating a cell that express CD56 from the cell that do not express CD3 isolated in the above step; and iii) culturing the isolated cells in the presence of a fusion protein dimer comprising IL-2 or a variant thereof and CD80 or a fragment thereof.

The term “PBMC” as used in the present invention means a peripheral blood mononuclear cell. The PBMC is composed of lymphocytes (T cells, B cells, natural killer cells) and monocytes, and can be isolated from whole blood by Ficoll and centrifugation. The PBMC may be isolated from whole blood obtained from an individual.

The fusion protein dimer is as described in detail for a composition for culturing natural killer cells. The fusion protein dimer may be treated at a concentration of 1 nM to 500 nM. Specifically, the fusion protein dimer may be treated at a concentration of 1 nM to 500 nM, 5 nM to 300 nM, or 10 nM to 150 nM. In an embodiment of the present invention, the fusion protein dimer was treated at a concentration of 1.6 nM or 50 nM.

A method for culturing the isolated cells may be performed using a method widely known in the art. Specifically, the culture temperature in the step of culturing the isolated cells may be 27° C. to 40° C., or 30° C. to 37° C. In an embodiment of the present invention, culture was performed at a temperature of 37° C. In addition, in the step of culturing the isolated cells, $CO_2$ concentration condition during culture may be 1% to 10%, and preferably, it may be cultured in a 5% $CO_2$ condition.

In the step of culturing the isolated cells, culture period may be 5 days to 25 days, 6 days to 23 days, or 7 days to 21 days. In an embodiment of the present invention, culture period was 20 days, and a significant difference in proliferation appeared from the 5th day.

Obtained NK Cells and Use Thereof

Another aspect of the present invention provides natural killer cells prepared by the method for culturing natural killer cells.

The natural killer cells may have increased expression of CD16 and NKp46. The natural killer cells may have increased expression of granzyme B and perforin. The natural killer cells cultured according to the method for culturing natural killer cells may be frozen and the function of cells is not impaired even when thawed again.

Due to high expression of activating receptors such as CD16 and NKp46, the natural killer cells exhibit increased killing capacity against a cancer cell line and increased secretion of granzyme B and perforin, and thus an excellent anticancer effect may be expected. Therefore, a therapeutic agent effective for treating cancer may be prepared, using a large amount of activated natural killer cells which are clinically applicable. In addition, the natural killer cells may have high expression of NKp30 or DNAM1.

Still another aspect of the present invention provides a pharmaceutical composition for preventing or treating cancer including the natural killer cells as an active ingredient.

In addition, natural killer cells prepared by the method for culturing natural killer cells may be included in amount of 10 to 95% by weight based on the total weight of the pharmaceutical composition. Further, the pharmaceutical composition may further include, in addition to the active ingredient, at least one active ingredient that exhibits the same or similar functions.

A dosage of the pharmaceutical composition may be adjusted according to various factors including type of disease, severity of disease, kinds and content of active ingredients and other ingredients included in the composition, kinds of formulation, and age, weight, general health condition, gender, and diet of a patient, time of administration, route of administration, and secretion rate of a composition, duration of treatment, and simultaneously used drugs.

However, for a desirable effect, a dosage of the pharmaceutical composition may be $1\times10^2$ cells/kg to $1.0\times10^{13}$ cells/kg, and $1\times10^7$ cells/kg to $1.5\times10^{11}$ cells/kg based on the natural killer cells, which is an active ingredient. In this case, the dose may be administered once a day, or may be divided in several times.

In addition, the pharmaceutical composition may be administered to an individual by various methods known in the art. The route of administration may be appropriately selected by a person skilled in the art in consideration of the method of administration, volume of body fluid, viscosity, or the like.

The cancer may be any one selected from the group consisting of gastric cancer, liver cancer, lung cancer, colorectal cancer, breast cancer, prostate cancer, ovarian cancer, pancreatic cancer, cervical cancer, thyroid cancer, larynx cancer, acute lymphoblastic leukemia, brain tumor, neuroblastoma, retinoblastoma, head and neck cancer, salivary cancer, and lymphoma.

Treatment Method Using the Obtained NK Cells

Another aspect of the present invention provides a method for treating cancer including administering the NK cell to an individual having cancer. In this case, the NK cells and cancer are as described above. Still another aspect of the present invention provides use of the NK cell to treat cancer.

NK Cell Culture Method 2

Another aspect of the present invention provides a method for culturing a natural killer cell, including: i) isolating a cell that do not express CD3 from PBMCs; and ii) culturing the isolated cell in the presence of a fusion protein dimer comprising IL-2 or a variant thereof and CD80 or a fragment thereof.

Another aspect of the present invention provides natural killer cells prepared by the method for culturing natural killer cell. Yet another aspect of the present invention provides a pharmaceutical composition for preventing or treating cancer, including the natural killer cell as an active ingredient. Still another aspect of the present invention provides a method for treating cancer including administering the NK cell to an individual having cancer. In this case, the NK cell and cancer are as described above. Yet still another aspect of the present invention provides use of the NK cell to treat cancer.

Due to high expression of activating receptors such as CD16 and NKp46, the natural killer cells exhibit increased killing capacity against a cancer cell line and increased secretion of granzyme B and perforin, and thus an excellent anticancer effect may be expected. Therefore, a therapeutic agent effective for treating cancer may be prepared, using a large amount of activated natural killer cells which are clinically applicable. In addition, the natural killer cells may have high expression of NKp30 or DNAM1.

The cancer may be any one selected from the group consisting of gastric cancer, liver cancer, lung cancer, colorectal cancer, breast cancer, prostate cancer, ovarian cancer, pancreatic cancer, cervical cancer, thyroid cancer, larynx cancer, acute lymphoblastic leukemia, brain tumor, neuroblastoma, retinoblastoma, head and neck cancer, salivary cancer, and lymphoma.

NK Cell Culture Method 3

Another aspect of the present invention provides a method for culturing natural killer cells, including: i) isolating a cell that express CD56 from PBMCs; and ii) culturing the isolated cell in the presence of a fusion protein dimer comprising IL-2 or a variant thereof and CD80 or a fragment thereof.

Yet another aspect of the present invention provides a natural killer cell prepared by the method for culturing natural killer cell. Due to high expression of activating receptors such as CD16 and NKp46, the natural killer cells exhibit increased killing capacity against a cancer cell line and increased secretion of granzyme B and perforin, and thus an excellent anticancer effect may be expected. Therefore, a therapeutic agent effective for treating cancer may be prepared, using a large amount of activated natural killer cells which are clinically applicable. In addition, the natural killer cells may have high expression of NKp30 or DNAM1.

Yet another aspect of the present invention provides a pharmaceutical composition for preventing or treating cancer, including the natural killer cell as an active ingredient. Still another aspect of the present invention provides a method for treating cancer including administering the NK cell to an individual having cancer. In this case, NK cells and cancer are as described above. Yet still another aspect of the present invention provides use of the NK cells to treat cancer.

The cancer may be any one selected from the group consisting of gastric cancer, liver cancer, lung cancer, colorectal cancer, breast cancer, prostate cancer, ovarian cancer, pancreatic cancer, cervical cancer, thyroid cancer, larynx cancer, acute lymphoblastic leukemia, brain tumor, neuroblastoma, retinoblastoma, head and neck cancer, salivary cancer, and lymphoma.

NK Cell Culture Method 4

Another aspect of the present invention provides a method for promoting the activity of natural killer cells in PBMCs, including culturing PBMCs in the presence of a fusion protein dimer comprising IL-2 or a variant thereof and CD80 or a fragment thereof.

Yet another aspect of the present invention provides PBMCs prepared by the method for promoting the activity of natural killer cells in the PBMCs. The natural killer cells in PBMC have high expression of an activating receptor such as CD16 and NKp46 so that increase the cell killing capacity against cancer cell lines and secretion of granzyme B and perforin, and thus excellent anticancer effects can be expected. Therefore, a therapeutic agent effective for treating cancer may be prepared using PBMCs including a large amount of activated natural killer cells which are clinically applicable. In addition, the natural killer cells in PBMCs may have high expression of NKp30 or DNAM1.

Still another aspect of the present invention provides a pharmaceutical composition for preventing or treating cancer including the PBMCs as an active ingredient. Yet still another aspect of the present invention provides a method for treating cancer including administering the NK cells to an individual having cancer. In this case, NK cells and cancer are as described above. Yet still another aspect of the present invention provides use of the NK cells to treat cancer.

The cancer may be any one selected from the group consisting of gastric cancer, liver cancer, lung cancer, colorectal cancer, breast cancer, prostate cancer, ovarian cancer, pancreatic cancer, cervical cancer, thyroid cancer, larynx cancer, acute lymphoblastic leukemia, brain tumor, neuroblastoma, retinoblastoma, head and neck cancer, salivary cancer, and lymphoma.

MODE FOR CARRYING OUT THE INVENTION

Hereinafter, the present invention will be described in more detail by way of the following examples. However, the following examples are only for illustrating the present invention, and the scope of the present invention is not limited thereto.

I. Preparation of GI-101, Natural Killer Cells, and Natural Killer Cell Culture Composition

Preparatory Example 1. Preparation of a hCD80-Fc-IL-2 Variant (2M): GI-101

In order to produce a fusion protein including a human CD80 fragment, a Fc domain, and an IL-2 variant, a polynucleotide including a nucleotide sequence (SEQ ID NO: 8) encoding a fusion protein comprising a signal peptide (SEQ ID NO: 1), a CD80 fragment (SEQ ID NO: 2), a linker-conjugated Ig hinge (SEQ ID NO: 3), a Fc domain (SEQ ID NO: 4), a linker (SEQ ID NO: 5), and an IL-2 variant (2M) in which two amino acids are substituted (R38A, F42A) (SEQ ID NO: 6) in this order from N-terminus was synthesized through Invitrogen GENEART® Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 9. After introducing the vector, cells were cultured in an environment of 37° C., 125 RPM, and 8% $CO_2$ for 7 days, and then collected to purify a fusion protein. The purified fusion protein dimer was named as "GI-101."

Purification was performed using chromatography including MABSELECT SURE® protein A resin (Cytiva Bioprocess R&D AB, Uppsala, Sweden). The fusion protein was bound under the condition of 25 mM Tris, 25 mM NaCl, and pH 7.4. Then, it was eluted with 100 mM NaCl and 100 mM acetic acid at pH 3. After putting 20% of 1M Tris-HCl at pH 9 into a collection tube, the fusion protein was collected. The collected fusion protein was dialyzed into PBS buffer for 16 hours to change.

Figure 1B:
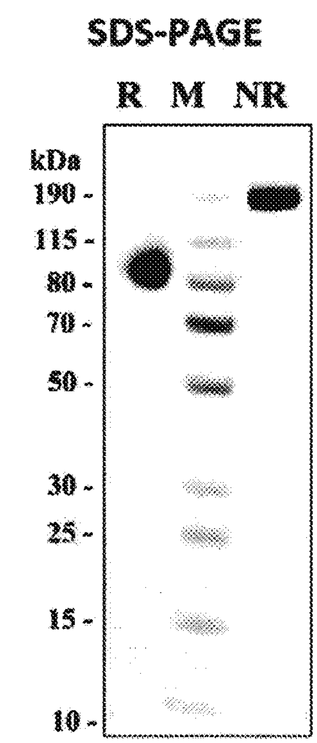
FIG. 1B shows an image of SDS-PAGE confirming the obtained fusion protein dimer (GI-101)
Figure 1C:
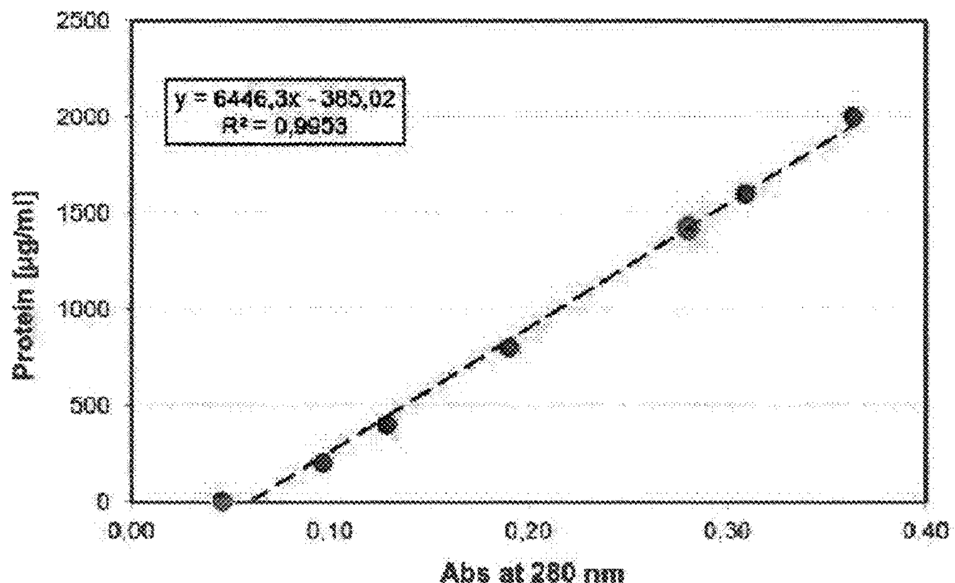
FIG. 1C shows a content of the fusion protein dimer (GI-101) according to the absorbance.
Figure 1D:
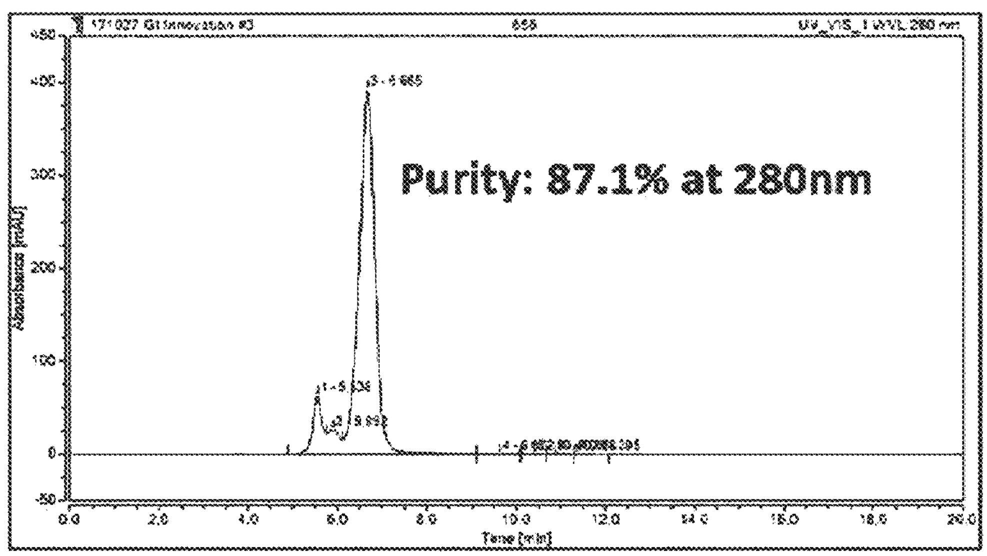
FIG. 1D shows a result of size exclusion chromatography (SEC) analysis of the obtained fusion protein dimer (GI-101)

Then, absorbance at a wavelength of 280 nm over time was measured by using size exclusion chromatography with a TSKGEL® G3000SWXL chromatography column (TOSOH Bioscience) to obtain a high concentration of fusion protein. At this time, the isolated and purified fusion protein was subjected to SDS-PAGE under the reducing (R) or non-reducing (NR) conditions, and stained with coomassie blue to confirm its purity (FIG. 1B). It was confirmed that the fusion protein was included at a concentration of 2.78 mg/ml as detected using a NANODROP® spectrophotometer (NanoDrop Technologies, Inc., Wilmington, Delaware) (FIG. 1C). Also, the result analyzed using size exclusion chromatography is as shown in FIG. 1D.

Preparatory Example 2. Preparation of a Fc-IL-2 Variant (2M) Dimer: Fc-IL-2v2

In order to produce a fusion protein comprising a Fc domain and an IL-2 variant, a polynucleotide including a nucleotide sequence (SEQ ID NO: 45) encoding a fusion protein comprising a signal peptide (SEQ ID NO: 1), an Ig hinge (SEQ ID NO: 38), a Fc domain (SEQ ID NO: 4), a linker (SEQ ID NO: 5), and an IL-2 variant (2M) in which two amino acids are substituted (R38A, F42A) (SEQ ID NO: 6) in this order from N-terminus was synthesized through Invitrogen GENEART® Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 44. After introducing the vector, the cells were cultured in an environment of 37° C., 125 RPM, and 8% $CO_2$ for 7 days, and then collected to purify a fusion protein dimer. The purified fusion protein dimer was named as "Fc-IL2v2."

Figure 3A:
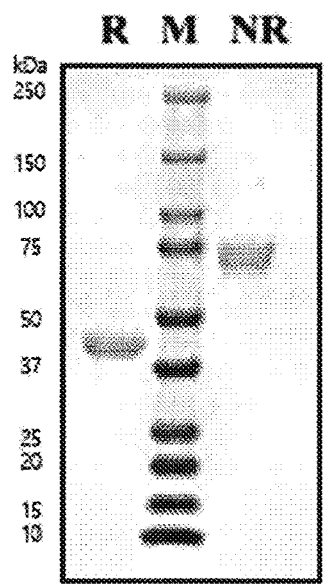
FIG. 3A shows an image of SDS-PAGE confirming the obtained Fc-IL2v2 fusion protein dimer.
Figure 3B:
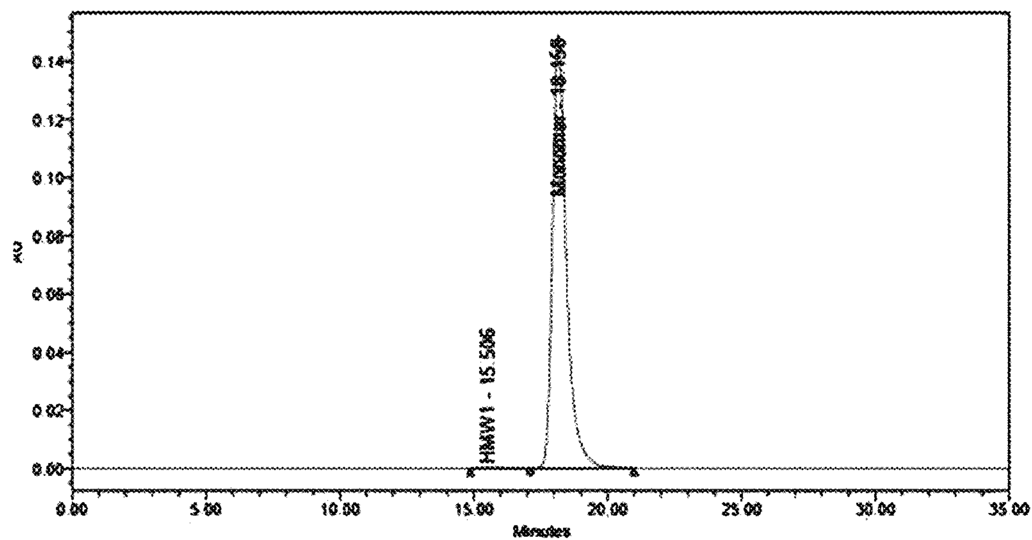
FIG. 3B shows results of size exclusion chromatography (SEC) analysis of the obtained Fc-IL2v2 fusion protein dimer.

The purification and collection of the fusion protein were performed in the same manner as in the Preparatory Example 1. The isolated and purified fusion protein was subjected to SDS-PAGE under the reducing (R) or non-reducing (NR) conditions, and stained with coomassie blue to confirm its purity (FIG. 3A). As a result, it was confirmed that the fusion protein forms a dimer. Also, the result analyzed using size exclusion chromatography is as shown in FIG. 3B.

Preparatory Example 3. Preparation of a Fc-IL-2 Dimer: Fc-IL-2 wt

In order to produce a fusion protein comprising a Fc domain and a wild-type IL-2, a polynucleotide including a nucleotide sequence (SEQ ID NO: 43) encoding a fusion protein comprising a signal peptide (SEQ ID NO: 1), an Ig hinge (SEQ ID NO: 38), a Fc domain (SEQ ID NO: 4), a linker (SEQ ID NO: 5), and a wild-type IL-2 (SEQ ID NO: 10) in this order from N-terminus was synthesized through Invitrogen GENEART® Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 42. After introducing the vector, the cells were cultured in an environment of 37° C., 125 RPM, and 8% CO2 for 7 days, and then collected to purify a fusion protein dimer. The purified fusion protein dimer was named as "Fc-IL2 wt."

Figure 3C:
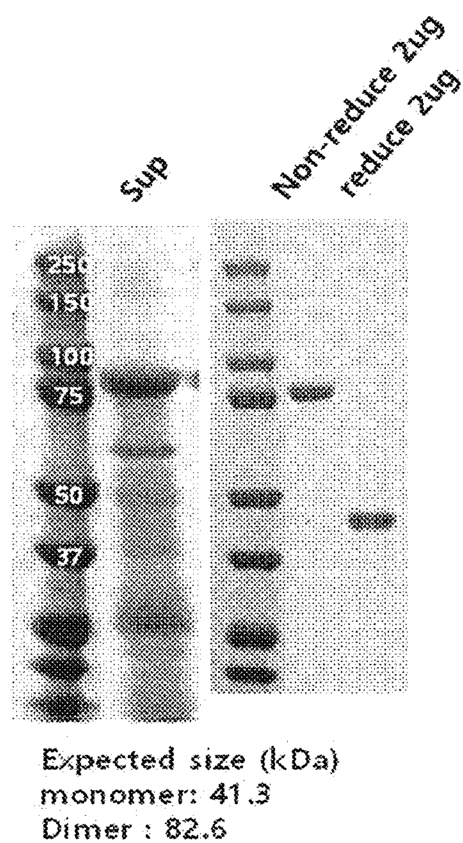
FIG. 3C shows images of SDS-PAGE confirming the obtained Fc-IL2 wt fusion protein dimer.
Figure 3D:
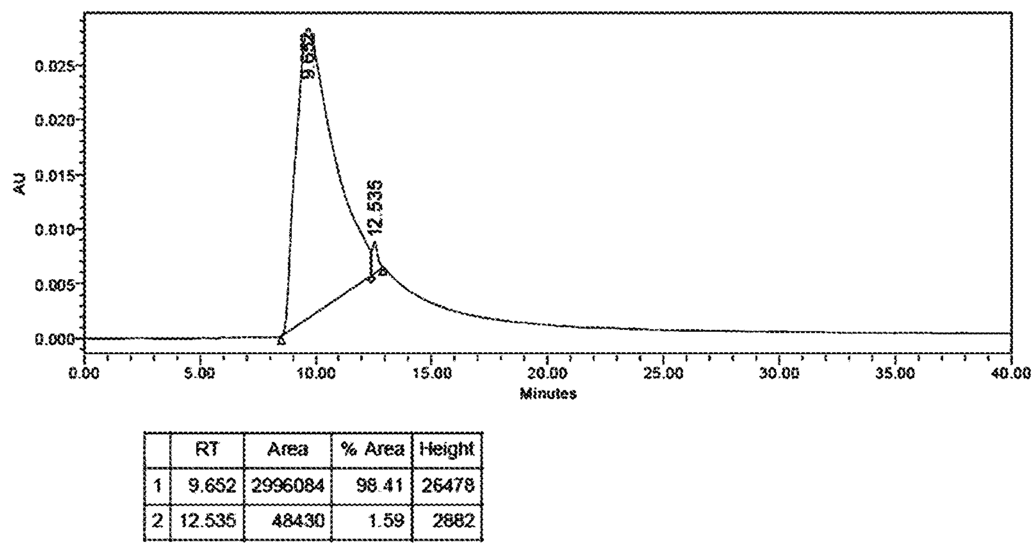
FIG. 3D shows results of size exclusion chromatography (SEC) analysis of the obtained Fc-IL2 wt fusion protein dimer.

The purification and collection of the fusion protein were performed in the same manner as in the Preparatory Example 1. The isolated and purified fusion protein was subjected to SDS-PAGE under the reducing (R) or non-reducing (NR) conditions, and stained with coomassie blue to confirm its purity (FIG. 3C). As a result, it was confirmed that the fusion protein forms a dimer. Also, the result analyzed using size exclusion chromatography is as shown in FIG. 3D.

Preparatory Example 4. Preparation of a hCD80-Fc-IL-2 Wild-Type Dimer: hCD80-Fc-IL-2 wt In order to produce a fusion protein comprising a human CD80 fragment, a Fc domain, and an IL-2 wile-type protein, a polynucleotide including a nucleotide sequence (SEQ ID NO: 41) encoding a fusion protein comprising a signal peptide (SEQ ID NO: 1), a CD80 fragment (SEQ ID NO: 2), a linker-conjugated Ig hinge (SEQ ID NO: 3), a Fc domain (SEQ ID NO: 4), a linker (SEQ ID NO: 5), and IL-2 wild-type (SEQ ID NO: 10) in this order from N-terminus was synthesized through Invitrogen GENEART® Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 46. After introducing the vector, the cells were cultured in an environment of 37° C., 125 RPM, and 8% $CO_2$ concentration for 7 days, and then collected to purify a fusion protein dimer. The purified fusion protein dimer was named as "hCD80-Fc-IL2 wt.".

Purification was performed using chromatography including MABSELECT SURE® protein A resin (Cytiva Bioprocess R&D AB, Uppsala, Sweden). The fusion protein was bound under the condition of 25 mM Tris, 25 mM NaCl, and pH 7.4. Then, it was eluted with 100 mM NaCl and 100 mM acetic acid at pH 3. After putting 20% of 1M Tris-HCl at pH 9 into a collection tube, the fusion protein was collected. The collected fusion protein was dialyzed into PBS buffer for 16 hours to change.

Figure 4A:
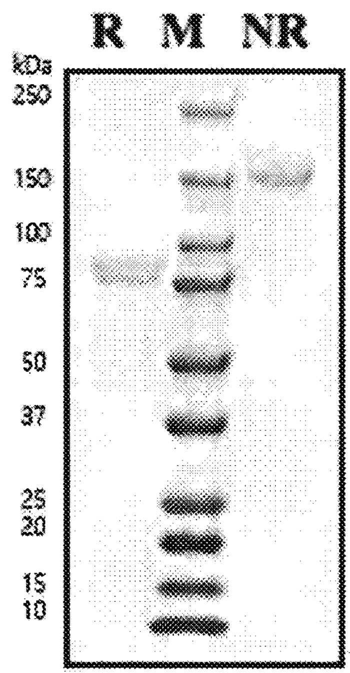
FIG. 4A shows an image of SDS-PAGE confirming the obtained hCD80-Fc-IL2 wt fusion protein dimer.
Figure 4B:
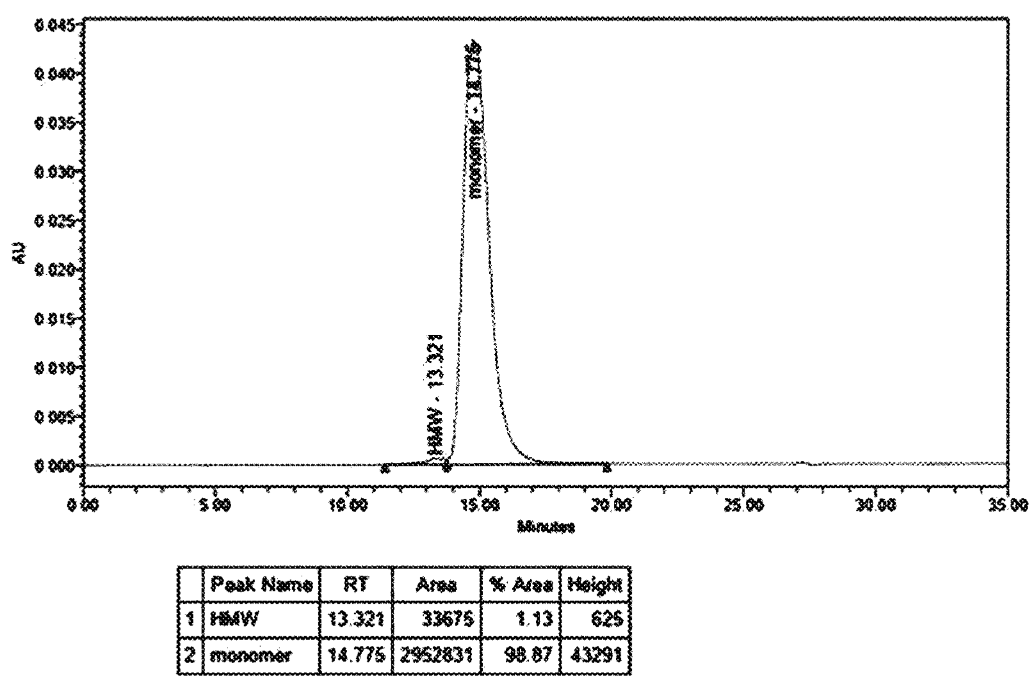
FIG. 4B shows results of size exclusion chromatography (SEC) analysis of the obtained hCD80-Fc-IL2 wt fusion protein dimer.
Figure 5A:
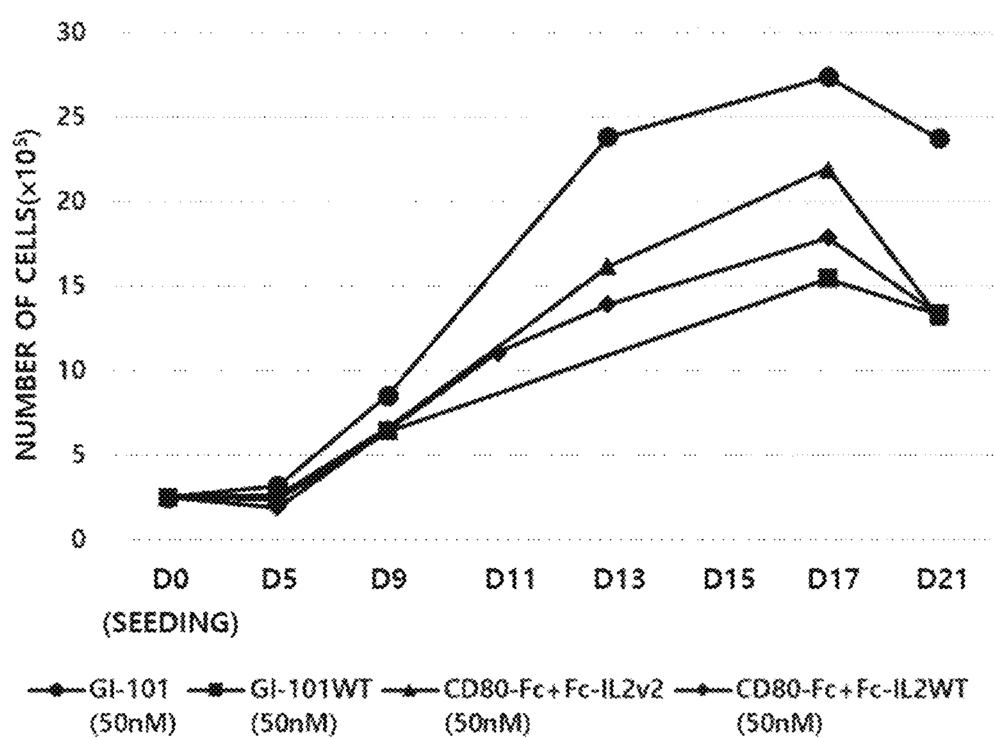
FIGS. 5A and 5B show the number of NK cells when cultured in an AIM-V (5% SR) condition.
Figure 5B:
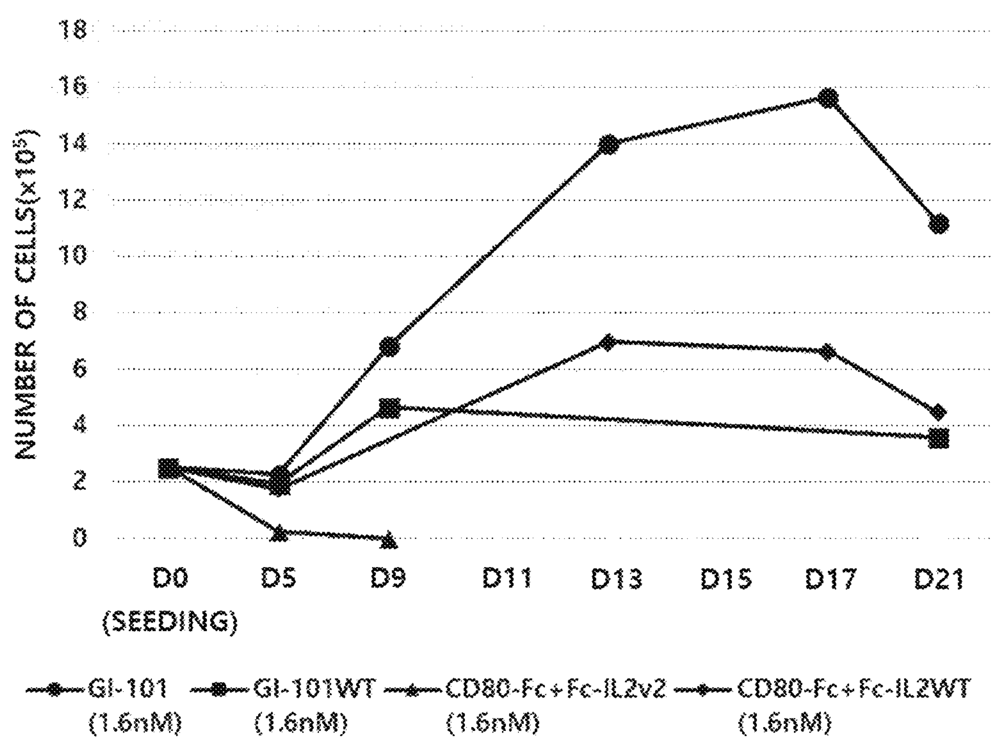
Figure 6A:
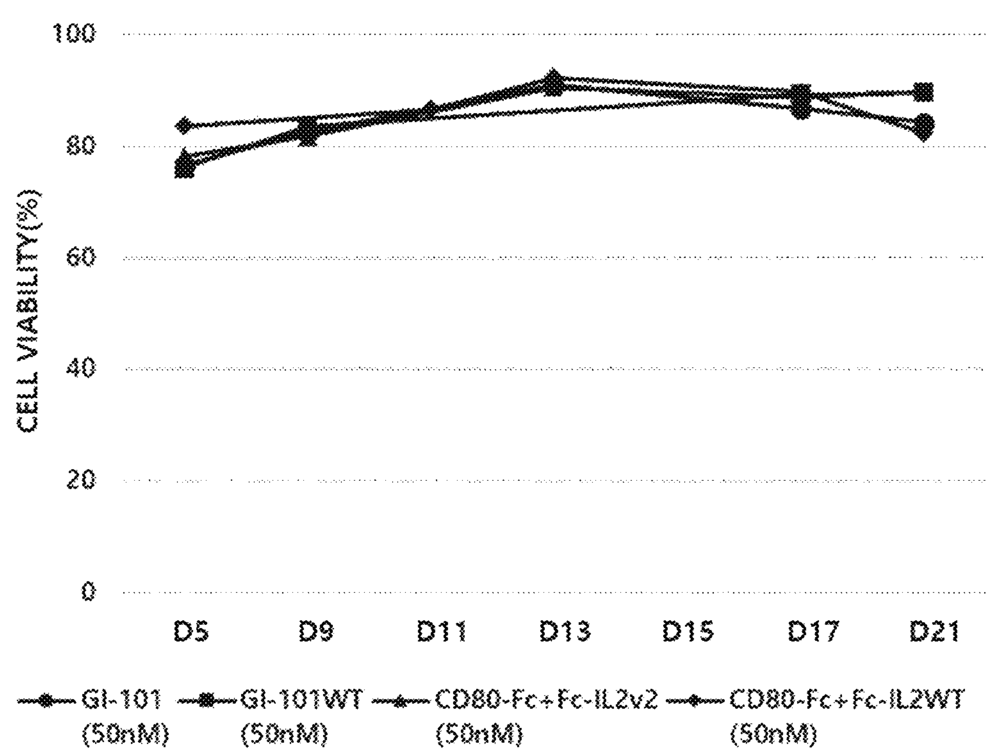
FIGS. 6A and 6B show the viability of NK cells when cultured in an AIM-V (5% SR) condition.
Figure 6B:
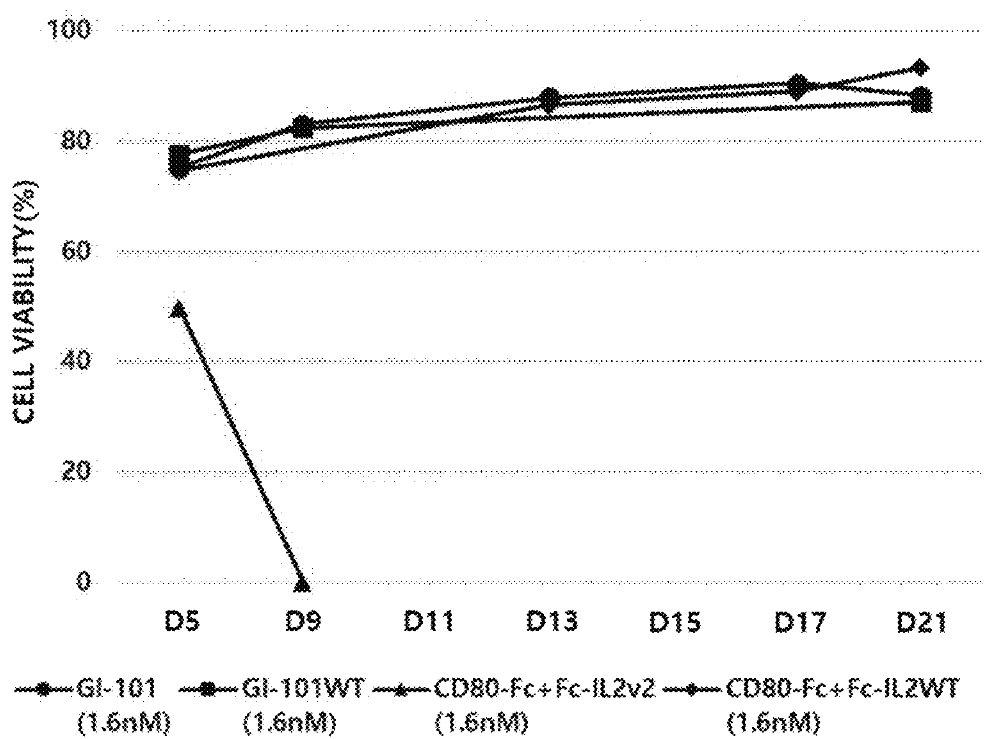
Figure 7A:
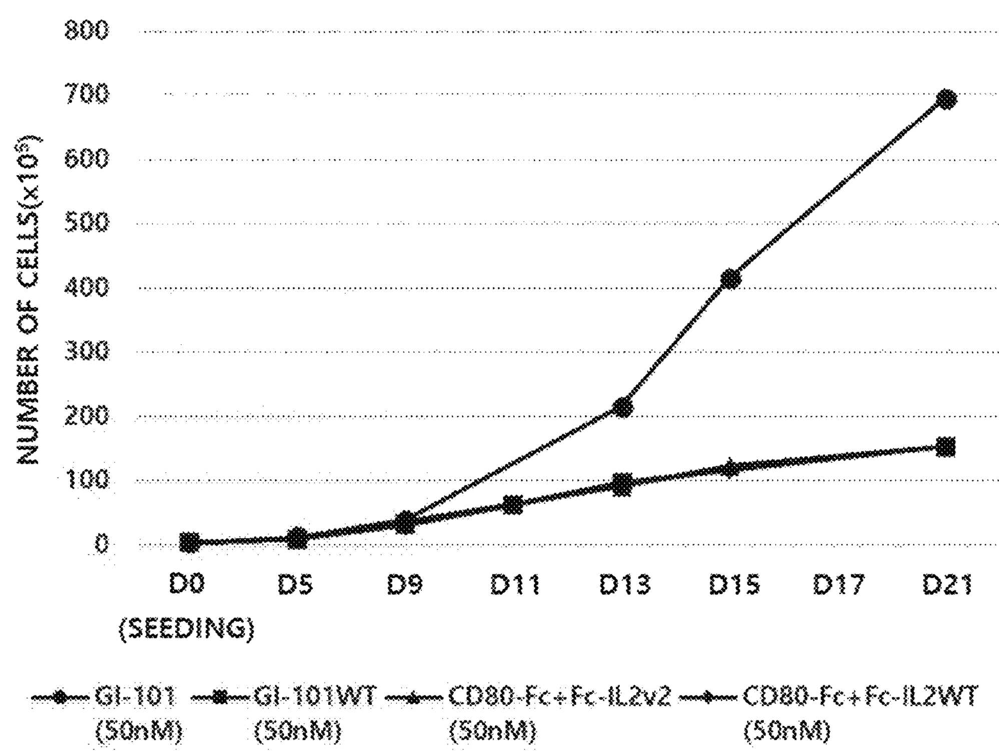
FIGS. 7A and 7B show the number of NK cells when cultured in an AIM-V (5% hABS) condition.
Figure 7B:
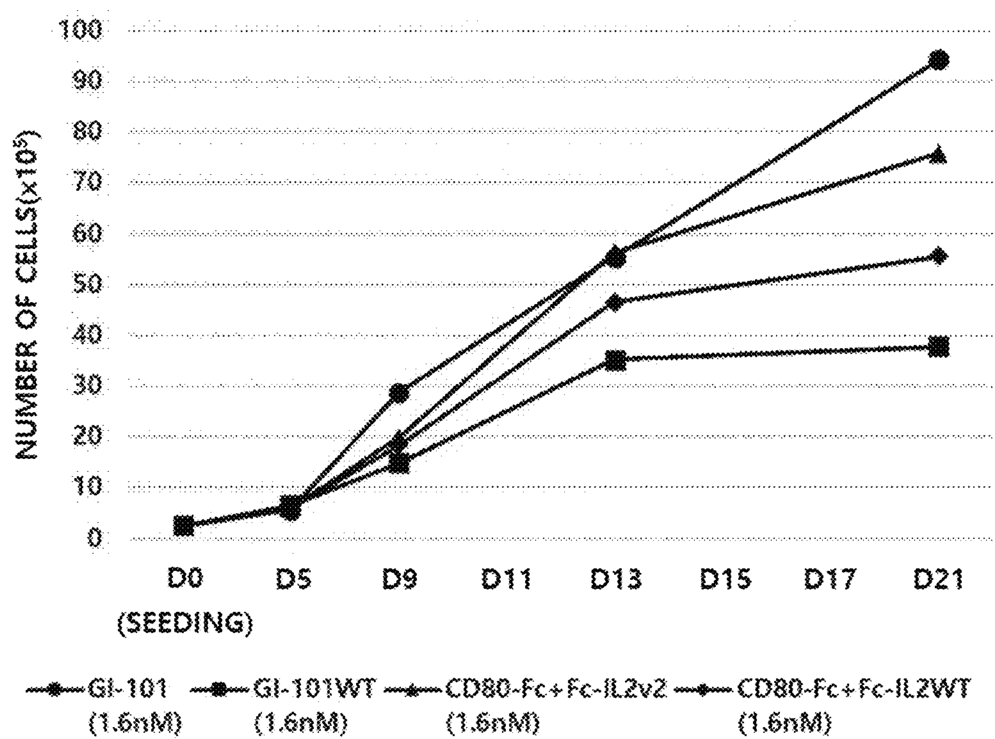
Figure 8A:
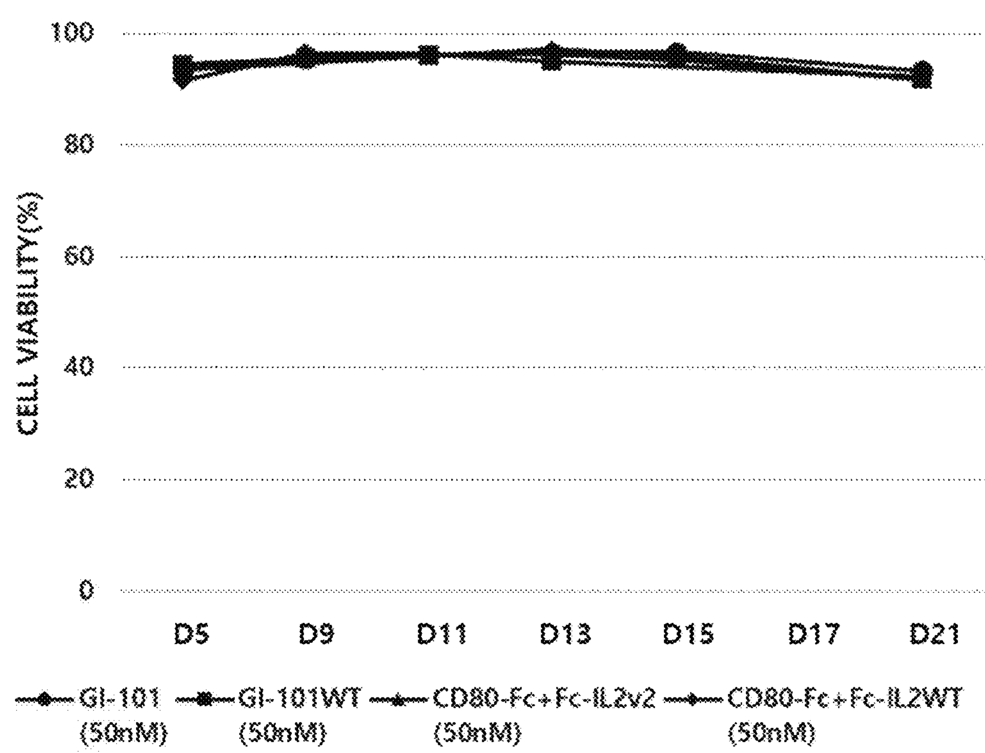
FIGS. 8A and 8B show the viability of NK cells when cultured in an AIM-V (5% hABS) condition.
Figure 8B:
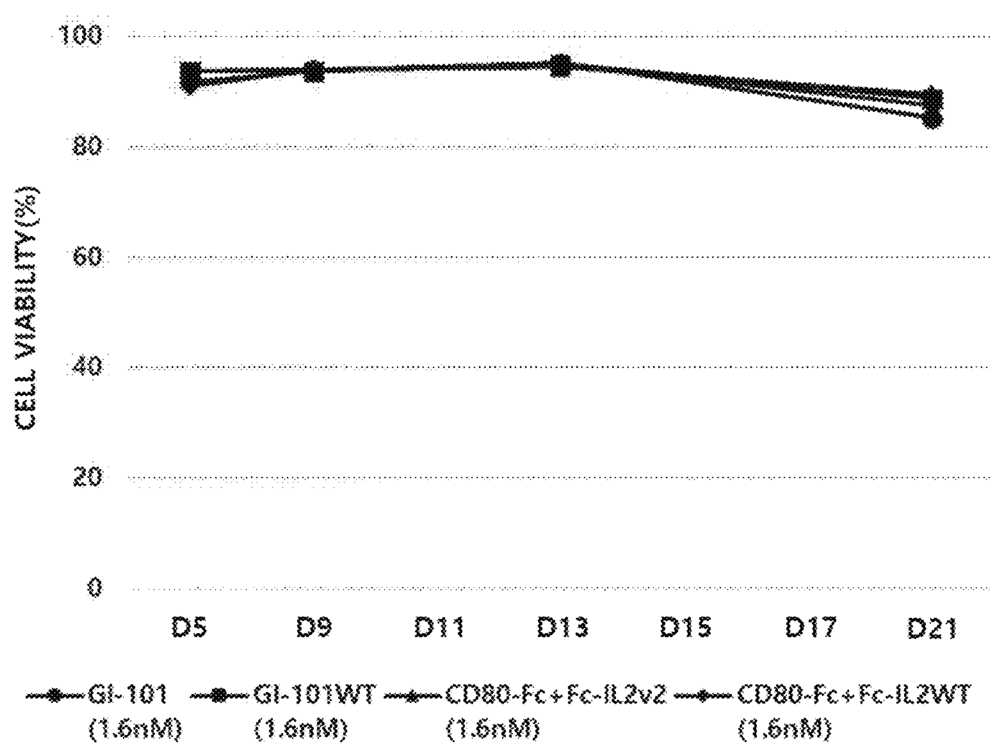
Figure 9A:
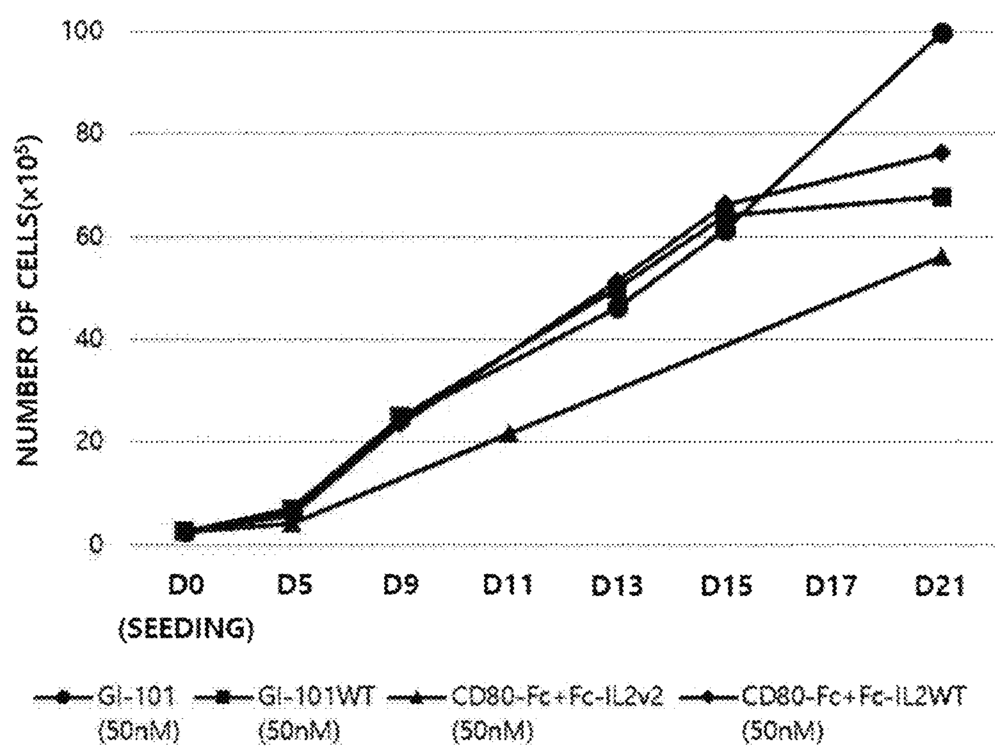
FIGS. 9A and 9B show the number of NK cells when cultured in an X-VIVO (5% hABS) condition.
Figure 9B:
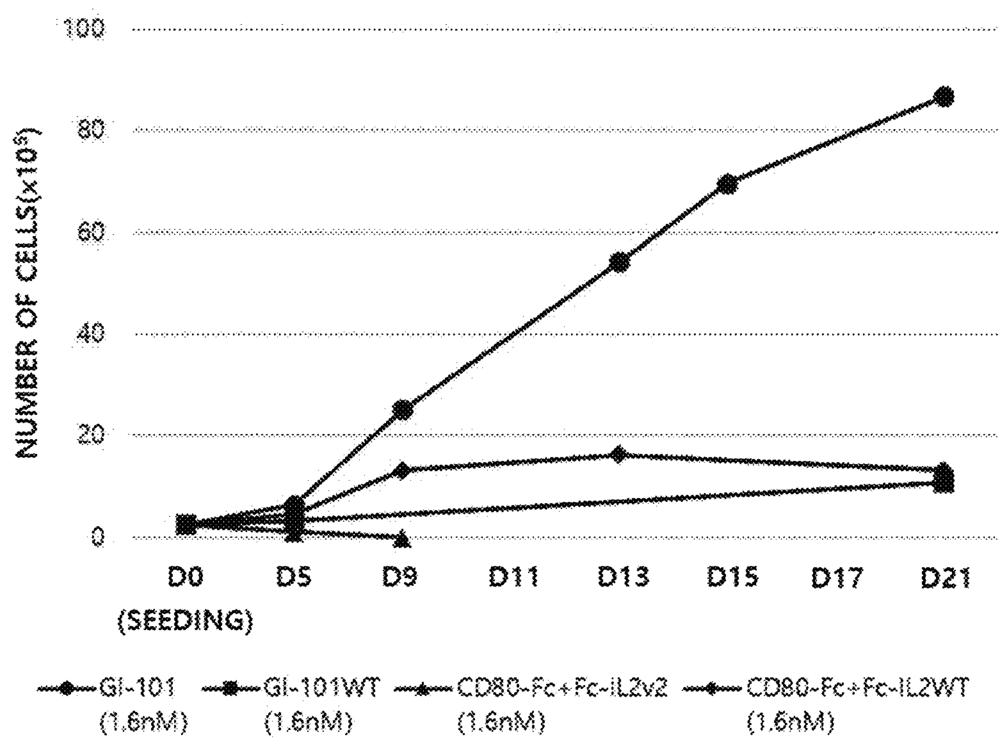
Figure 10A:
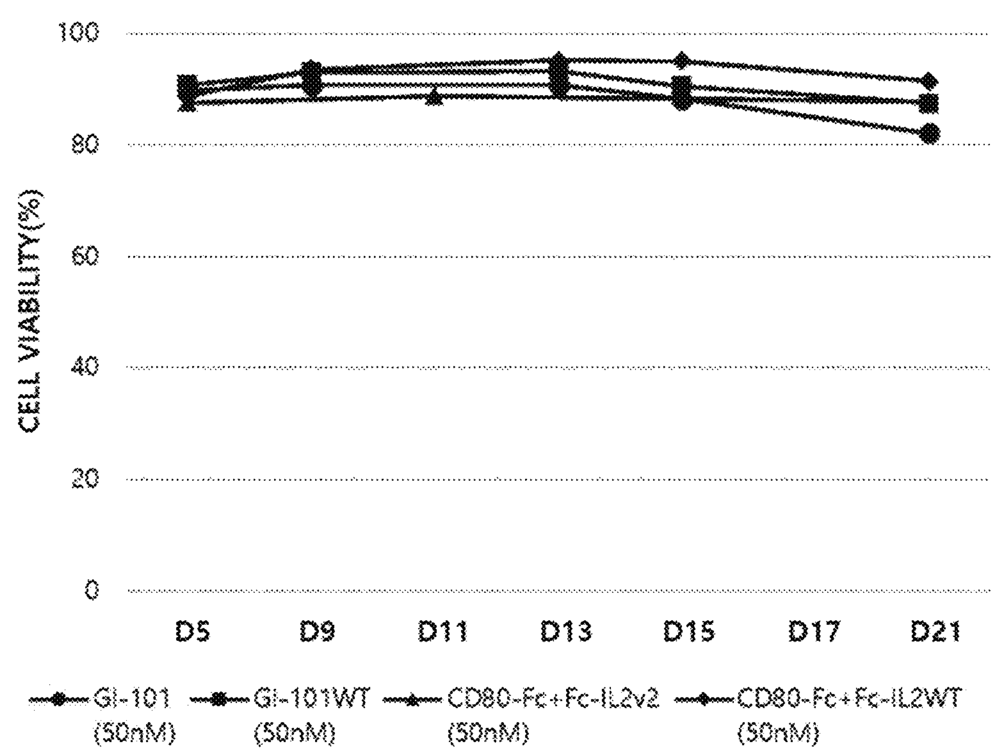
FIGS. 10A and 10B show the viability of NK cells when cultured in an X-VIVO (5% hABS) condition.
Figure 10B:
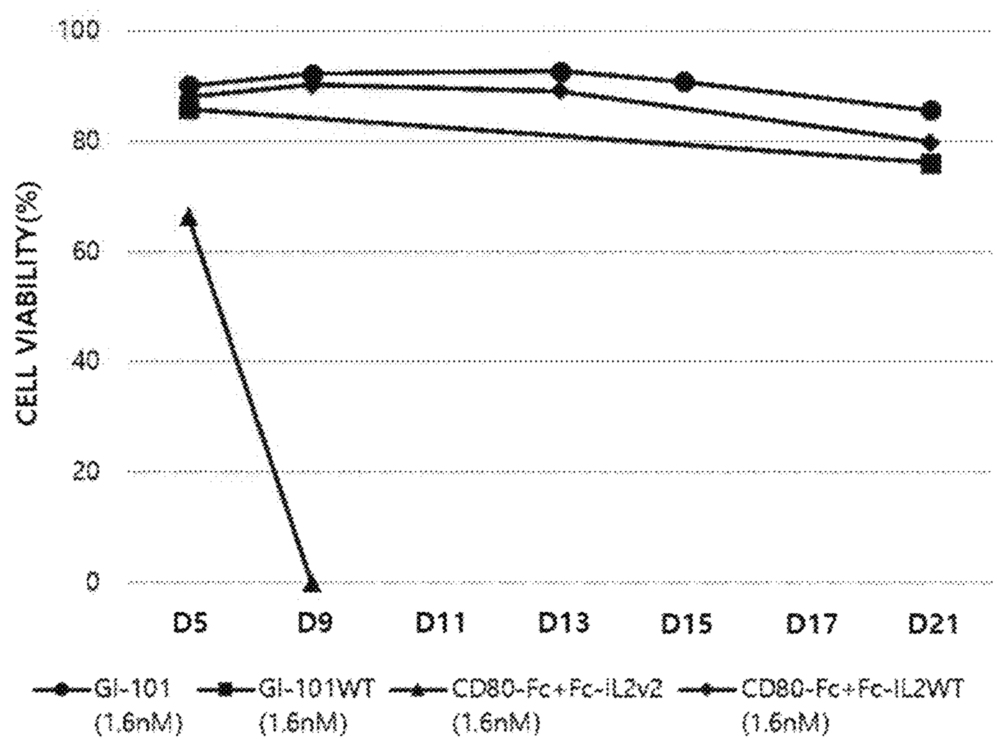
Figure 11A:
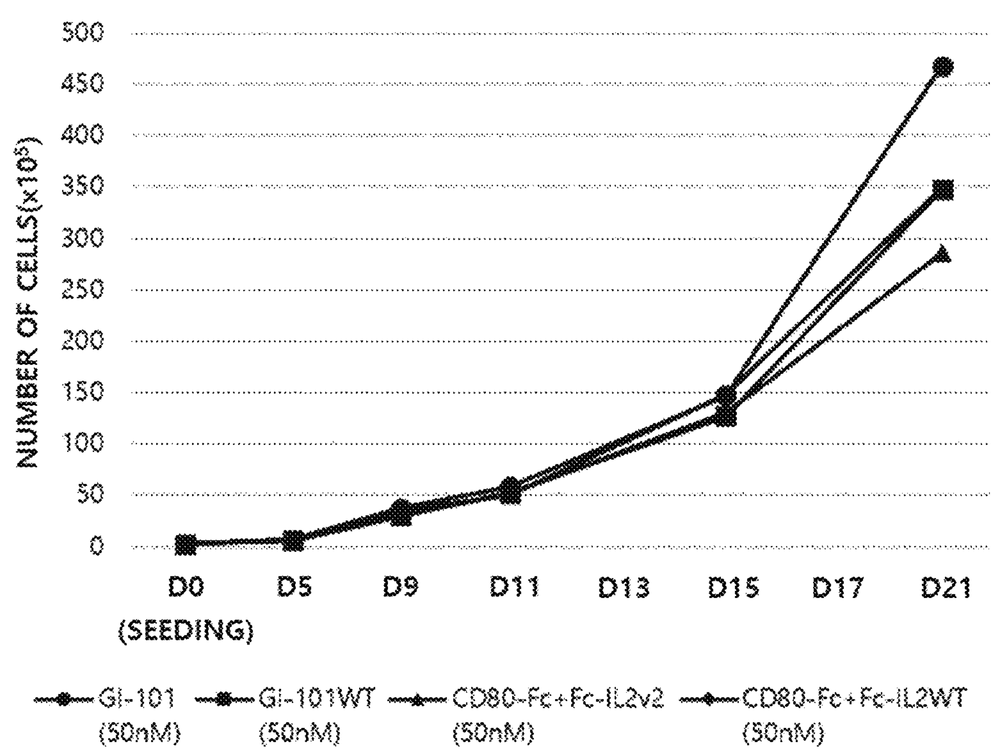
FIGS. 11A and 11B show the number of NK cells when cultured in an NK MACS (5% hABS) condition.
Figure 11B:
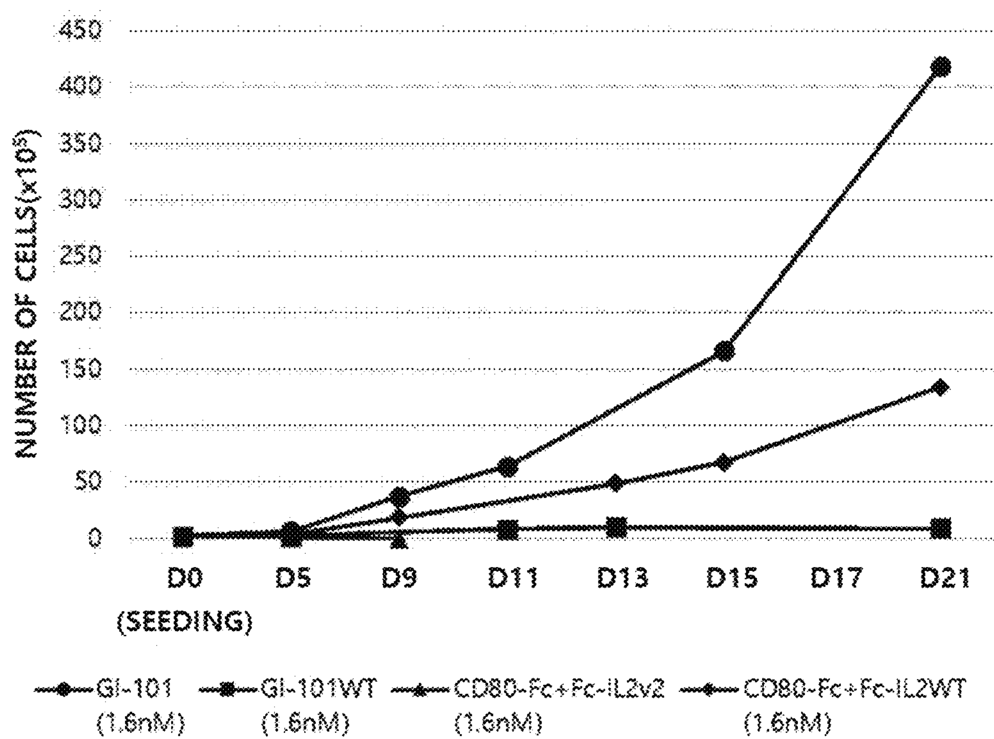
Figure 12A:
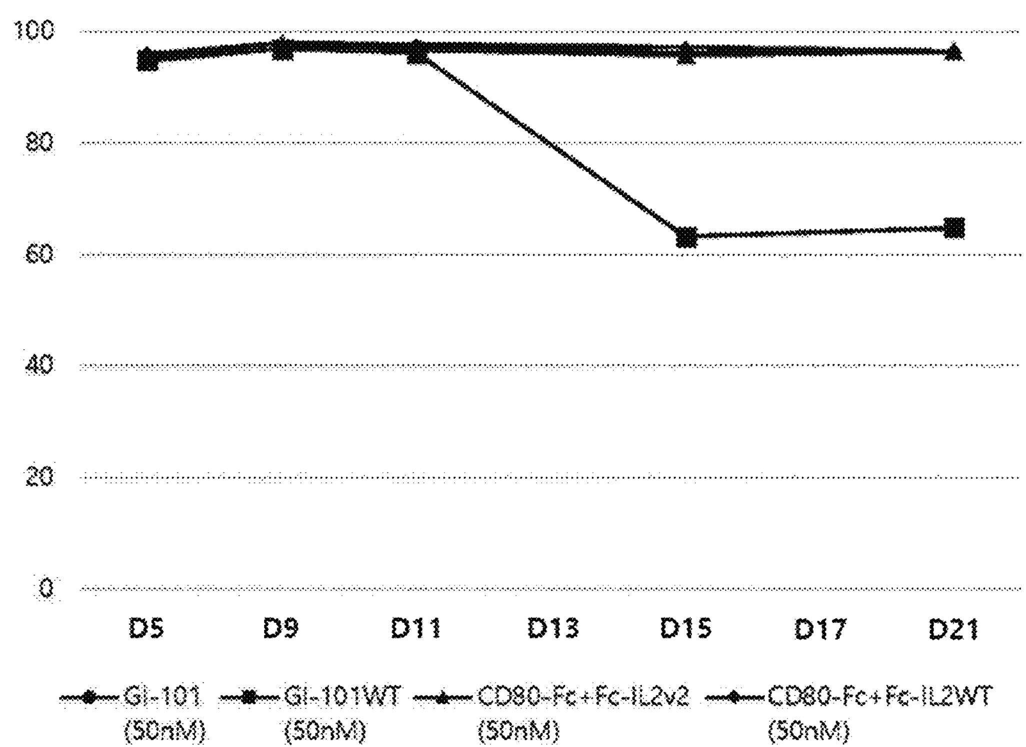
FIGS. 12A and 12B show the viability of NK cells when cultured in an NK MACS (5% hABS) condition.
Figure 12B:
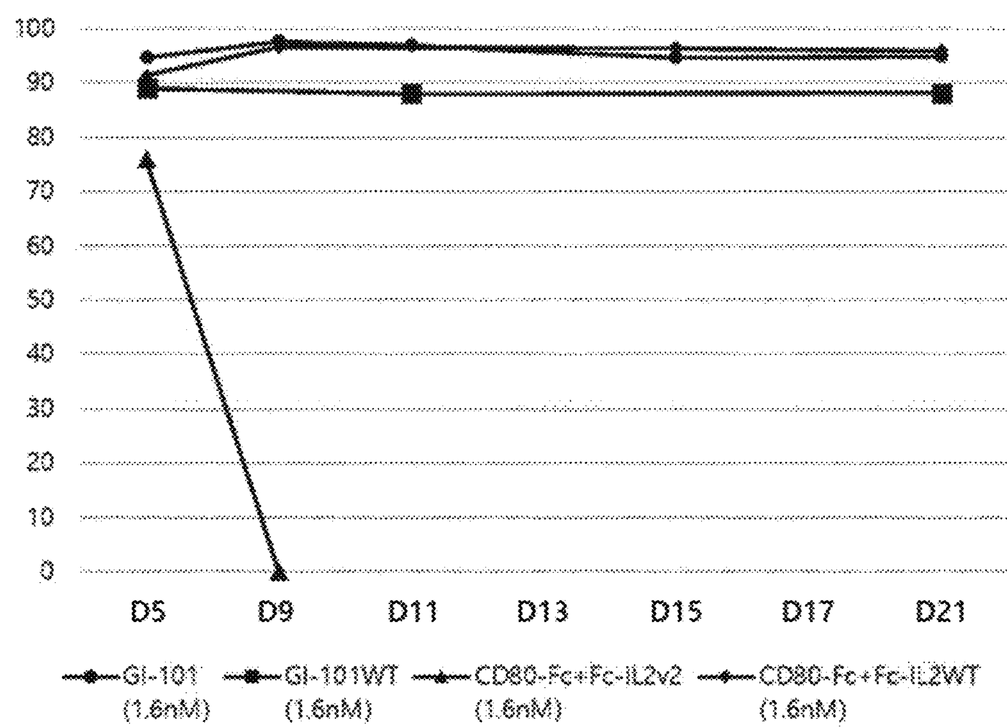
Figure 13:
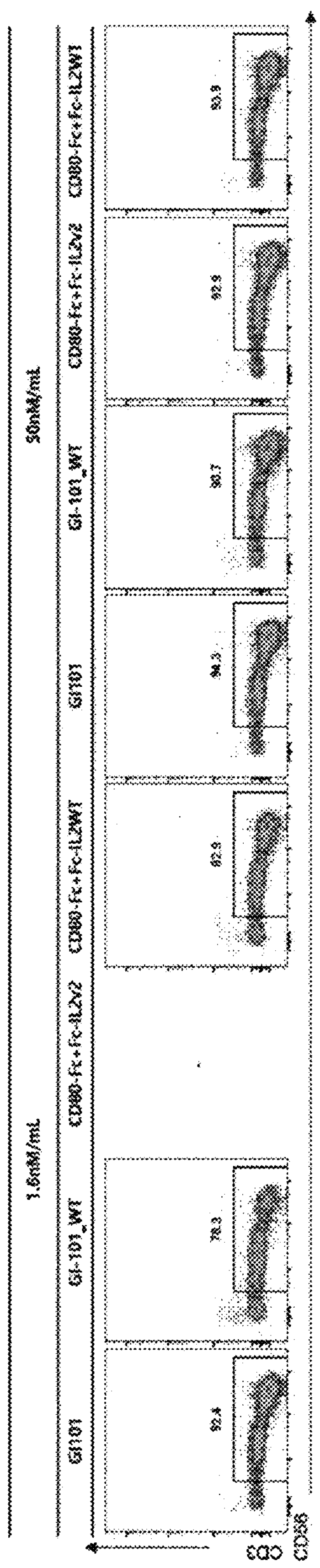
FIG. 13 shows the result of FACS analysis confirming the purity of natural killer cells cultured in a composition containing an AIM-V (5% SR) medium.
Figure 14:
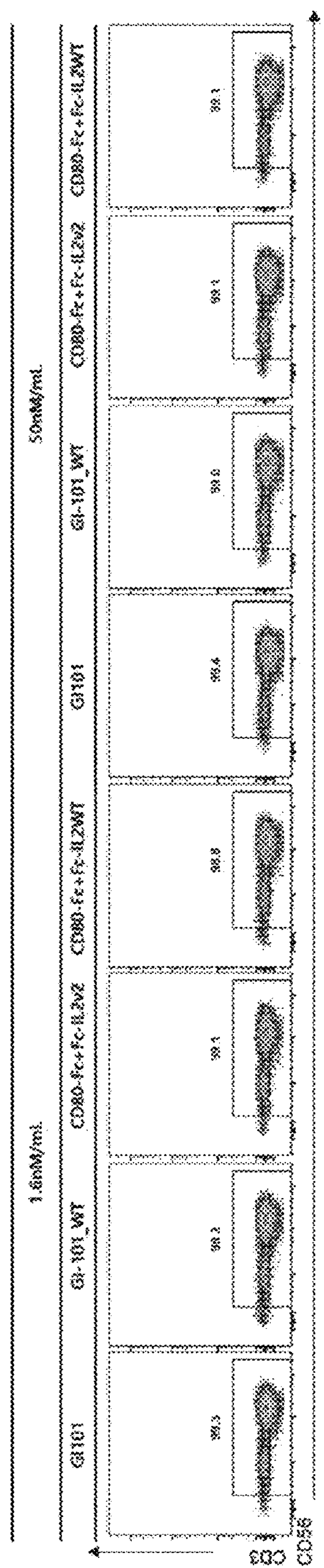
FIG. 14 shows the result of FACS analysis confirming the purity of natural killer cells cultured in a composition containing an AIM-V (5% hABS) medium.
Figure 15:
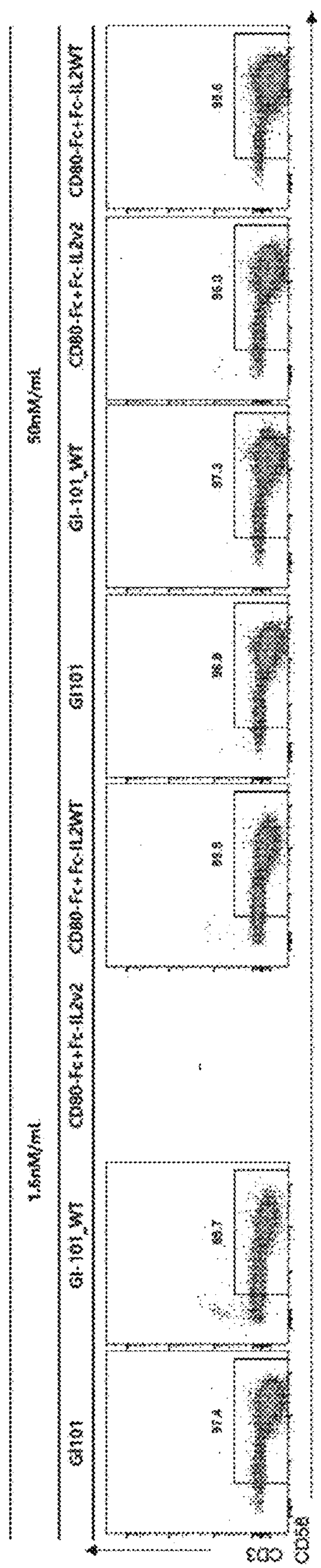
FIG. 15 shows the result of FACS analysis confirming the purity of natural killer cells cultured in a composition containing an X-VIVO15 (5% hABS) medium.
Figure 16:
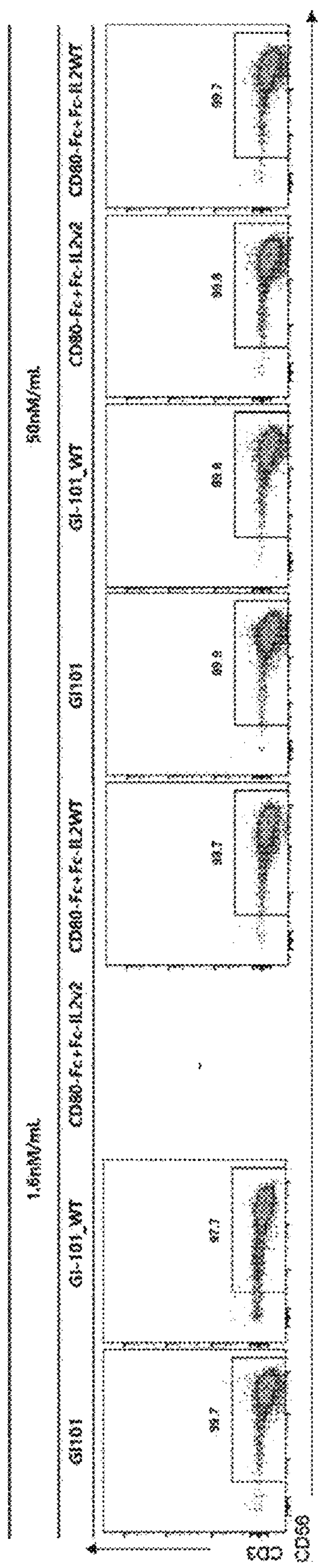
FIG. 16 shows the result of FACS analysis confirming the purity of natural killer cells cultured in a composition containing an NK MACS (5% hABS) medium.
Figure 17:
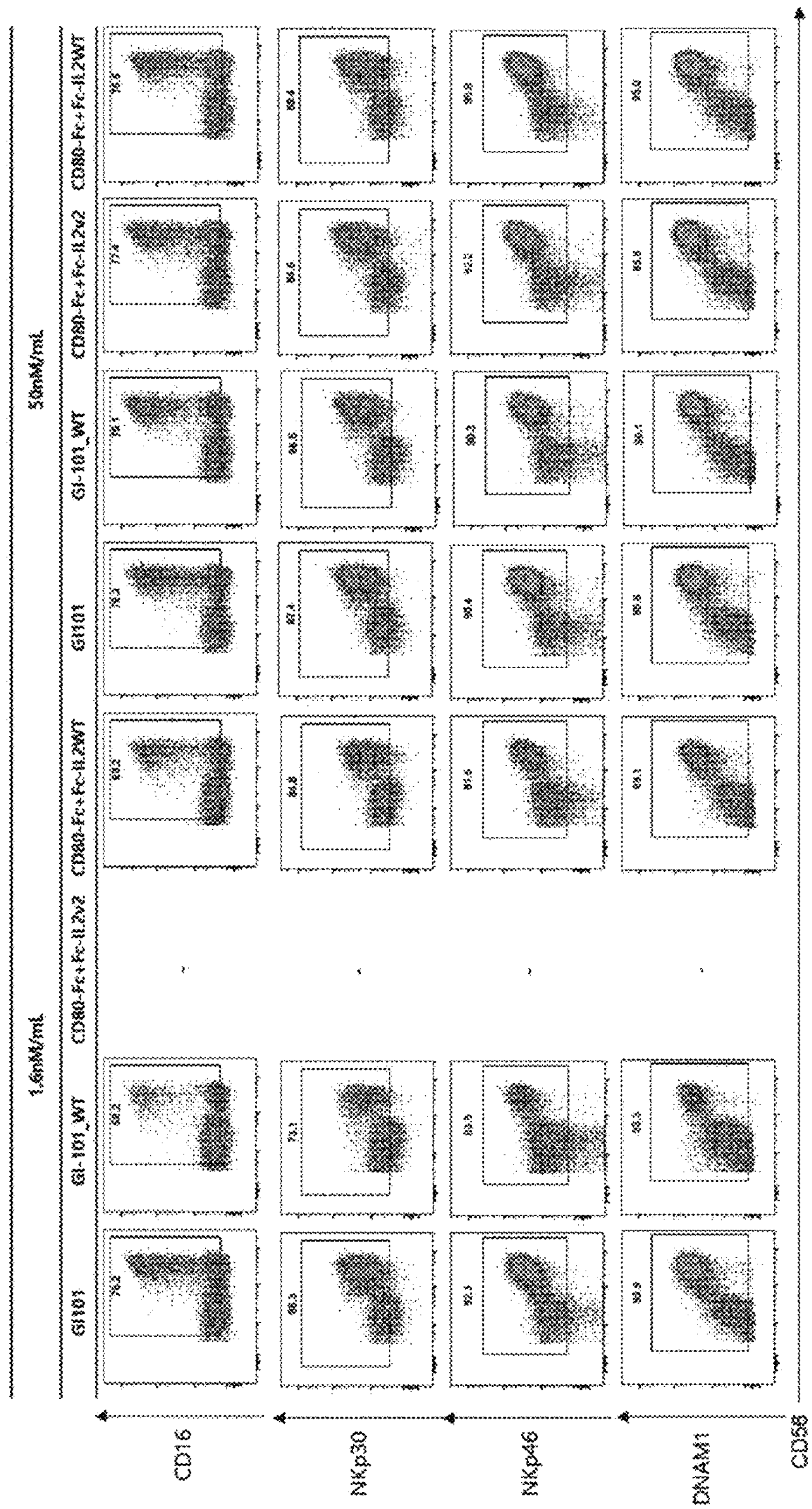
FIG. 17 shows the analysis result for activation markers of natural killer cells cultured in a composition containing an AIM-V (5% SR) medium.
Figure 18:
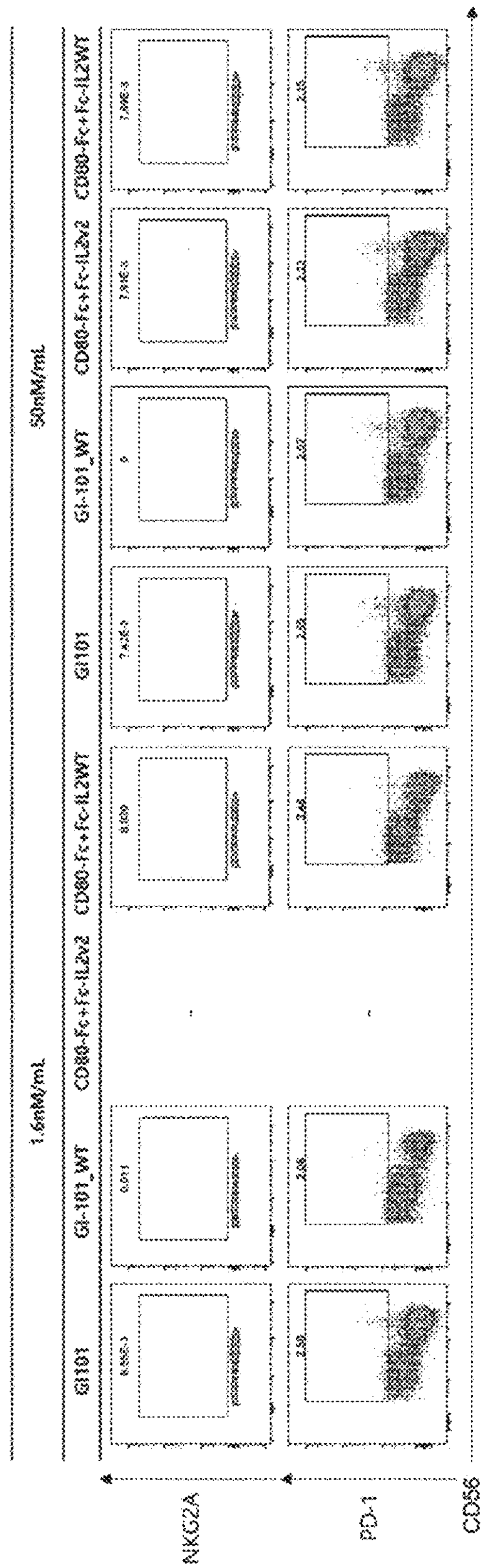
FIG. 18 shows the analysis result for inhibition markers of natural killer cells cultured in a composition containing an AIM-V (5% SR) medium.
Figure 19:
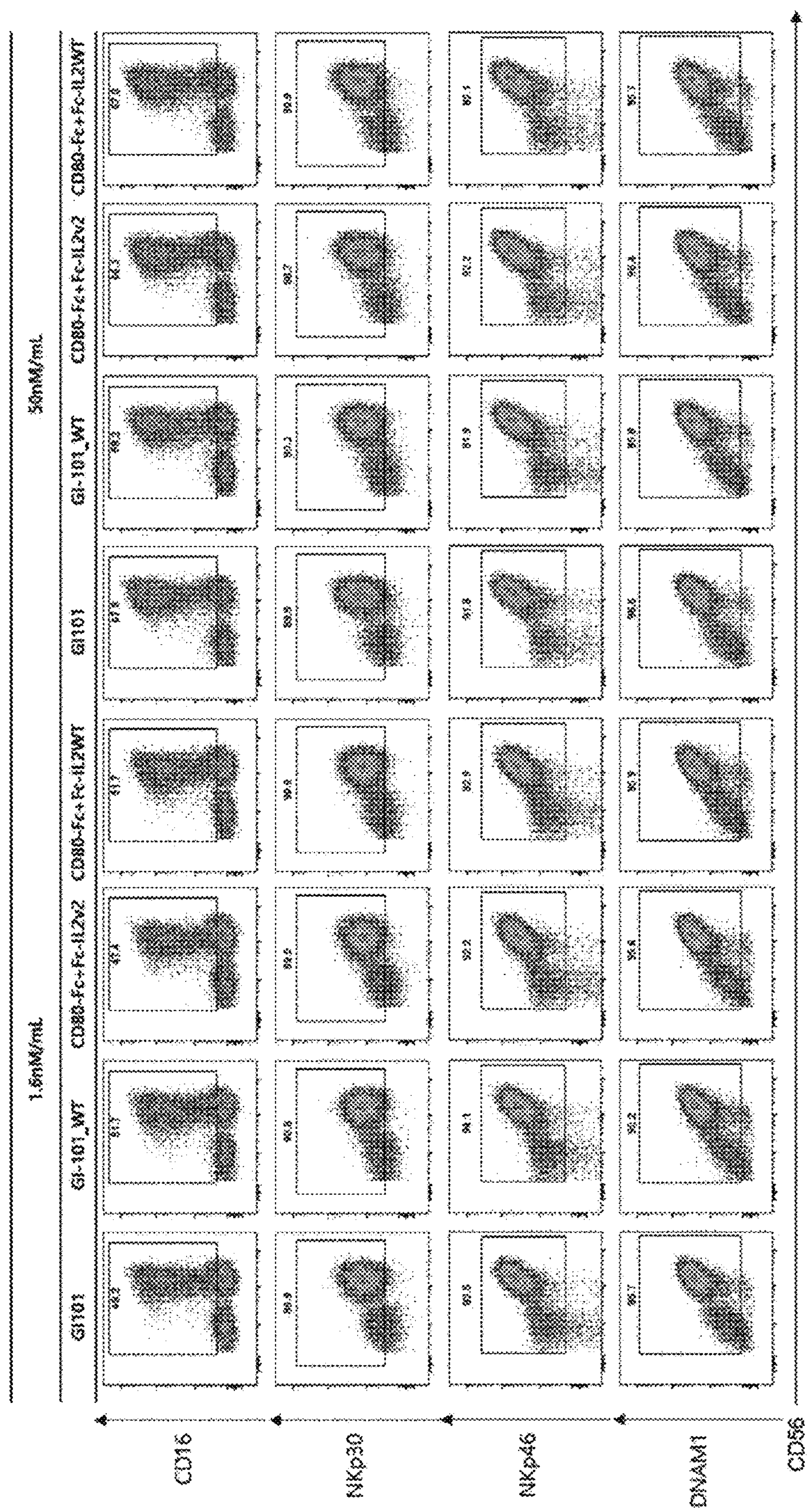
FIG. 19 shows the analysis result for activation markers of natural killer cells cultured in a composition containing an AIM-V (5% hABS) medium.
Figure 20:
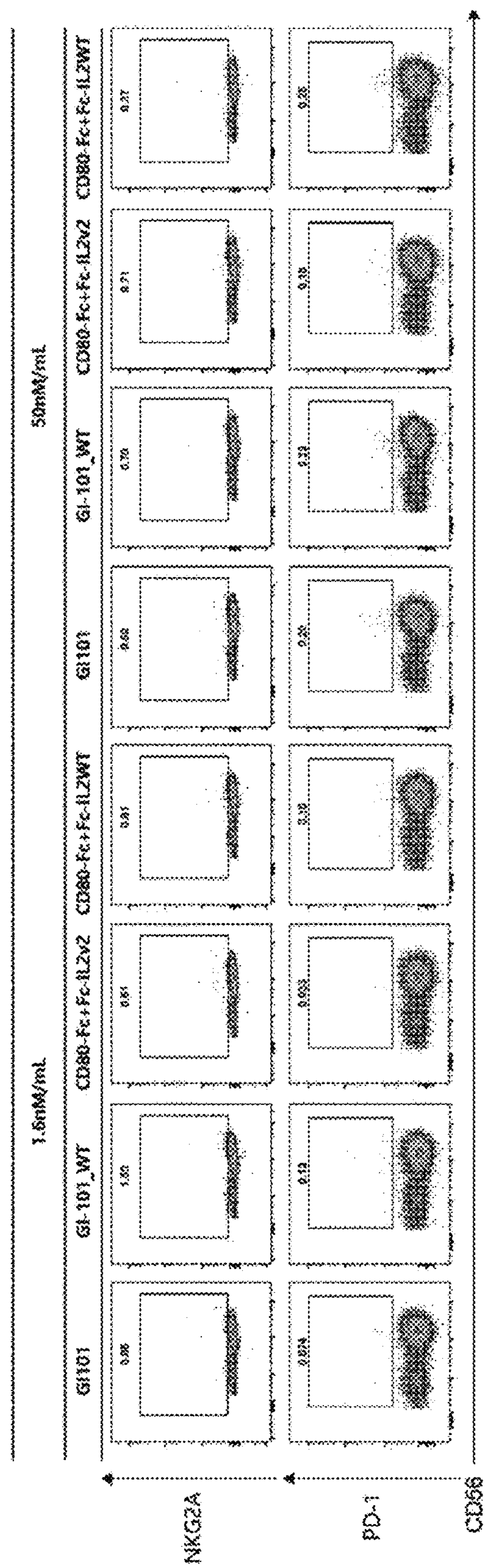
FIG. 20 shows the analysis result for inhibition markers of natural killer cells cultured in a composition containing an AIM-V (5% hABS) medium.
Figure 21:
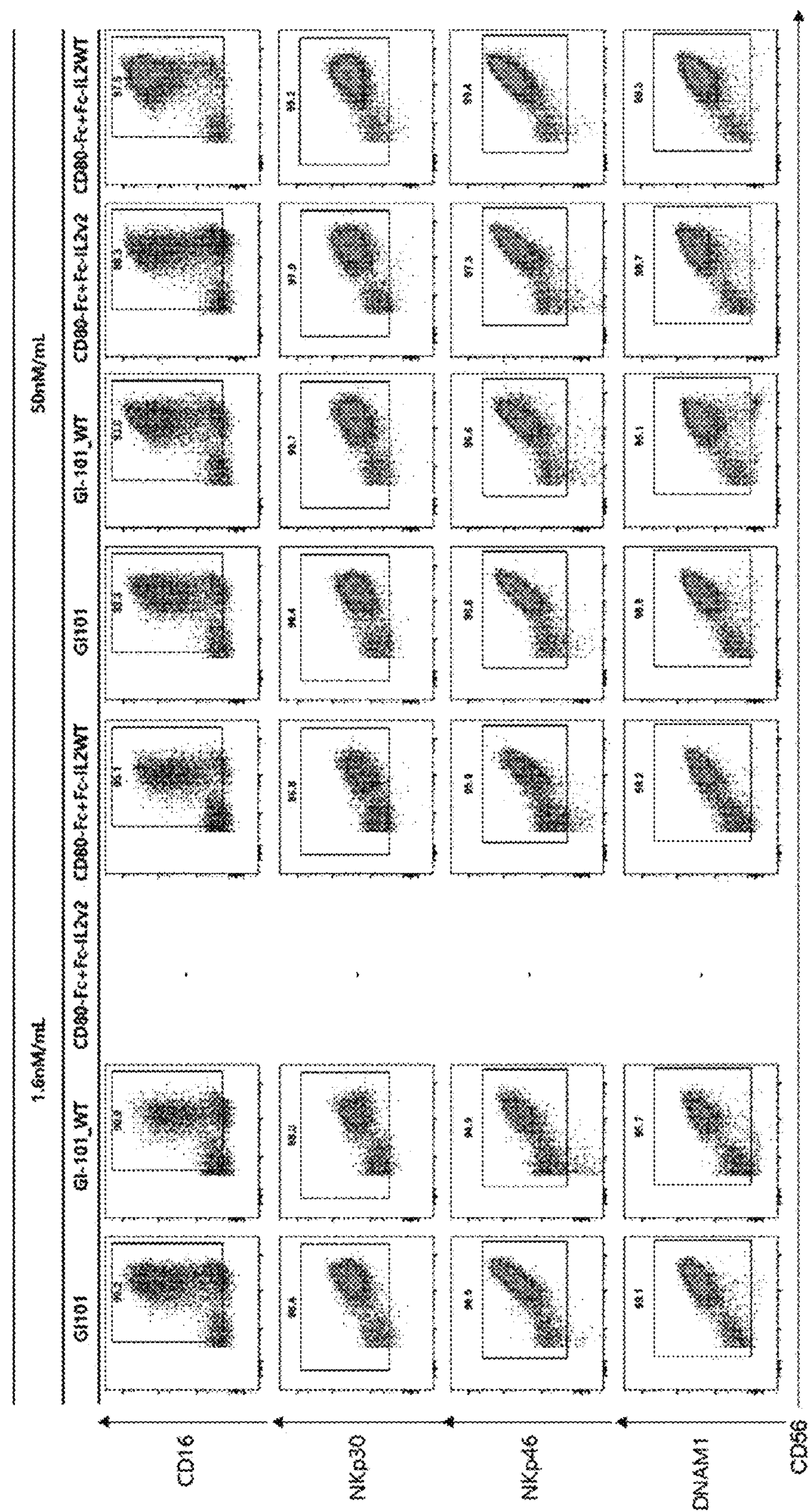
FIG. 21 shows the analysis result for activation markers of natural killer cells cultured in a composition containing an X-VIVO (5% hABS) medium.
Figure 22:
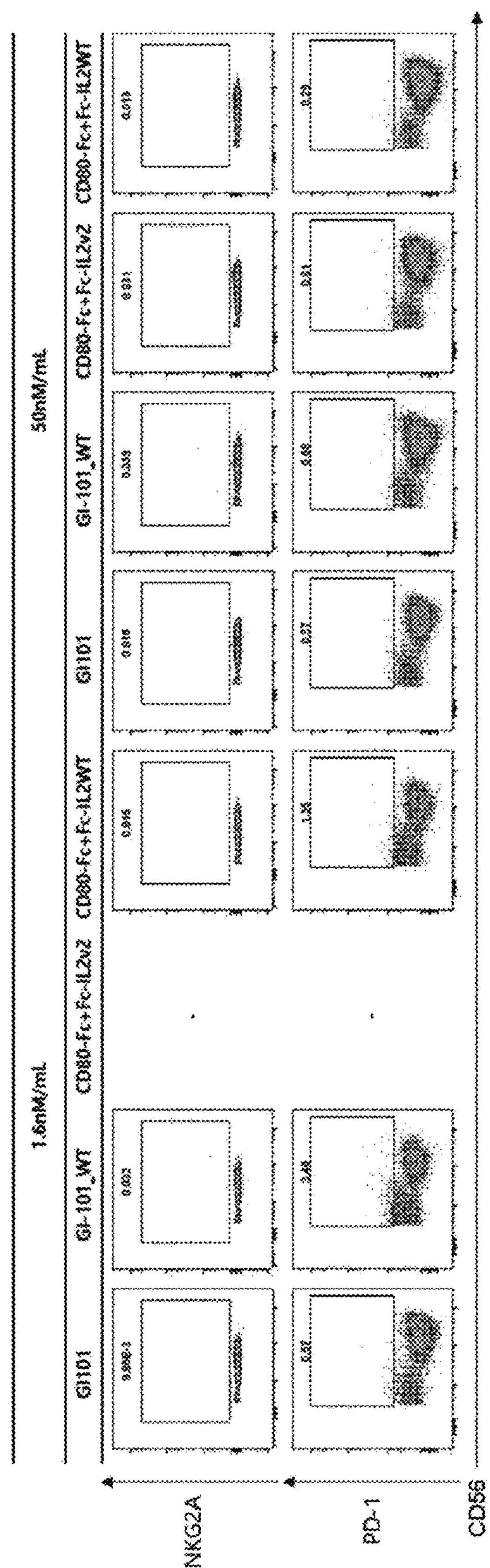
FIG. 22 shows the analysis result for inhibition markers of natural killer cells cultured in a composition containing an X-VIVO (5% hABS) medium.
Figure 23:
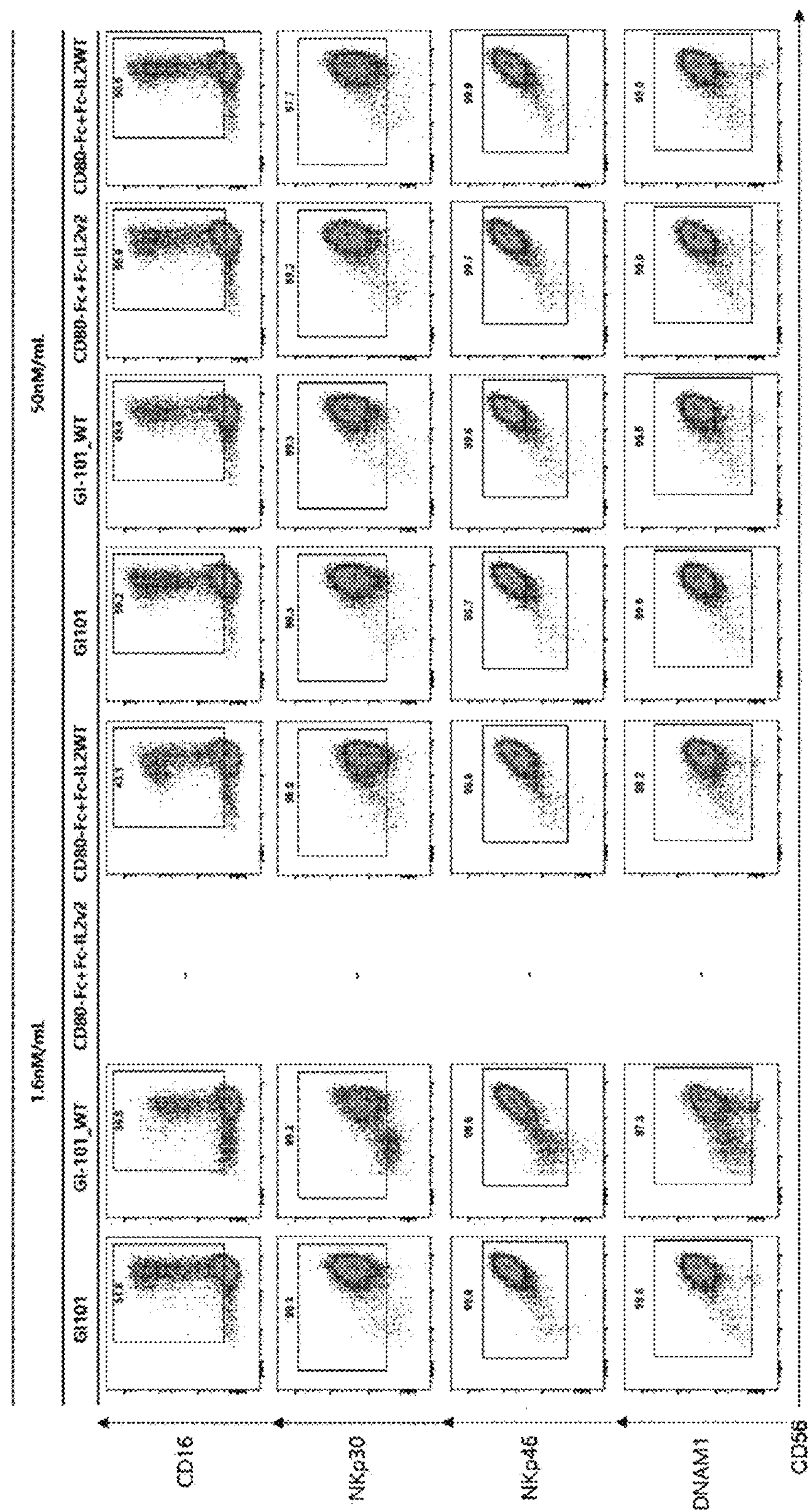
FIG. 23 shows the analysis result for activation markers of natural killer cells cultured in a composition containing an NK MACS (5% hABS) medium.
Figure 24:
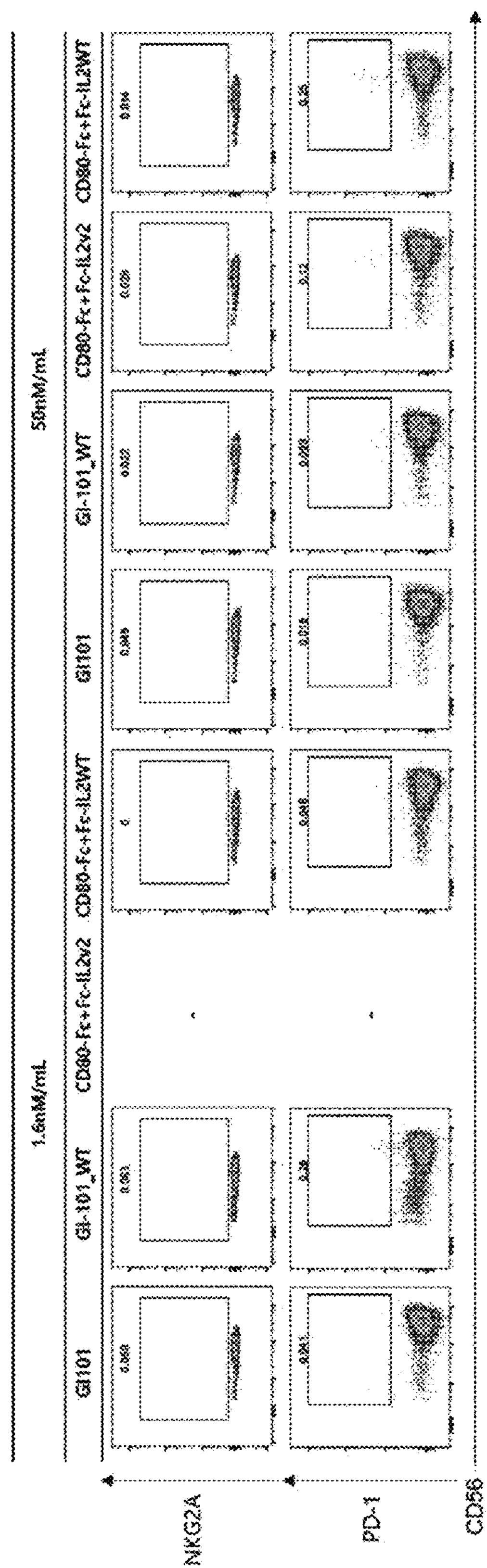
FIG. 24 shows the analysis result for inhibition markers of natural killer cells cultured in a composition containing an NK MACS (5% hABS) medium.
Figure 25:
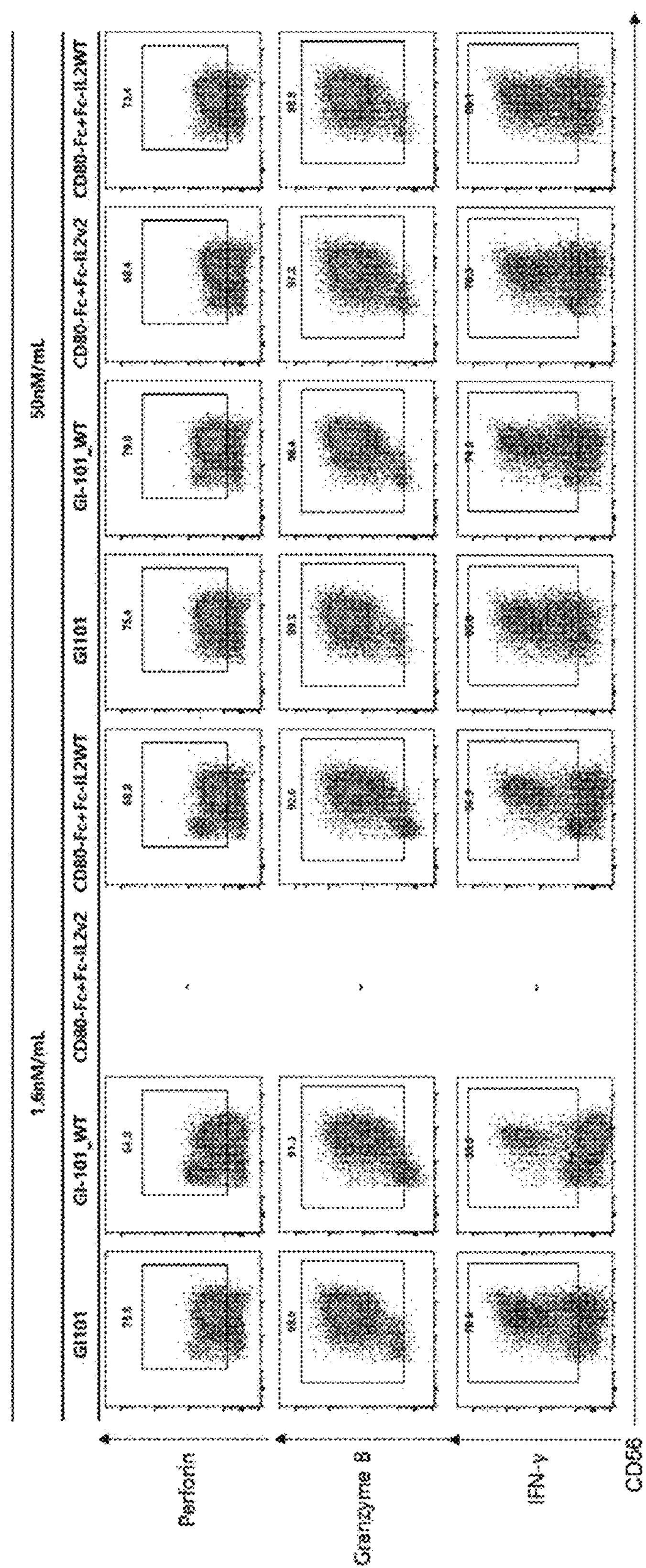
FIG. 25 shows the analysis result for cytotoxicity markers of natural killer cells cultured in a composition containing an AIM-V (5% SR) medium.
Figure 26:
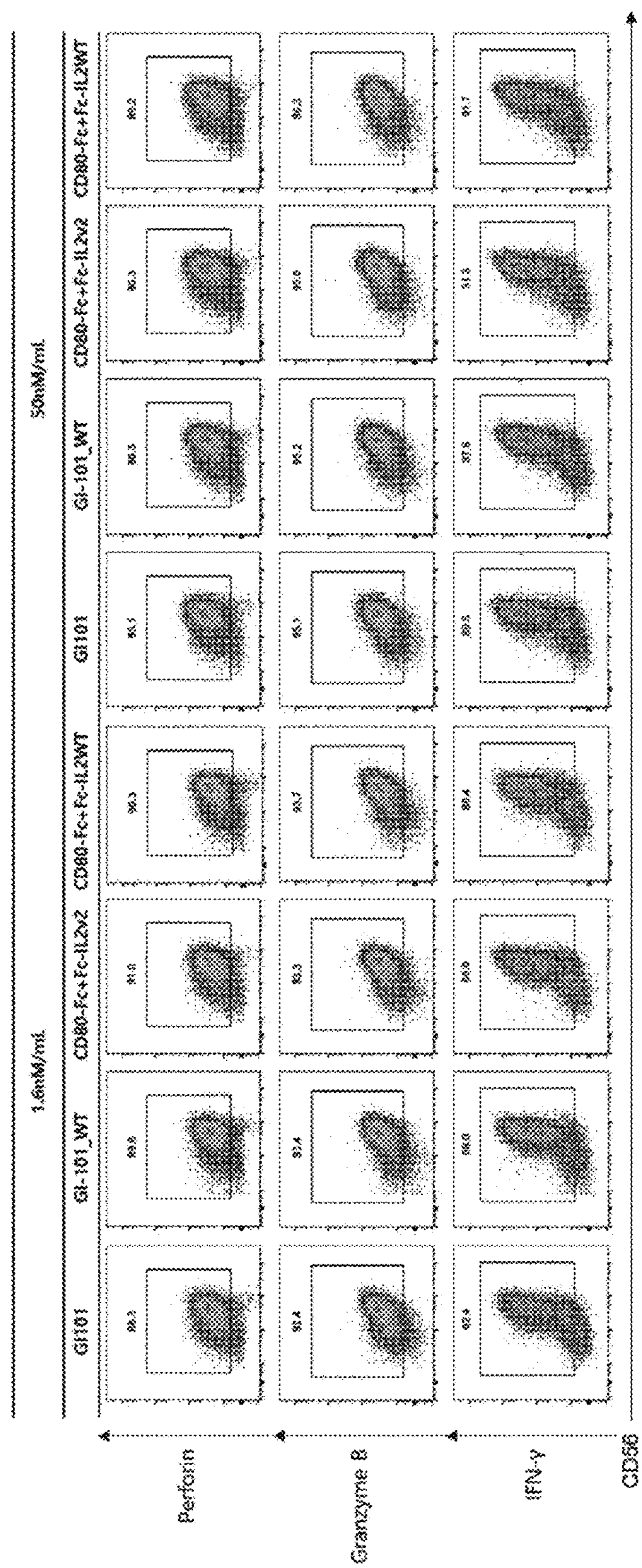
FIG. 26 shows the analysis result for cytotoxicity markers of natural killer cells cultured in a composition containing an AIM-V (5% hABS) medium.
Figure 27:
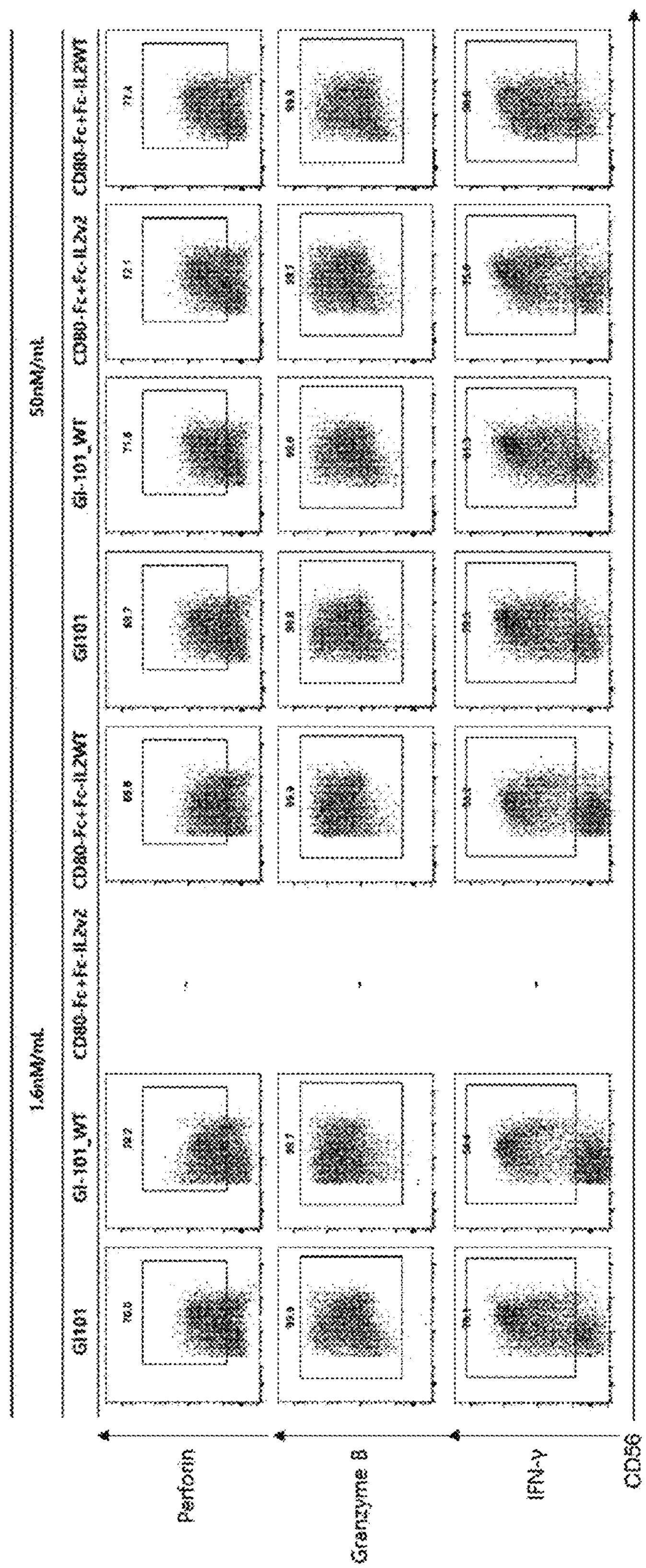
FIG. 27 shows the analysis result for cytotoxicity markers of natural killer cells cultured in a composition containing an X-VIVO15 (5% hABS) medium.
Figure 28:
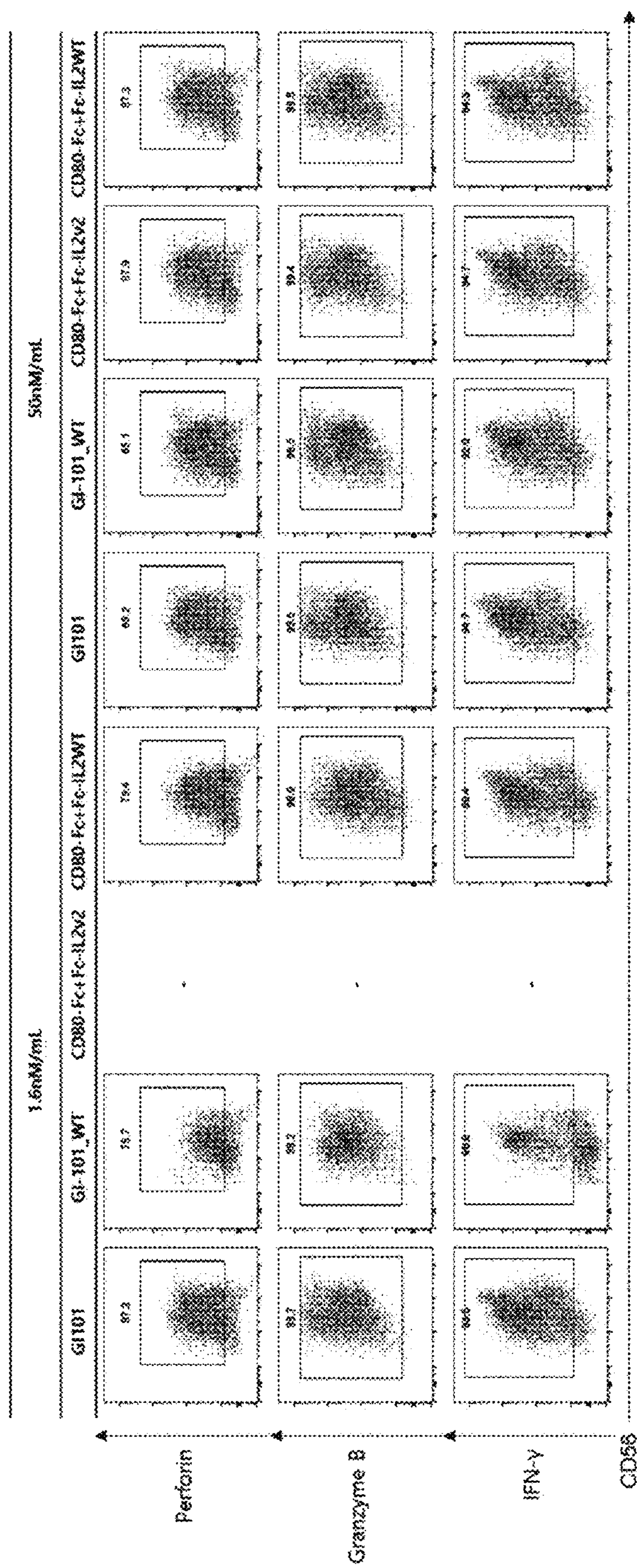
FIG. 28 shows the analysis result for cytotoxicity markers of natural killer cells cultured in a composition containing an NK MACS (5% hABS) medium.
Figure 29:
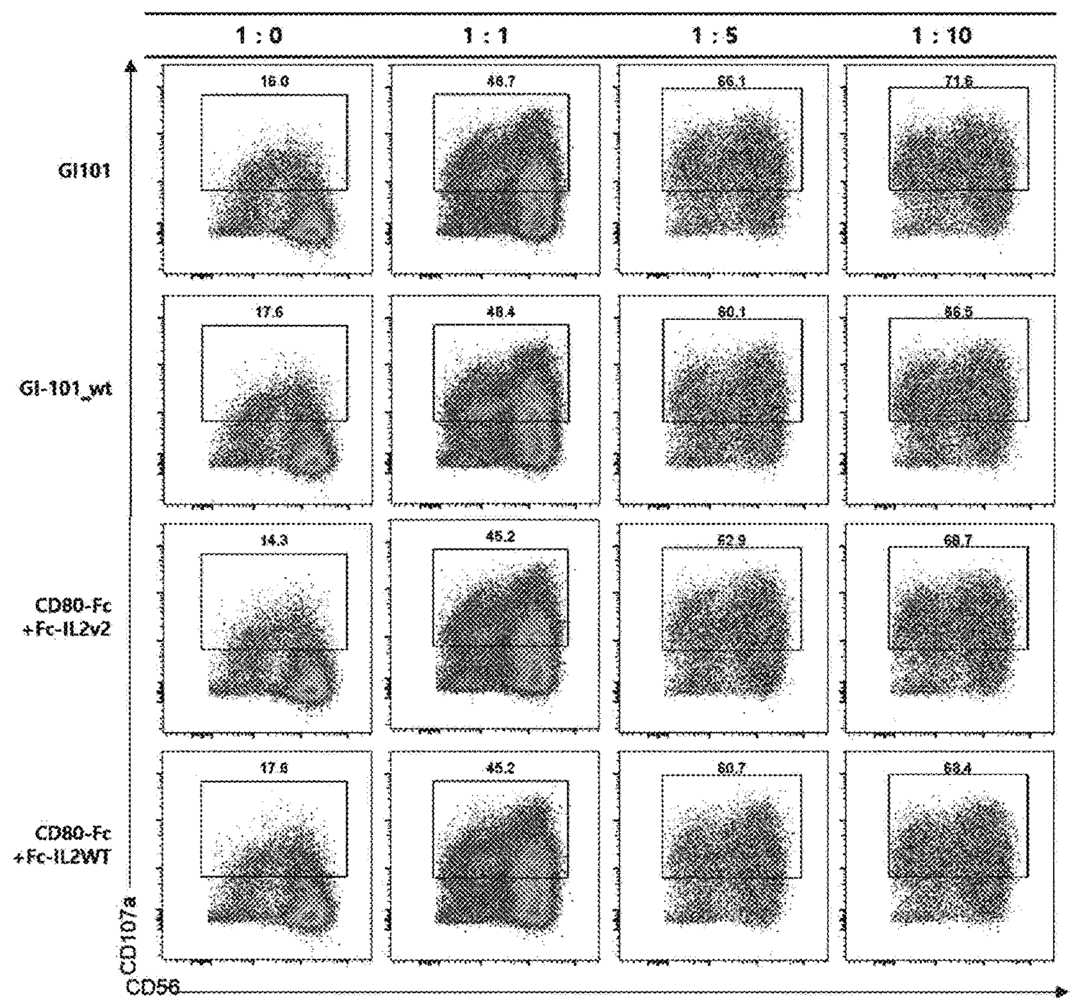
FIG. 29 shows the results of analyzing the degranulation ability of natural killer cells cultured for 21 days in a composition containing GI-101 (50 nM), GI-101_wt (50 nM), CD80-Fc (50 nM)+Fc-IL2v2 (50 nM), or CD80-Fc (50 nM)+Fc-IL2 wt (50 nM) in an AIM-V (5% hABS) medium.
Figure 30:
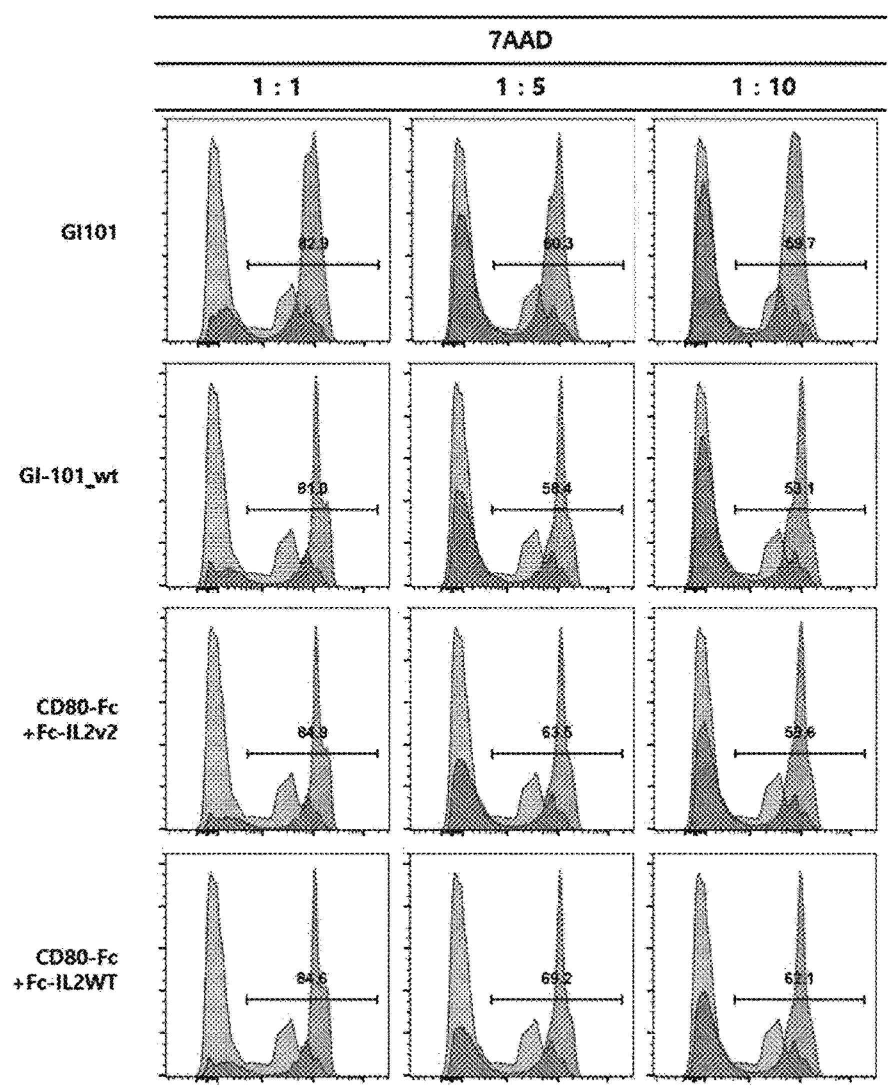
FIG. 30 shows the results of analyzing the cancer cell-killing effect of natural killer cells cultured for 21 days against in a composition containing GI-101 (50 nM), GI-101_wt (50 nM), CD80-Fc (50 nM)+Fc-IL2v2 (50 nM), or CD80-Fc (50 nM)+Fc-IL2 wt (50 nM) in an AIM-V (5% hABS) medium.
Figure 31:
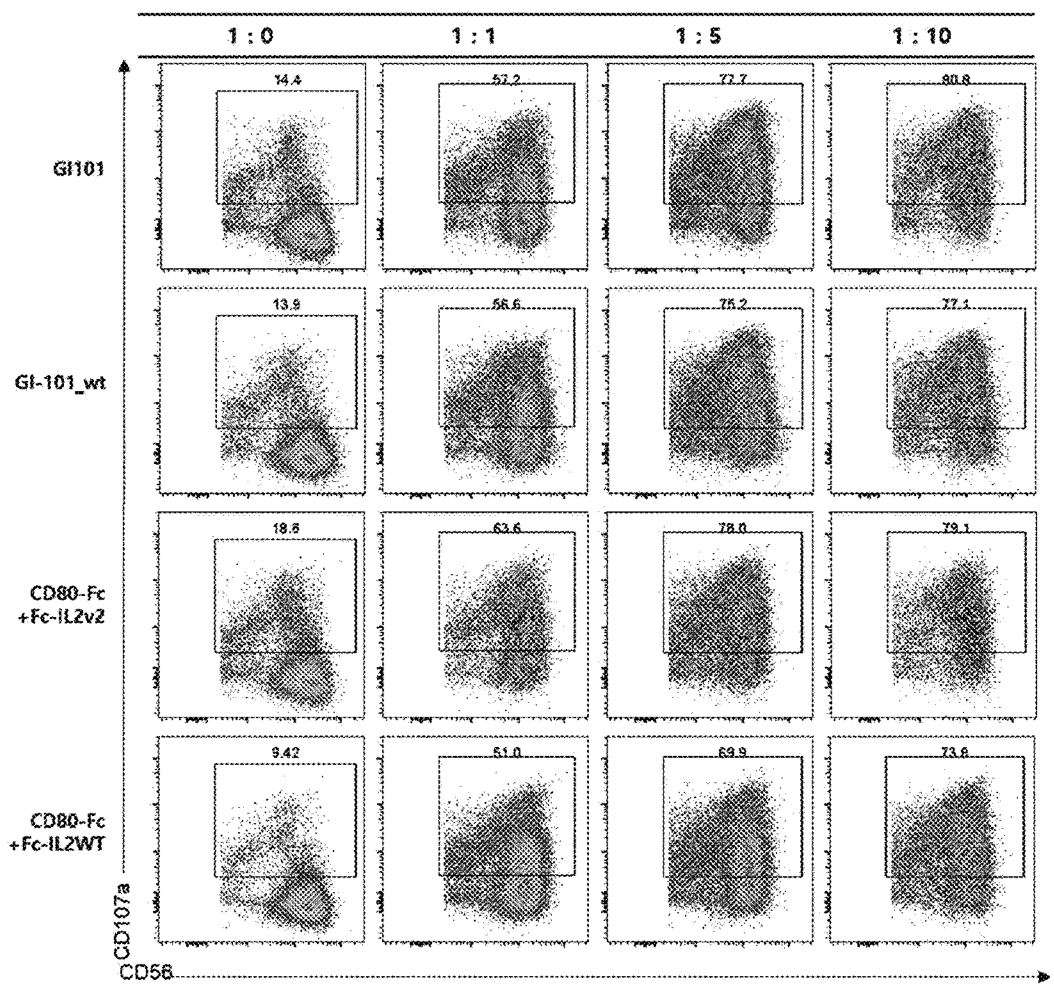
FIG. 31 shows the results of analyzing the degranulation ability of natural killer cells cultured for 21 days in a composition containing GI-101 (50 nM), GI-101_wt (50 nM), CD80-Fc (50 nM)+Fc-IL2v2 (50 nM), or CD80-Fc (50 nM)+Fc-IL2 wt (50 nM) in an X-VIVO15 (5% hABS) medium.
Figure 32:
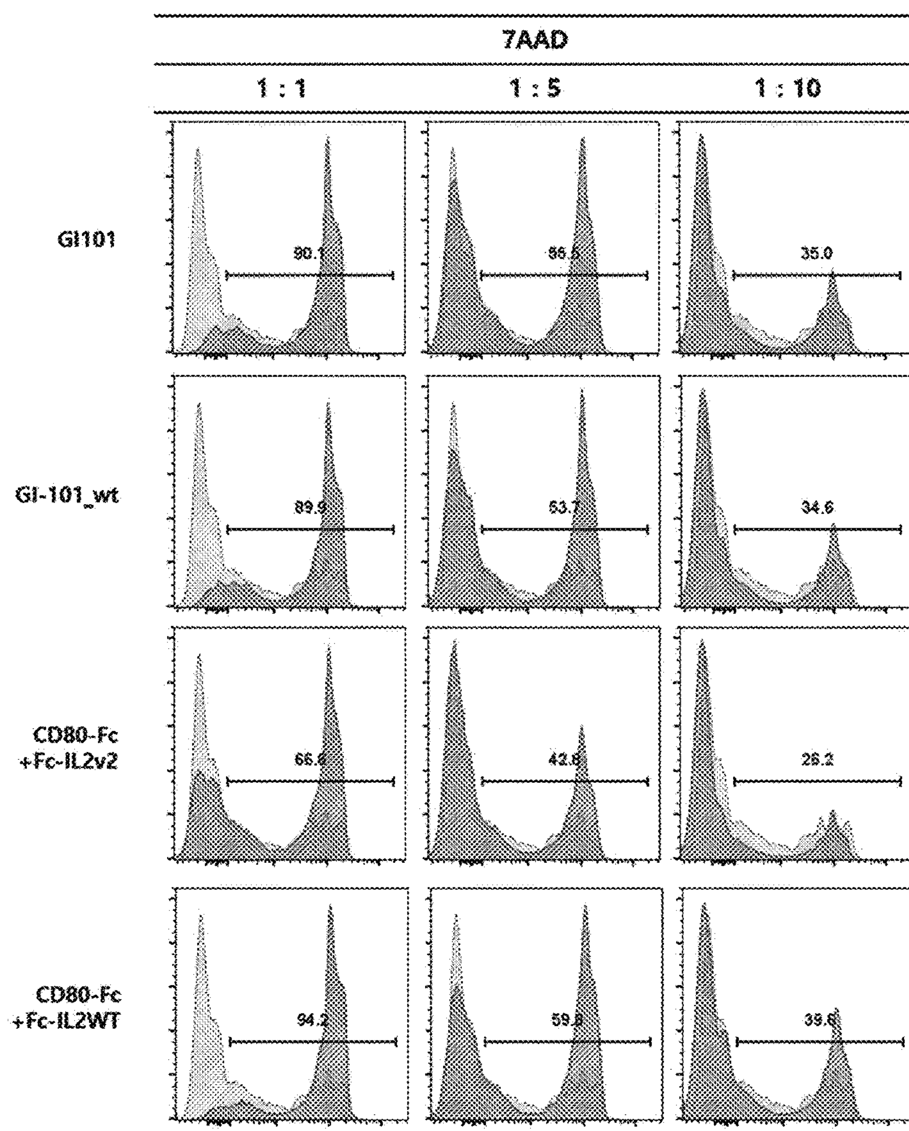
FIG. 32 shows the results of analyzing the cancer cell-killing effect of natural killer cells cultured for 21 days in a composition containing GI-101 (50 nM), GI-101_wt (50 nM), CD80-Fc (50 nM)+Fc-IL2v2 (50 nM), or CD80-Fc (50 nM)+Fc-IL2 wt (50 nM) in an X-VIVO15 (5% hABS) medium.
Figure 33:
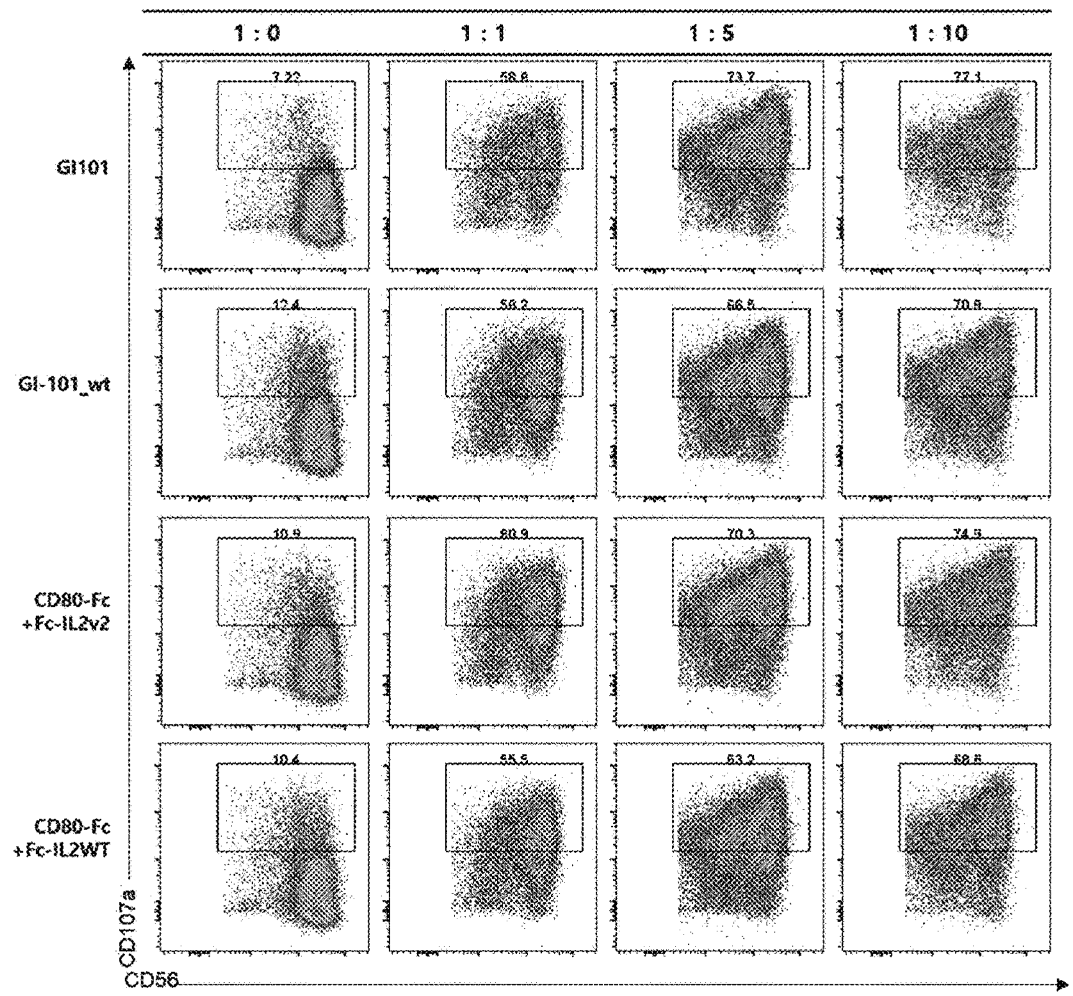
FIG. 33 shows the results of analyzing the degranulation ability of natural killer cells cultured for 21 days in a composition containing GI-101 (50 nM), GI-101_wt (50 nM), CD80-Fc (50 nM)+Fc-IL2v2 (50 nM), or CD80-Fc (50 nM)+Fc-IL2 wt (50 nM) in an NK MACS (5% hABS) medium.
Figure 34:
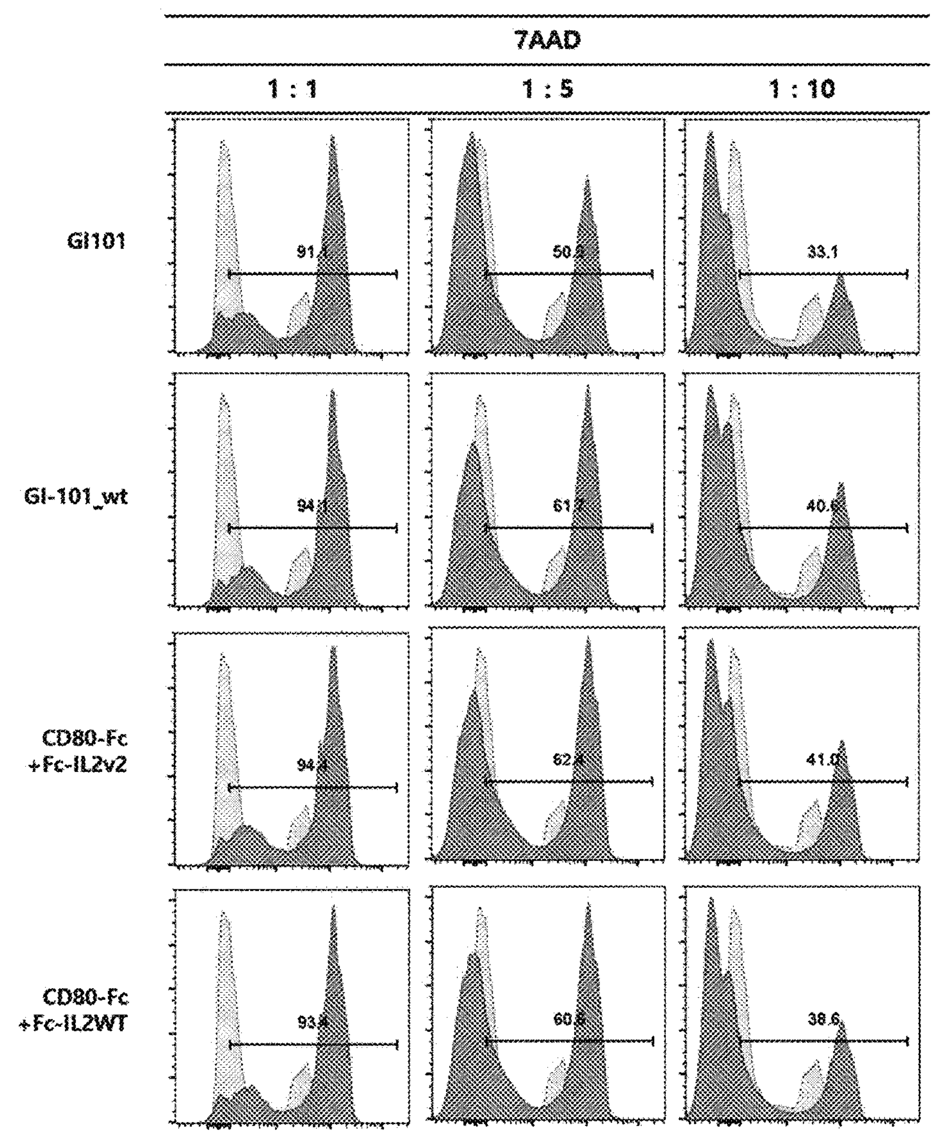
FIG. 34 shows the results of analyzing the cancer cell-killing effect of natural killer cells cultured for 21 days in a composition containing GI-101 (50 nM), GI-101_wt (50 nM), CD80-Fc (50 nM)+Fc-IL2v2 (50 nM), or CD80-Fc (50 nM)+Fc-IL2 wt (50 nM) in an NK MACS (5% hABS) medium.

Then, absorbance at a wavelength of 280 nm over time was measured by using size exclusion chromatography with a TSKGEL® G3000SWXL chromatography column (TOSOH Bioscience) to obtain a high concentration of fusion protein. At this time, the isolated and purified fusion protein was subjected to SDS-PAGE under the reducing (R) or non-reducing (NR) conditions, and stained with coomassie blue to confirm its purity (FIG. 4A). As a result, it was confirmed that the fusion protein forms a dimer. Also, the result analyzed using size exclusion chromatography is as shown in FIG. 4B.

Preparatory Example 5. Preparation of a hCD80-Fc Dimer: hCD80-Fc

In order to produce a fusion protein comprising a human CD80 fragment and a Fc domain, a polynucleotide (SEQ ID NO: 39) including a nucleotide sequence encoding a fusion protein comprising a signal peptide (SEQ ID NO: 1), a CD80 fragment (SEQ ID NO: 2), a linker-conjugated Ig hinge (SEQ ID NO: 3), and a Fc domain (SEQ ID NO: 4) in this order from N-terminus was synthesized through Invitrogen GENEART® Gene Synthesis service of ThermoFisher Scientific Inc., and cloned into a pcDNA3_4 vector. In addition, the vector was introduced into CHO cells (EXPI-CHO™) to express a fusion protein of SEQ ID NO: 40. After introducing the vector, the cells were cultured in an environment of 37° C., 125 RPM, and 8% $CO_2$ for 7 days, and then collected to purify a fusion protein dimer. The purified fusion protein dimer was named "hCD80-Fc."

Purification was performed using chromatography including MABSELECT SURE® protein A resin (Cytiva Bioprocess R&D AB, Uppsala, Sweden). The fusion protein was bound under the condition of 25 mM Tris, 25 mM NaCl, and pH 7.4. Then, it was eluted with 100 mM NaCl and 100 mM acetic acid at pH 3. After putting 20% of 1 M Tris-HCl at pH 9 into a collection tube, the fusion protein was collected. The collected fusion protein was dialyzed into PBS buffer for 16 hours to change.

Figure 2A:
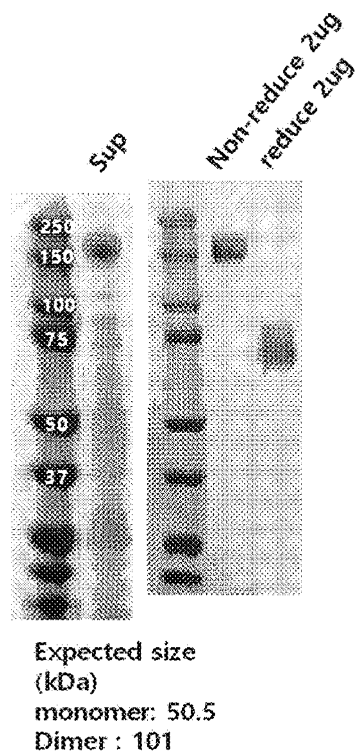
FIG. 2A shows images of SDS-PAGE confirming the obtained hCD80-Fc fusion protein dimer.
Figure 2B:
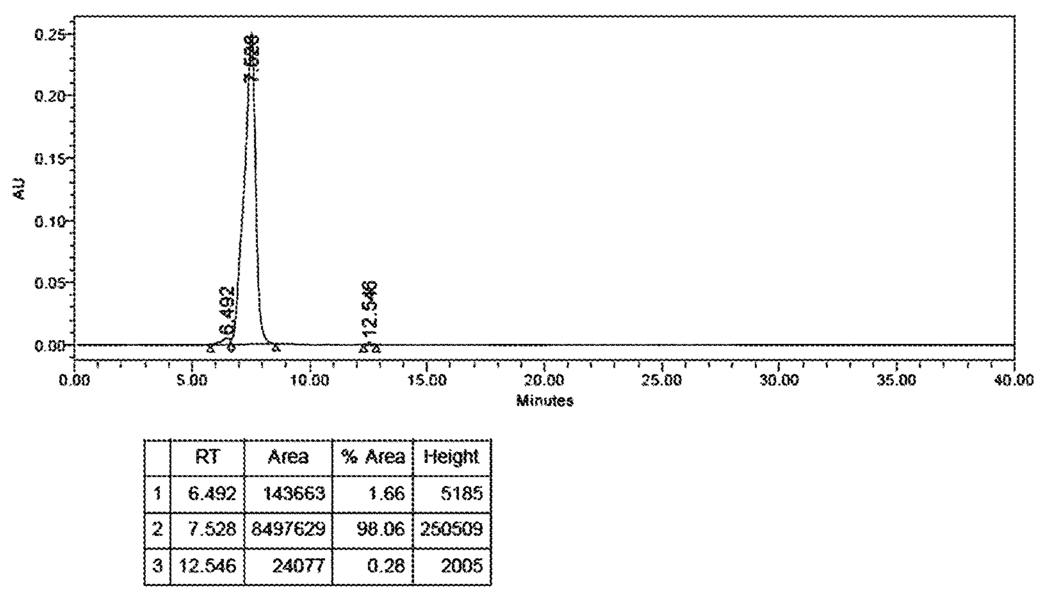
FIG. 2B shows results of size exclusion chromatography (SEC) analysis of the obtained hCD80-Fc fusion protein dimer.

Then, absorbance at a wavelength of 280 nm over time was measured by using size exclusion chromatography with a TSKGEL® G3000SWXL chromatography column (TOSOH Bioscience) to obtain a high concentration of fusion protein. At this time, the isolated and purified fusion protein was subjected to SDS-PAGE under the reducing (R) or non-reducing (NR) conditions, and stained with coomassie blue to confirm its purity (FIG. 2A). As a result, it was confirmed that the fusion protein forms a dimer. Also, the result analyzed using size exclusion chromatography is as shown in FIG. 2B.

Preparation Example 1. Preparation of a Natural Killer Cell Culture Medium

Natural killer cell culture media compositions were prepared by respectively adding substances corresponding to the adding conditions 1 to 4 of Table 5 to each basal culture medium having composition of Table 1 to Table 4 below.

TABLE 1

| Basal culture medium 1 | | | | |
|---|---|---|---|---|
| Components | Manufacturer | Cat. # | Dose | Final concentration |
| CTS ™ Immune Cell SR (Serum replacement) | Thermo | A2596102 | 0.5 ml | 5% |
| GLUTAMAX 100X | GIBCO | A12860-01 | 0.5 ml | 1X |
| rhIL-15 | R&D systems | 247-ILB/CF | adding immediately before use | 66.7 IU |
| rhiL-21 | R&D systems | 8879-IL/CF | adding immediately before use | 0.341 IU |
| anti-CD2/ CD335 Beads | Miltenyi Biotec | 130-094-483 | | |
| OKT3 | Biolegend | 317326 | | 10 ng/mL |
| AIM-V medium | GIBCO | 0870112-DK | to 50 ml | |

TABLE 2

Basal culture medium 2

| Components | Manufacturer | Cat. # | Dose | Final concentration |
|---|---|---|---|---|
| Human AB serum | Sigma | H4522 | 2.5 ml | 5% |
| GLUTAMAX 100X | GIBCO | A12860-01 | 0.5 ml | 1X |
| rhIL-15 | R&D systems | 247-ILB/CF | adding immediately before use | 66.7 IU |
| rhIL-21 | R&D systems | 8879-IL/CF | adding immediately before use | 0.341 IU |
| anti-CD2/ CD335 Beads | Miltenyi Biotec | 130-094-483 | | |
| OKT3 | Biolegend | 317326 | | 10 ng/mL |
| AIM-V medium | GIBCO | 0870112-DK | to 50 ml | |

TABLE 3

Basal culture medium 3

| Components | Manufacturer | Cat. # | Dose | Final concentration |
|---|---|---|---|---|
| Human AB serum | Sigma | H4522 | 2.5 ml | 5% |
| GLUTAMAX 100X | GIBCO | A12860-01 | 0.5 ml | 1X |
| rhIL-15 | R&D systems | 247-ILB/CF | adding immediately before use | 66.7 IU |
| rhIL-21 | R&D systems | 8879-IL/CF | adding immediately before use | 0.341 IU |
| anti-CD2/ CD335 Beads | Miltenyi Biotec | 130-094-483 | | |
| OKT3 | Biolegend | 317326 | | 10 ng/mL |
| X-VIVO ™ 15 Medium | Lonza | 04-418Q | to 50 ml | |

TABLE 4

Basal culture medium 4

| Components | Manufacturer | Cat. # | Dose | Final concentration |
|---|---|---|---|---|
| Human AB serum | Sigma | H4522 | 2.5 ml | 5% |
| NK MACS supplement | Miltenyi Biotec | 130-113-102 | 500 ㎕ | 1% |
| anti-CD2/ CD335 beads | Miltenyi Biotec | 130-094-483 | | |
| OKT3 | Biolegend | 317326 | | 10 ng/mL |
| NK MACS medium | | 130-112-968 | to 50 ml | |

TABLE 5

Adding material

| Classification | Components | Manufacturer | Dose | Final concentration |
|---|---|---|---|---|
| Adding condition 1 | GI-101 | GI-Innovation | adding immediately before use | 1.6 nM/50 nM |
| Adding condition 2 | GI-101WT | GI-Cell | adding immediately before use | 1.6 nM/50 nM |

TABLE 5-continued

| Adding material | | | | |
|---|---|---|---|---|
| Classification | Components | Manufacturer | Dose | Final concentration |
| Adding condition 3 | CD80-Fc + Fc-IL2WT | GI-Cell | adding immediately before use | CD80-Fc (1.6 nM) + Fc-IL2WT (1.6 nM)/ CD80-Fc (50 nM) + Fc-IL2WT (50 nM) |
| Adding condition 4 | CD80-Fc + Fc-IL2v2 | GI-Cell | adding immediately before use | CD80-Fc (1.6 nM) + Fc-IL2v2 (1.6 nM)/ CD80-Fc (50 nM) + Fc-IL2v2 (50 nM) |

Example 1. Preparation of CD3(−)CD56(+) Natural Killer Cells Derived from Peripheral Blood Mononuclear Cells (PBMC)

In order to obtain CD3(−) cells, the number of PBMCs (peripheral blood mononuclear cells, Zen-Bio. Inc, NC 27709, USA, Cat #: SER-PBMC-200-F) was counted using an ADAM-MC2 automated cell counter (NanoEnTek, purchased from Cosmo Genetech Co., Ltd.). The PBMCs were transferred to a new tube, and then centrifuged at 300×g for 5 minutes at a temperature of 4° C. 0.5% (v/v) bovine serum albumin (BSA) and EDTA at a concentration of 2 mM were included in PBS to prepare MACS buffer (pH 7.2). After centrifugation was completed, a cell pellet was treated with 80 μl of MACs buffer and 20 μl of CD3 magnetic beads (Miltenyi biotech, 130-050-101) per $1\times10^7$ cells to suspend, and then incubated at a temperature of 4° C. for 15 minutes. 10 ml of MACs buffer was added for washing and centrifuged at 300×g for 10 minutes at a temperature of 4° C., and then the cell pellet was resuspended in 0.5 ml of MACs buffer.

2 ml of MACs buffer was first flowed into the LD column (Miltenyi Biotec, Bergisch Gladbach, Germany, Cat #: 130-042-901), and then the cell suspension was flowed. Then, CD3(−) cells passing through the LD column were obtained. At this time, CD3(−) cells were obtained by flowing 2 ml of MACs buffer three times so that the cells remaining in the LD column could be sufficiently separated. The obtained CD3(−) cells were counted using a cell counter, and then placed in a new tube and centrifuged at 300×g for 5 minutes at a temperature of 4° C. Then, the supernatant was removed, and then 80 μl of MACs buffer and 20 μl of CD56 magnetic beads (Miltenyi biotech, Cat #: 130-050-401) were added per 1×10' cells, followed by incubation at a temperature of 4° C. for 15 minutes. 10 ml of MACs buffer was added for washing and centrifuged at 300×g for 10 minutes at a temperature of 4° C., and then the cell pellet was resuspended in 0.5 ml of MACs buffer.

3 ml of MACs buffer was first flowed into the LS column (Miltenyi Biotec, Bergisch Gladbach, Germany, Cat #: 130-042-901), and then the cell suspension was flowed. At this time, 2 ml of MACs buffer was flowed three times so that the cells remaining in the LS column could be sufficiently separated. Then, after the LS column was separated from a magnet stand, 5 ml of MACs buffer was added, and pressure was applied with a piston to obtain CD3(−)CD56(+) natural killer cells. The obtained CD3(−)CD56(+) natural killer cells was placed in a new tube and centrifuged at 300×g for 5 minutes at a temperature of 4° C. After removing the supernatant, the cells were suspended in the basal culture media shown in Table 1 to Table 4 in consideration of the culture conditions. The number of suspended cells was counted using a cell counter.

Example 2. Culture of CD3(−)CD56(+) Natural Killer Cells Derived from Peripheral Blood Mononuclear Cells (PBMC)

100 μL of CD335 (NKp46)-biotin and 100 μL of CD2-biotin included in a NK Cell Activation/Expansion Kit (Cat #: 130-112-968) (Miltenyi Biotec, Bergisch Gladbach, Germany) were placed in a 1.5 mL microtube and mixed, and then 500 μL of Anti-Biotin MACSiBead Particles was added and mixed. Then, 300 μL of MACs buffer was added, and mixed at 2° C. to 8° C. for 2 hours using a microtube rotator. Considering the number of cells, 5 μL of NK activation beads per $1\times10^6$ cells was transferred to a new tube. 1 mL of PBS was added and centrifuged at 300×g for 5 minutes. After removing the supernatant, NK MACs medium (Cat #: 130-094-483) (Miltenyi Biotec, Bergisch Gladbach, Germany) to be used was added on the basis of μL per $10^6$ NK cells, and released beads, followed by inoculating into the CD3(−)CD56(+) natural killer cells isolated in Example 1.

Next, the prepared CD3(−)CD56(+) natural killer cells were suspended in a culture medium composition containing an additive prepared in Preparation example 1 so that the total number of cells was $2.5\times10^5$, and seeded in a 48-well plate, followed by culturing under the condition of 37° C. and 5% $CO_2$. Then, the number of cells was determined every 2 days to subculture in the order of a 48-well plate, a 24-well plate, a 12-well plate, a 6-well plate, and a 25T flask when the cells were confluent 80% or more of culture vessel (confluency), and finally all cells were harvested on day 21.

Example 3. Counting of Cell Number and Comparison of Cell Viability

The total number of cells and viability of the cultured natural killer cells were counted using a cell counter (ADAM-MC2) on days 5, 9, 11, 13, 15, 17, and 21. At this time, the number of cells were counted on the dates above as the cells reach 80% confluency which is a criterion for subculture because the proliferation rate of cells varies depending on a treated material and type of culture medium.

The results of comparing the total number of cells and viability of CD3-CD56+ cells cultured under the conditions of the culture medium composition prepared in Preparation example 1 are shown in Tabled 6 to 13, and FIGS. 5A to 12B.

As a result, it was confirmed that all culture media compositions to which GI-101 prepared by Preparatory example 1 was added had the total number of natural killer cells greater than the control group (addition of CD80-Fc+Fc-IL2v2 or CD80-Fc+Fc-IL2WT), regardless of the treatment concentration in four basal culture medium conditions (Tables 1 to 4) (FIGS. 5A, 5B, 7A, 7B, 9A, 9B, 11A and 11B).

In addition, even for cells viability, when GI-101 was added, all culture media compositions exhibited high viability regardless of the basal culture medium and the concentration (FIGS. 6A, 6B, 8A, 8B, 10A, 10B, 12A and 12B).

Based on the results, it was confirmed that GI-101 plays an important role in improving proliferation ability and viability of natural killer cells as compared with the control group (addition of CD80-Fc+Fc-IL2v2 or CD80-Fc+Fc-IL2WT), regardless of the basal culture medium and the concentration.

TABLE 6

| TOTAL CELL NUMBER (×10$^5$) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| Table 1 | 50 nM | GI-101 | 2.50 | 3.17 | 8.56 | — | 23.84 | — | 27.38 | 23.76 |
| | | GI-101WT | 2.50 | 2.36 | 6.40 | — | — | — | 15.45 | 13.33 |
| | | CD80-Fc + Fc-IL2v2 | 2.50 | 2.62 | 6.61 | — | 16.16 | — | 21.93 | 13.19 |
| | | CD80-Fc + Fc-IL2WT | 2.50 | 1.87 | — | 11.04 | 13.92 | — | 17.86 | 13.33 |
| | 1.6 nM | GI-101 | 2.50 | 2.27 | 6.79 | — | 13.98 | — | 15.62 | 11.19 |
| | | GI-101WT | 2.50 | 1.92 | 4.65 | — | — | — | — | 3.58 |
| | | CD80-Fc + Fc-IL2v2 | 2.50 | 0.23 | — | — | — | — | — | — |
| | | CD80-Fc + Fc-IL2WT | 2.50 | 1.76 | — | — | 6.96 | — | 6.64 | 4.46 |

TABLE 7

| CELL VIABILITY (%) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| Table 1 | 50 nM | GI-101 | — | 76.58 | 82.41 | — | 90.94 | — | 86.68 | 84.19 |
| | | GI-101WT | — | 75.98 | 83.42 | — | — | — | 89.27 | 89.53 |
| | | CD80-Fc + Fc-IL2v2 | — | 78.18 | 81.73 | — | 90.57 | — | 88.76 | 89.64 |
| | | CD80-Fc + Fc-IL2WT | — | 83.64 | — | 86.50 | 92.19 | — | 89.62 | 82.36 |
| | 1.6 nM | GI-101 | — | 75.08 | 82.94 | — | 87.85 | — | 90.34 | 88.22 |
| | | GI-101WT | — | 77.55 | 82.32 | — | — | — | — | 87.01 |
| | | CD80-Fc + Fc-IL2v2 | — | 49.77 | — | — | — | — | — | — |
| | | CD80-Fc + Fc-IL2WT | — | 74.51 | — | — | 86.47 | — | 88.90 | 93.29 |

TABLE 8

| TOTAL CELL NUMBER (×10^5) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| Table 2 | 50 nM | GI-101 | 2.5 | 11.71 | 38.81 | — | 214.88 | 415.25 | — | 694.59 |
| | | GI-101WT | 2.5 | 8.57 | 30.58 | 62.31 | 96.42 | — | — | 152.16 |
| | | CD80-Fc + Fc-IL2v2 | 2.5 | 8.12 | — | — | 90.54 | 122.27 | — | 153.14 |
| | | CD80-Fc + Fc-IL2WT | 2.5 | 7.80 | 29.97 | — | 92.32 | 118.56 | — | 152.23 |
| | 1.6 nM | GI-101 | 2.5 | 5.60 | 28.69 | — | 55.39 | — | — | 94.22 |
| | | GI-101WT | 2.5 | 6.58 | 14.92 | — | 35.18 | — | — | 37.81 |
| | | CD80-Fc + Fc-IL2v2 | 2.5 | 6.02 | 19.85 | — | 56.26 | — | — | 75.83 |
| | | CD80-Fc + Fc-IL2WT | 2.5 | 6.04 | 18.39 | — | 46.50 | — | — | 55.51 |

TABLE 9

| CELL VIABILITY (%) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| Table 2 | 50 nM | GI-101 | — | 93.31 | 95.64 | — | 96.47 | 96.58 | — | 93.21 |
| | | GI-101WT | — | 94.38 | 95.45 | 96.06 | 94.96 | — | — | 92.14 |
| | | CD80-Fc + Fc-IL2v2 | — | 93.32 | — | — | 97.01 | 95.96 | — | 91.73 |
| | | CD80-Fc + Fc-IL2WT | — | 91.51 | 96.49 | — | 96.19 | 95.23 | — | 91.81 |
| | 1.6 nM | GI-101 | — | 91.81 | 93.75 | — | 95.14 | — | — | 85.22 |
| | | GI-101WT | — | 93.56 | 93.56 | — | 94.81 | — | — | 88.63 |
| | | CD80-Fc + Fc-IL2v2 | — | 93.57 | 94.00 | — | 94.36 | — | — | 89.53 |
| | | CD80-Fc + Fc-IL2WT | — | 90.87 | 94.04 | — | 95.01 | — | — | 87.36 |

TABLE 10

| TOTAL CELL NUMBER (×10^5) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| Table 3 | 50 nM | GI-101 | 2.50 | 6.07 | 24.64 | — | 46.13 | 61.25 | — | 99.60 |
| | | GI-101WT | 2.50 | 6.98 | 24.90 | — | 49.75 | 64.15 | — | 67.71 |
| | | CD80-Fc + Fc-IL2v2 | 2.50 | 4.11 | — | 21.60 | — | — | — | 56.02 |
| | | CD80-Fc + Fc-IL2WT | 2.50 | 5.73 | 23.52 | — | 51.17 | 66.32 | — | 76.19 |

TABLE 10-continued

| TOTAL CELL NUMBER (×10^5) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| | 1.6 nM | GI-101 | 2.50 | 6.47 | 25.14 | — | 54.13 | 69.59 | — | 86.68 |
| | | GI-101WT | 2.50 | 3.34 | — | — | — | — | — | 10.91 |
| | | CD80-Fc + Fc-IL2v2 | 2.50 | 1.07 | — | — | — | — | — | — |
| | | CD80-Fc + Fc-IL2WT | 2.50 | 4.61 | 13.16 | — | 16.27 | — | — | 13.16 |

TABLE 11

| CELL VIABILITY (%) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| Table 3 | 50 nM | GI-101 | — | 89.72 | 90.65 | — | 90.59 | 88.11 | — | 82.08 |
| | | GI-101WT | — | 90.74 | 92.95 | — | 93.20 | 90.52 | — | 87.38 |
| | | CD80-Fc + Fc-IL2v2 | — | 87.57 | — | 88.80 | — | — | — | 87.63 |
| | | CD80-Fc + Fc-IL2WT | — | 88.60 | 93.44 | — | 95.13 | 94.99 | — | 91.38 |
| | 1.6 nM | GI-101 | — | 90.07 | 92.11 | — | 92.64 | 90.80 | — | 85.62 |
| | | GI-101WT | — | 85.76 | — | — | — | — | — | 75.98 |
| | | CD80-Fc + Fc-IL2v2 | — | 66.33 | — | — | — | — | — | — |
| | | CD80-Fc + Fc-IL2WT | — | 88.05 | 90.17 | — | 89.08 | — | — | 79.81 |

TABLE 12

| TOTAL CELL NUMBER (×10^5) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| Table 4 | 50 nM | GI-101 | 2.50 | 6.31 | 37.36 | 58.21 | — | 146.76 | — | 467.75 |
| | | GI-101WT | 2.50 | 5.74 | 30.24 | 52.00 | — | 126.99 | — | 347.59 |
| | | CD80-Fc + Fc-IL2v2 | 2.50 | 6.96 | 31.20 | 51.52 | — | 130.65 | — | 285.63 |
| | | CD80-Fc + Fc-IL2WT | 2.50 | 6.30 | 35.52 | 50.08 | — | 147.54 | — | 350.28 |
| | 1.6 nM | GI-101 | 2.50 | 6.75 | 37.28 | 63.68 | — | 166.42 | — | 419.02 |
| | | GI-101WT | 2.50 | 2.46 | — | 8.08 | 9.84 | — | — | 8.93 |
| | | CD80-Fc + Fc-IL2v2 | 2.50 | 0.73 | — | — | — | — | — | — |
| | | CD80-Fc + Fc-IL2WT | 2.50 | 3.86 | 18.85 | — | 48.90 | 67.86 | — | 134.21 |

TABLE 13

| CELL VIABILITY (%) | | | | | | | | | | |
|---|---|---|---|---|---|---|---|---|---|---|
| | | | CD3-CD56+ cells | | | | | | | |
| Culture condition | Conc. | Treated material | DAY0 (seeding) | DAY5 | DAY9 | DAY11 | DAY13 | DAY15 | DAY17 | DAY21 |
| Table 4 | 50 nM | GI-101 | — | 94.72 | 96.93 | 97.24 | — | 96.20 | — | 96.04 |
| | | GI-101WT | — | 94.90 | 96.79 | 96.11 | — | 63.11 | — | 64.73 |
| | | CD80-Fc + Fc-IL2v2 | — | 95.33 | 97.83 | 96.70 | — | 95.73 | — | 96.43 |
| | | CD80-Fc + Fc-IL2WT | — | 95.99 | 97.86 | 97.52 | — | 97.09 | — | 96.39 |
| | 1.6 nM | GI-101 | — | 94.75 | 97.72 | 96.89 | — | 94.67 | — | 95.00 |
| | | GI-101WT | — | 89.00 | — | 88.06 | — | — | — | 88.22 |
| | | CD80-Fc + Fc-IL2v2 | — | 75.94 | — | — | — | — | — | — |
| | | CD80-Fc + Fc-IL2WT | — | 91.40 | 96.61 | — | — | 96.49 | — | 95.99 |

II. Characterization of Natural Killer Cells Using Natural Killer Cell Culture Composition

Example 4. Measurement of the Purity of Natural Killer Cells

CD3-CD56+ natural killer cells obtained from Example 2 were respectively centrifuged at 300×g condition for 5 minutes to remove the supernatant, and 1 ml of FACS buffer was added to release the pellet. Then, 3% (v/v) FBS, 10 mM EDTA, 20 mM HEPES, 10 μg/ml polymyxin B, 100 U/ml penicillin, 100 μg/ml streptomycin, and 1 mM sodium pyruvate were added to PBS to prepare FACS buffer, and 1 ml of prepared FACS buffer was added to resuspend the cell pellet. Next, it was diluted with FACS buffer to $2\times10^6$ cells/ml using a cell counter.

100 μl of the diluted cell solution was added to each of a 5 ml FACS tube, and 100 μl of FACS buffer was further added thereto, followed by treatment with a PerCP-labeled anti-human CD3 antibody (PerCP human anti-CD3(Clone UCHT1)) and a PE/cy7-labeled anti-human CD56 antibody (PE/cy7 human anti-CD56(Clone B159)). Then, after incubating at 4° C. for 20 minutes, 200 μl of FACS buffer was added and centrifuged at 1,500 rpm for 3 minutes. The supernatant was removed, and 200 μl of FACS buffer was added to suspend, and then phenotype of the cells was determined using a flow cytometer (CYTEK® Aurora, Cytek, Fremont, CA, USA).

Information about antibodies used in the experiment is shown in Table 14. In addition, the purities of CD3-CD56+ natural killer cells cultured for 21 days under the conditions of the culture media compositions prepared in Preparation example 1 were measured and shown in FIGS. 13 to 16.

TABLE 14

| | Target | Color | Clone | Producer | Cat # |
|---|---|---|---|---|---|
| NK marker | CD3 | PerCP | UCHT1 | BioLegend | 300428 |
| | CD56 | APC/cy7 | 5.1H11 | BioLegend | 362512 |

Example 5. Identification of Activation and Inhibition Markers for Natural Killer Cells CD3-CD56+ natural killer cells obtained from Example 2 were respectively centrifuged at 300×g condition for 5 minutes to remove the supernatant, and 1 ml of FACS buffer was added to release the pellet. 3% (v/v) FBS, 10 mM EDTA, 20 mM HEPES, 10 μg/ml polymyxin B, 100 U/ml penicillin, 100 μg/ml streptomycin, and 1 mM sodium pyruvate were added to PBS to prepare FACS buffer, and 1 ml of prepared FACS buffer was added to resuspend the cell pellet. Then, it was diluted with FACS buffer to $2\times10^6$ cells/ml using a cell counter. 100 μl of the diluted cell solution was added each of a 5 ml FACS tube, and confirmed by using a Pe-CF594-labeled anti-human CD16 antibody (PE-CF594 human anti-CD16 (Clone 3G8)), APC-labeled anti-human DNAM1 antibody (APC human anti-DNAM1 (Clone 11A8)), BV605-labeled anti-human NKG2C antibody (BV605 human anti-NKG2C (Clone 134591)), BV650-labeled anti-human NKG2D antibody (BV650 human anti-NKG2D(Clone 1D11)), BB515-labeled anti-human NKp46 antibody (BB515 human anti-NKp46 (Clone 9E2)), BV480-labeled anti-human NKp30 antibody (BV480 human anti-NKp30 (Clone p30-15)), PE-labeled anti-human PD-1 antibody (PE human anti-PD-1 (Clone EH12.2H7)), and APC-labeled anti-human NKG2A antibody (APC anti-human NKG2A (Clone 131411)), using a flow cytometer. Then, after incubating at 4° C. for 20 minutes, 100 μl of FACS buffer was added and centrifuged at 1,500 rpm for 3 minutes.

The supernatant was removed, and 200 μl of FACS buffer was added to suspend, and then phenotype of the cells was determined using a flow cytometer (CYTEK® Aurora, Cytek, Fremont, CA, USA). Information of antibodies used in the experiment is shown in Table 15. The activation and inhibition markers for CD3-CD56+ natural killer cells cultured for 21 days under the conditions of the culture media compositions prepared in Preparation example 1 were identified and shown in FIGS. 17 to 24.

TABLE 15

| | Target | Color | Clone | Producer | Cat # |
|---|---|---|---|---|---|
| Activation marker | CD16 | PE-CF594 | 3G8 | BD | 562293 |
| | DNAM1 | APC | 11A8 | BioLegend | 338312 |
| | NKp46 | BB515 | 9E2 | BD | 564536 |
| | NKp30 | BV480 | p30-15 | BD | 746491 |

TABLE 15-continued

| | Target | Color | Clone | Producer | Cat # |
|---|---|---|---|---|---|
| Inhibition marker | PD-1<br>NKG2A | PE<br>APC | EH12.2H7<br>131411 | BioLegend<br>R&D systems | 329906<br>FAB1059A-100 |

Example 6. Determination of Granzyme B, Perforin, Interferon Gamma Secretory Capacity of Natural Killer Cells In order to determine granzyme and perforin secretory capacity of CD3-CD56+ natural killer cells obtained from Example 2, an amount of expression of granzyme B, perforin, and interferon gamma in the natural killer cells were measured by intracellular staining. The cultured natural killer cells were centrifuged at 300×g condition for 5 minutes and the supernatant was removed. Then, it was diluted with each culture composition to $2\times10^6$ cells/ml using a cell counter.

200 μl of the prepared cells were dispensed into each well of a 96-well plate, and then 1% (v/v) Stimulation Cocktail (1×) (Thermo Scientific, Waltham, MA, USA) was added and incubated at 37° C., $CO_2$ condition for 4 hours. Then, the plates were centrifuged at 300×g condition for 5 minutes and the supernatant was removed. Next, 3% (v/v) FBS, 10 mM EDTA, 20 mM HEPES, 10 μg/ml polymyxin B, 100 U/ml penicillin, 100 μg/ml streptomycin, and 1 mM sodium pyruvate were added to PBS to prepare FACS buffer, and 100 μl of prepared FACS buffer was added to resuspend the cell pellet. The supernatant was removed, and 100 μl of BD CYTOFIX/CYTOPERM™ buffer (perm/fixation buffer, BD science) was added for fixation and permeation and then suspended, followed by incubation at 4° C. for 30 minutes. 100 μl of FACS buffer was further added and centrifuged at 1,500 rpm for 3 minutes.

A PE/cy7-labeled anti-human granzyme B antibody (PE/cy7 anti-human Granzyme B (Clone NGZB)), an APC-labeled anti-human perforin antibody (APC anti-human Perforin (Clone B-D48)), and BV421-labeled anti-human interferon gamma antibody (BV421 anti-human IFN-gamma (Clone B27)) were treated. Then, after incubating at 4° C. for 20 minutes, 100 μl of FACS buffer was added and centrifuged at 1,500 rpm for 3 minutes. After supernatant was removed and 200 μl of FACS buffer (fixation buffer) was added to suspended, an amount of expression of the cells was determined using a flow cytometer.

Information of antibodies used in the experiment is shown in Table 16. The markers for CD3-CD56+ natural killer cells cultured for 21 days under the conditions of the culture media compositions prepared in Preparation example 1 were identified and shown in FIGS. 25 to 28.

TABLE 16

| | Target | Color | Clone | Producer | Cat # |
|---|---|---|---|---|---|
| Cytotoxicity | Perforin<br>IFN-γ<br>GranzymeB (GB11) | APC<br>BV421<br>PE/cy7 | B-D48<br>B27<br>NGZB | BioLegend<br>BioLegend<br>ebioscience | 353312<br>506538<br>25-8898-82 |

III. Analysis of Cancer Cell Killing Capacity of Natural Killer Cells According to a Culture Composition

Example 8. Confirmation of Degranulation Ability and Killing Effect of Natural Killer Cells Against Cancer Cells Specifically, a K562 cancer cell line (American Type Culture Collection, ATCC) was diluted in PBS to number of cells shown in Table 17 below, and dispensed into each well.

TABLE 17

| E:T | 1:1 | 1:5 | 1:10 |
|---|---|---|---|
| (E) NK cells | $2.5\times10^5$ cells | $1\times10^5$ cells | $1\times10^5$ cells |
| (T) K562 | $2.5\times10^5$ cells | $5\times10^5$ cells | $1\times10^6$ cells |

Specifically, a K562 cancer cell line was diluted with each culture composition to $1\times10^7$ cells/ml, and then dispensed according to the number of cells specified in the above table for each well. Then, natural killer cells were also diluted with each culture composition to $5\times10^6$ cells/ml, and then dispensed according to the number of cells specified in the above table for each well, and centrifuged at 30×g condition for 3 minutes. Next, after culture at 37° C., 5% $CO_2$ condition for 4 hours, a BV421-labeled anti-human CD3 antibody (BV421 human anti-CD3 (Clone UCHT1)), a PE-labeled anti-human CD16 antibody (PE human anti-CD16 (Clone 3G8)), a PE/cy7-labeled anti-human CD56 antibody (PE/cy7 human anti-CD56(Clone B159)), and a FITC-labeled anti-human CD107a antibody (FITC anti-human CD107a antibody (Clone H4A3)) were treated and incubated on ice for 20 minutes.

Then, 100 μL of FACS buffer was added and centrifuged at 1,300 rpm, 4° C. condition for 5 minutes. After removing the supernatant, 7-AAD Viability Staining Solution was treated, and light was blocked to react at room temperature for 15 minutes. Then, 100 μL of FACS buffer was added and centrifuged at 1,300 rpm, 4° C. condition for 5 minutes. 200 μL of FACS buffer was added again, and centrifuged at 1,300 rpm, 4° C. condition for 5 minutes. After repeating the above process once more, the supernatant was removed, and 400 μL of FACS buffer was added, followed by analysis using a flow cytometer (CYTEL® Aurora, Cytek, Fremont, CA, USA).

The degranulation ability and killing effect of natural killer cells cultured for 21 days in a composition in which 50 nM of the additive in Table 5 was added to the basal culture medium in Tables 1 to 4, respectively, are shown in FIGS. 29 to 34.

What is claimed is:

1. A method for culturing an isolated natural killer cell, which comprises:

culturing the isolated natural killer cell without CD3+ or CD56− cells in a composition comprising a fusion protein dimer, wherein the fusion protein comprises the following structural formula (I) or (II):

N'—X-[linker (1)]n-Fc domain-[linker (2)]m-Y—C'— formula (I)

N'—Y-[linker (1)]n-Fc domain-[linker (2)]m-X—C'— formula (II), wherein, N' is the N-terminus of the fusion protein,
C' is the C-terminus of the fusion protein,
X is a CD80 protein or a fragment thereof,
Y is an IL-2 variant thereof,
the linkers (1) and (2) are peptide linkers, and
n and m are each independently 0 or 1, wherein the CD80 fragment comprises the extracellular domain of CD80, wherein the IL-2 variant is obtained by any one selected from the following substitution combinations (a) to (d) in the amino acid sequence of SEQ ID NO: 10:

(a) R38A/F42A
(b) R38A/F42A/Y45A
(c) R38A/F42A/E61R
(d) R38A/F42A/L72G.

2. The method of claim 1, wherein the IL-2 variant consists of the amino acid sequence of SEQ ID NO: 6.

3. The method of claim 1, wherein the fragment of CD80 consists of the 35th to 242nd amino acids in the amino acid sequence of SEQ ID NO: 11.

4. The method of claim 1, wherein the fusion protein consists of the amino acid sequence of SEQ ID NO: 9, 26, 28, or 30.

5. A method for culturing a natural killer cell without CD3+ or CD56-cells, which comprises:

i) isolating a cell, comprising one of (A), (B), or (C):

(A) isolating a cell that does not express CD3 from peripheral blood mononuclear cells (PBMCs), (B) isolating a cell that expresses CD56 from PBMCs, or (C) isolating a cell that does not express CD3 from PBMCs, and isolating a cell that expresses CD56 from the cell that does not express CD3, isolated in the first isolating step; and ii) culturing the isolated cell in the presence of a fusion protein dimer, wherein the fusion protein comprises the following structural formula (I) or (II):

N'—X-[linker (1)]n-Fc domain-[linker (2)]m-Y—C'— formula (I)

N'—Y-[linker (1)]n-Fc domain-[linker (2)]m-X—C'— formula (II), wherein, N' is the N-terminus of the fusion protein,
C' is the C-terminus of the fusion protein,
X is a CD80 protein or a fragment thereof,
Y is an IL-2 variant thereof,
the linkers (1) and (2) are peptide linkers, and
n and m are each independently 0 or 1, wherein the CD80 fragment comprises the extracellular domain of CD80, wherein the IL-2 variant has any one selected from the following substitution combinations (a) to (d) in the amino acid sequence of SEQ ID NO: 10:

(a) R38A/F42A
(b) R38A/F42A/Y45A
(c) R38A/F42A/E61R
(d) R38A/F42A/L72G.

6. The method of claim 5, wherein the isolating of step i) comprises:

(C) isolating a cell that does not express CD3 from PBMCs, and isolating a cell that expresses CD56 from the cell that does not express CD3, isolated in the first isolating step.

7. The method of claim 6, wherein the fusion protein dimer in said culturing ii) is at a concentration of 1 nM to 500 nM.

8. The method of claim 6, wherein the culture period in the culturing step is 5 days to 25 days.

9. The method of claim 5, wherein the isolating i) comprises:

(A) isolating a cell that does not express CD3 from peripheral blood mononuclear cells (PBMCs).

10. The method of claim 5, wherein the isolating i) comprises:

(B) isolating a cell that expresses CD56 from PBMCs.

* * * * *